(12) United States Patent
Bauer et al.

(10) Patent No.: US 7,157,092 B1
(45) Date of Patent: Jan. 2, 2007

(54) ACYL PSEUDODIPEPTIDES, PREPARATION METHOD AND PHARMACEUTICAL COMPOSITIONS CONTAINING SAME

(75) Inventors: Jacques Bauer, Saint-Prex (CH); Olivier Richard Martin, Orleans (FR)

(73) Assignee: Om Pharma, Meyrin (CH)

( * ) Notice: Subject to any disclaimer, the term of this patent is extended or adjusted under 35 U.S.C. 154(b) by 0 days.

(21) Appl. No.: 09/720,045

(22) PCT Filed: Jun. 23, 1999

(86) PCT No.: PCT/IB99/01170

§ 371 (c)(1),
(2), (4) Date: Dec. 18, 2000

(87) PCT Pub. No.: WO00/00462

PCT Pub. Date: Jan. 6, 2000

(30) Foreign Application Priority Data

Jun. 30, 1998 (FR) .................. PCT/FR98/01396

(51) Int. Cl.
*A61K 31/66* (2006.01)
*A61P 37/02* (2006.01)
*C07C 237/00* (2006.01)
*C07F 9/09* (2006.01)

(52) U.S. Cl. .................. 424/278.1; 514/108; 514/119; 554/36; 562/14; 562/15; 562/102; 562/561; 562/565; 564/159

(58) Field of Classification Search ............. 424/278.1; 514/108, 119, 553, 563, 578, 626; 554/36; 562/14, 15, 102, 106, 561, 564, 565; 564/152, 564/154, 159
See application file for complete search history.

(56) References Cited

FOREIGN PATENT DOCUMENTS

| EP | 0 224 260 A | * | 6/1987 |
| EP | 0 668 289 A | * | 8/1995 |
| WO | WO 95/14026 A | * | 5/1995 |

OTHER PUBLICATIONS

Patent Abstracts of Japan, of JP 61-227586 (Oct. 9, 1986).*
Chemical Abstracts 127:109122h (Aug. 25, 1997).*
Chemical Abstracts 126:238583n (May 5, 1997).*
Chemical Abstracts 123:33547v (Jul. 17, 1995).*

* cited by examiner

Primary Examiner—Jeffrey Edwin Russel

(57) ABSTRACT

Compounds of the formula $$X-A-(CH_2)_m-\underset{NHR_1}{CH}-(CH_2)_n-CO-NH-(CH_2)_p-\underset{NHR_2}{CH}-(CH_2)_q-B-Y \quad I$$

wherein the substitutents are defined as in the specification useful for modulating immune responses in warm-blooded animals.

14 Claims, 32 Drawing Sheets

Induction of bone marrow stem cell proliferation

Induction of NO production in murine macrophage cells

Incorporation of Dextran-FITC conjugate

Dextran-FITC conjugate take-up : Dose related effect at low concentrations

Dose related effect in terms of Dextran-FITC conjugate take-up at high concentrations CD40 co-stimulating surface marker expression Expression of CD86 co-stimulating surface marker Expression of CD83 co-stimulating surface marker Expression of CD80 co-stimulating surface marker Effect of OM-294-MP and OM-294-DP products on αTNF production by predendritic cells at DC-6 stage Effect of OM-294-MP and OM-294-DP products on IL-12 p70 production by predendritic cells at DC-6 stage (IFN = γ IFN)

Effect of OM-294-MP products on IL-12 p70 production by monocytes (IFN = γ IFN)

ELISA 2 after the first immunization treatment

ELISA 3 after the second immunization treatment

ELISA 4 after the third immunization treatment

Antibody titer before and after one, two and three immunizations treatments

ELISPOT γ IFN-producing lymphocytes of inguinal lymph nodes stimulated by Pb CS 245 - 252 one week after the second immunization treatment ELISPOT γ IFN-producing lymphocytes of the spleen stimulated by Pb CS 245 - 252 one week after the second immunization ELISPOT γ IFN-producing lymphocytes of the spleen stimulated by Pb CS 245 - 252 one week after the second immunization ELISPOT γ IFN-producing lymphocytes of the spleen stimulated by Pb CS 245 - 252 three weeks after the third immunization Electrophoretogram of OM-294-DP alone, of Pb CS His6-242-310 antigen alone and of Pb CS His6-242-310 - OM-294-DP complex Increase in the anti-gp63 immune response under the effect of OM-294-MP adjuvant : Comparison with BCG In vitro lymph node lymphocyte response derived from mice previously immunized in vivo with LmCPb antigen : effect of OM-294-MP adjuvant during the primary response FIGURE 32 (a)

Increase in the anti-LmCPb immune response under the effect of OM-294-MP adjuvant : Comparison with BCG

FIGURE 32 (b)

FIGURE 35
SYNTHESIS SCHEME 3
Bn = benzyl
Ph = phenyl
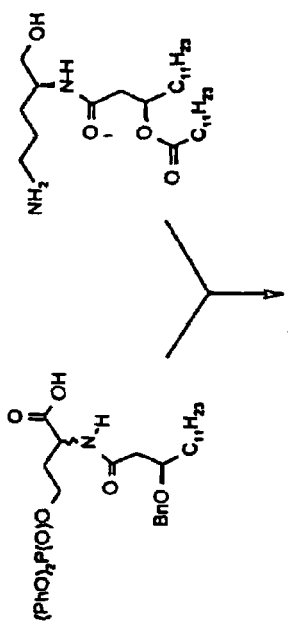
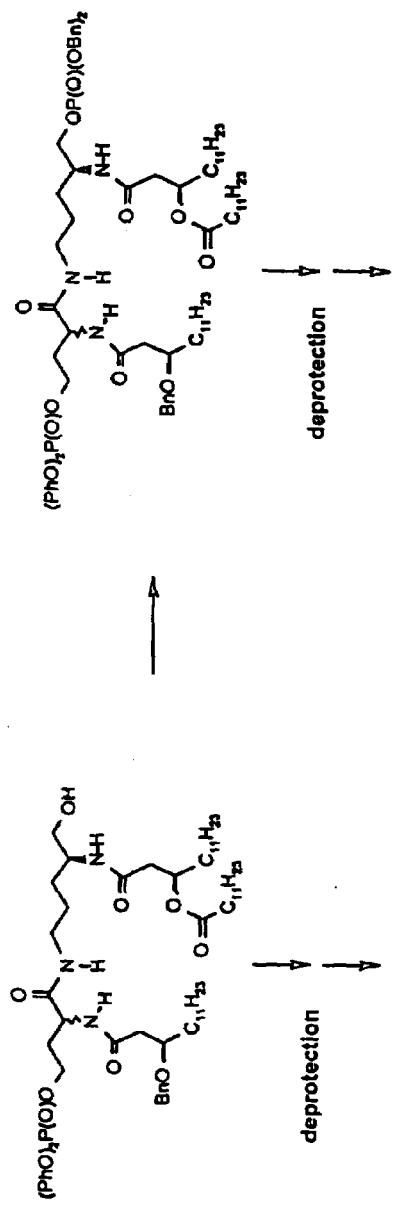
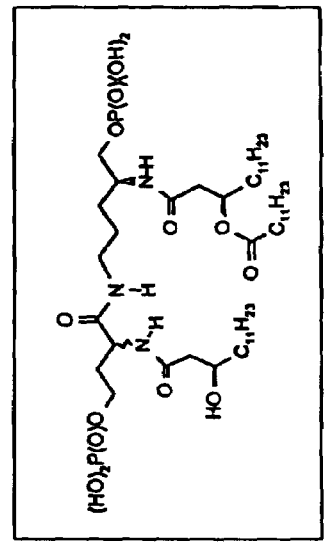
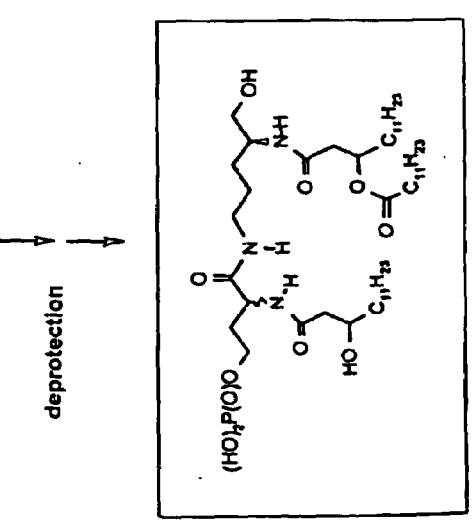

SPECTRUM 3

Diphosphorylated compound

ES-MS spectra (positive mode fragmentation)

Instrumentation: Hewlett-Packard MSD, single quadrupole

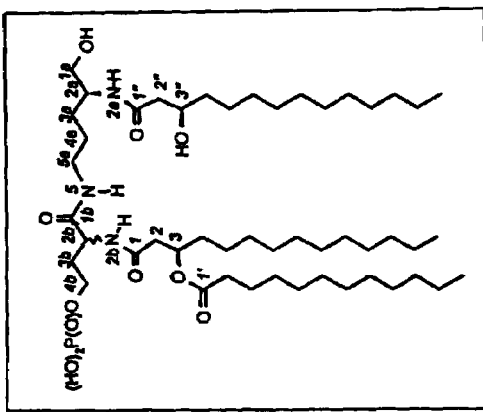
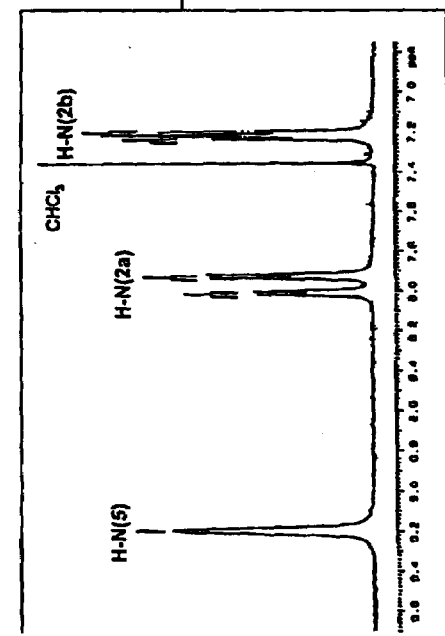
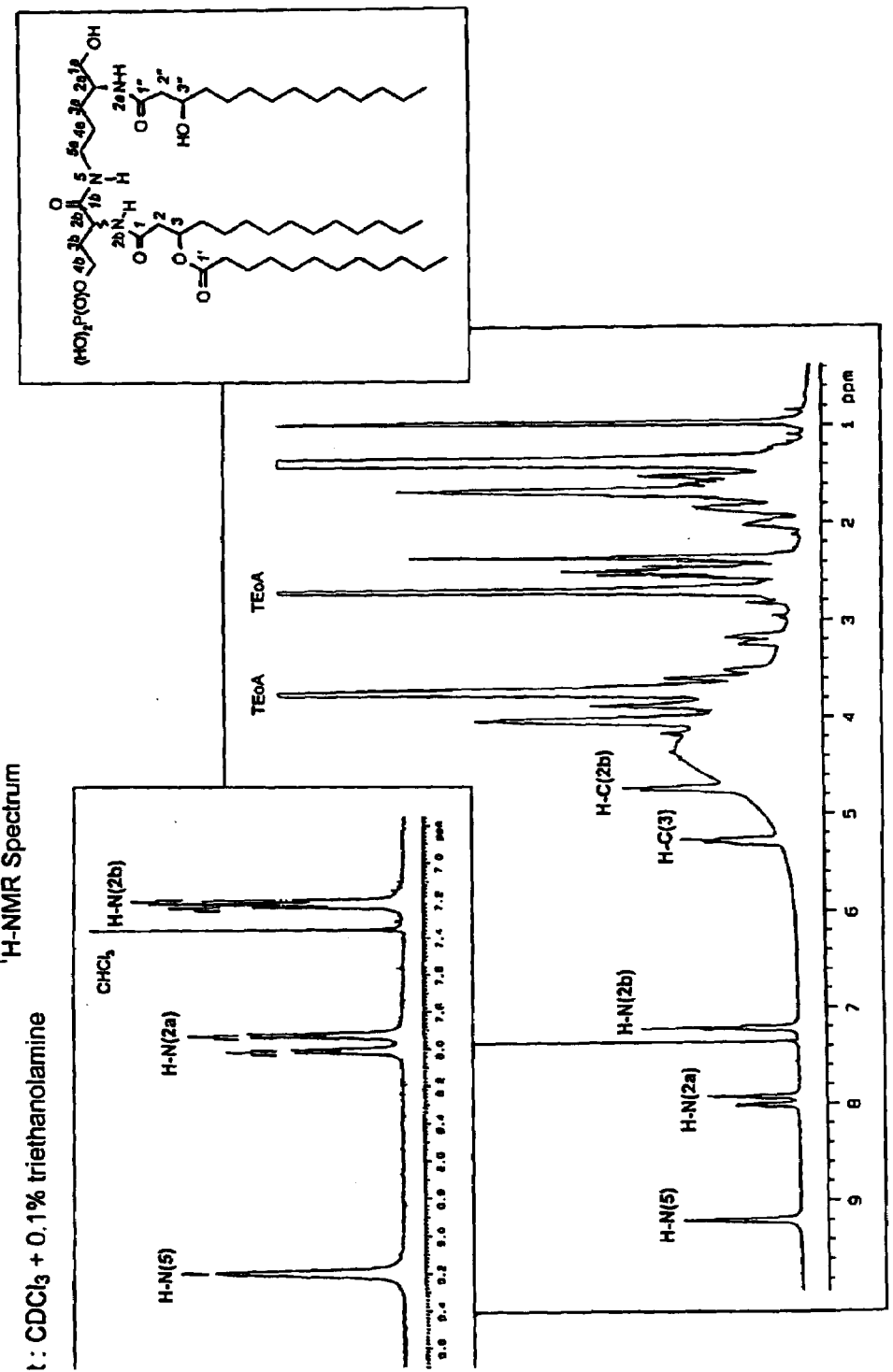
FIGURE 42

Spectrum 7
Diphosphorylated compound
$^{13}$C-NMR Spectrum

Solvent: CDCl$_3$

Instrumentation: Bruker DPX 250 MHz

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 1

Ile Glu Ala Arg
1

<210> SEQ ID NO 2
<211> LENGTH: 78

```
<212> TYPE: PRT
<213> ORGANISM: Artificial Sequence
<220> FEATURE:
<223> OTHER INFORMATION: Description of Artificial Sequence: Synthetic
      peptide; residues 242-310 of Plasmodium berghei

<400> SEQUENCE: 2

His His His His His His Gly Gly Met Asn Asn Lys Asn Asn Asn Asn
 1               5                  10                  15

Asp Asp Ser Tyr Ile Pro Ser Ala Glu Lys Ile Leu Glu Phe Val Lys
             20                  25                  30

Gln Ile Arg Asp Ser Ile Thr Glu Glu Trp Ser Gln Cys Asn Val Thr
         35                  40                  45

Cys Gly Ser Gly Ile Arg Val Arg Lys Arg Lys Arg Gly Ser Asn Lys
     50                  55                  60

Lys Ala Glu Asp Leu Thr Leu Glu Asp Ile Asp Thr Glu Ile
65                  70                  75
```

ACYL PSEUDODIPEPTIDES, PREPARATION METHOD AND PHARMACEUTICAL COMPOSITIONS CONTAINING SAME

This application is a 371 of PCT/IB99/01170 filed Jun. 23, 1999.

FIELD OF THE INVENTION

The present invention relates to the field of chemistry and more specifically to the field of medicinal chemistry More particularly, it is directed to dipeptide-like compounds derived from hydroxylated amino acids, the free amine functional groups of which are subject to amide formation by means of fatty acids.

The invention is specifically concerned with N-acyl-dipeptide-like compounds at least one hydroxyl group of which is esterified by an acid group in the neutral or charged form, having the general formula I

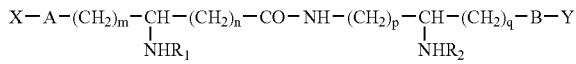

wherein $R_1$ and $R_2$ each designate an acyl group derived from a saturated or unsaturated straight or branched chain-carboxylic acid having from 2 to 24 carbon atoms, which is unsubstituted or bears one or more substituents selected among hydroxyl, alkyl, alkoxy, acyloxy, amino, acylamino, acylthio and $((C_{1-24})alkyl)thio$ groups, subscripts m, p and q are integers ranging from 1 to 10, subscript n is an integer ranging from 0 to 10, X and Y each designate a hydrogen or an acid group either in neutral or charged form, provided that at least one of substituents X and Y designates an acid group in neutral or charged form, A and B designate, independantly from each other, an oxygen atom, a sulfur atom or an imino group —NH—.

Acid groups X and Y are preferably selected among the following groups:

carboxy $[(C_{1-5})alkyl]$

CH—$[(CH_2)_m COOH][(CH_2)_n COOH]$ with m=0 to 5 and n=0 to 5 phosphono $[(C_{1-5})alkyl]$ dihydroxyphosphoryloxy$[C_{1-5})alkyl]$ dimethoxyphosphoryl phosphono hydroxysulfonyl hydroxysulfonyl$[(C_{1-5})alkyl]$ hydroxysulfonyloxy $[(C_{1-5})alkyl]$ Where substituents X and/or Y designate an acid group in neutral form, reference is made to the free carboxylic, sulfonic or phosphoric form. Where the acid group is in charged form, reference is made to the carboxylic, sulfonic or phosphoric salt form, namely by addition of an organic or mineral base, preferably one intended for therapeutic use. In case where bases are not intended for therapeutic use, such bases provide a means for easy identification, purification and separation.

Similar considerations apply where X and/or Y designate a carboxylalkyl, alcenylbiscarboxylic, hydroxysulfonyl, hydroxysulfonylalkyl, hydroxysulfonyloxyalkyl, phosphonoalkyl, phosphoryloxyakyl group.

Salt forming bases intended for therapeutic use mainly include alkaline bases such as sodium, potassium or lithium hydroxides, ammonium salts, alkali earth metal bases such as calcium or strontium hydroxide, magnesium salts, ferrous metal salts and the like, organic bases such as those derived from primary, secondary, tertiary amines such as methylamine, diethylamine, monoethanolamine, diethanolamine, benzylamine, N-methylbenzylamine, veratrylamine, trimethoxybenzylamine, basic amino acids such as lysine and ornithine or amino sugars.

Examples of bases not intended for therapeutic use are brucine, strychnine, agmatine, homarine, glucosamine, N-methylglucosamine or N-methylmorpholin. As previously stated, salts derived therefrom will serve as separation and identification means.

When m is equal to 1 and n is equal to 0, the molecule of interest derives from serine. Where m is equal to 2 and n is equal to 0, the molecule being considered derives from homoserine. If m is equal to 3 and n is equal to 0, reference is made to a pentahomoserine compound. If m is equal to 4 and n is equal to 0, reference is made to a hexahomoserine compound.

Where p is equal to 3 and q is equal to 1, the product of interest may be a citrulline, ornithine or arginine compound. Where p is equal to 4 and q is equal to 1, reference is made to a homoarginine or lysine compound.

Among dipeptide-like compounds which are herein included, special attention is devoted to compounds of general formula I which are currently preferred:

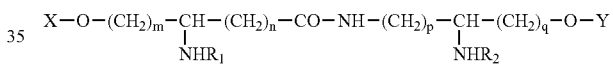

wherein $R_1$ and $R_2$ each designate an acyl group derived from a saturated or unsaturated, straight or branched chain-carboxylic acid having from 2 to 24 carbon atoms, which is unsubstituted or bears one or more substituents selected from the group comprised of hydroxyl, alkyl, alkoxy, acyloxy, amino, acylamino, acylthio and $((C_{1-24})alkyl)thio$ groups, subscripts m, p and q are integers ranging from 1 to 10, subscript n is an integer ranging from 0 to 10, X and Y each designate a hydrogen atom or a phosphono group.

and namely 3-(3-dodecanoyloxytetradecanoylamino)9-(3-hydroxytetradecanoylamino)$_4$-oxo-5-azadecan-1,10-diol 1 and/or 10-dihydrogenphosphate and its addition salts formed with an organic or a mineral base, 3-(3-dodecanoyloxy-tetradecanoylamino)9-(3-hydroxytetradecanoylamino)4-oxo-5-azadecan-1,10-diol 1,10-bis(dihydrogenphosphate) and its addition salts formed with an organic or a mineral base, 3-(3-hydroxytetradecanoylamino)9-(3-dodecanoyloxytetradecanoylamino)$_4$-oxo-5-azadecan-1,10-diol 1,10-bis(dihydrogenphosphate) and its addition salts formed with an organic or a mineral base, 3-(3-dodecanoyloxytetradecanoylamino)9-(3-hydroxytetradecanoylamino)4-oxo-5-azadecan-1,10-diol 1-dihydrogenophosphate and its addition salts with an organic or mineral base, 3-(3-hydroxytetradecanoylamino)9-(3-dodecanoyloxytet-radecanoylamino)4-oxo-5-azadecan-1,10-diol 1-dihydrogenphosphate and its addition salts formed with an organic or a mineral base 3-(3-hydroxytetradecanoylamino)9-(3-dodecanoyloxytet-radecanoylamino)4-oxo-5-azadecane-1,10-diol 10-dihydrogenphosphate and its addition salts formed with an organic or a mineral base.

$R_1$ and $R_2$ are meant to include saturated or unsaturated, branched or straight chain-acyl derivatives having a variable size chain, of distinct or identical nature, which can bear one or more substituents selected from the group comprised of alkyl, amino, acylamino, hydroxyl, alkoxy, acyloxy acylthio and alkylthio groups, Examples of such acylated, substituted derivatives are ricinoleyl, 12-hydroxystearoyl, 2-hydroxy-3-methylbutyroyl, 3-hydroxy-2-aminopentanoyl, palmitoyl, elaidyl, eleostearoyl, arachidoyl, arachidonyl, gadoleyl, behenyl, erucyl, 8-methyldecanoyl, 9-methyldecanoyl, docosohexaenoyl or eicosapentaneoyl radicals.

Compounds of general formula I and notably mono- and bis-phosphorylated compounds referred to in code names as OM-294-MP (MP) and OM-294-DP (DP), respectively, have distinctive interesting pharmacological properties, mainly with regard to immunomodulation. They are particularly relevant in the treatment of diseases related to a deficiency in the immune defense system or an overexpression of immune responses, depending on doses being used. They find equally use in cancer therapy and as adjuvants or response enhancers in formulating vaccines.

Other applications include use as vectors for molecules of therapeutic interest due to their ability to form non covalent complexes based on hydrophilic or hydrophobic interactions. Their amphophilic character enhances formulation and transport of molecules of therapeutic interest to the membrane receptors, as well as the cell membranes and cytoplasm. They can be used alone or in conjunction with a molecule of therapeutic interest by administering them through oral, parenteral, rectal, topical, subcutaneous or submucosal route. They can be used solely or in combination with a molecule of therapeutic interest by carrying out extemporaneous incubation ex vivo with blood cells in order to promote formation of immunocompetent cells before injecting them back in vivo using parenteral administration.

MP and DP molecules display similar properties, as adjuvants for the immune system when used for example in vaccination, in combination with the appropriate antigens, against diseases of viral, parasitic, microbial or fungal origin. In contrast, the compounds according to the invention show utterly different properties regarding their capacity to induce cytokine production or maturation of immunocompetent stem cells derived from hematopoietic and lymphoid organs.

MP compound promotes maturation and differenciation of monocytes into functional dendritic cells, in presence or absence of the appropriate antigen and acts in promoting humoral and cell mediated immunity. DP compound shows, on the other hand, antitumoral properties.

The compounds in accordance with the invention are particularly interesting due to their low toxicity. They are used for treating humans and animals in doses ranging from 0.025 mg to 100 mg per unit dosage and from 0.05 to 200 mg daily.

The present invention is equally directed to a method for obtaining dipeptide-like compounds of general formula 1, which comprises the steps of blocking amine functional groups in positions (q+1) and ω of diamino acid by blocking reagents which readily undergo acidolysis and hydrogenolysis, respectively, reacting the still free carboxylic functional group with a reducing agent to yield a corresponding alcohol, freeing the amine functional group in position (q+1) and then acylating by means of a carboxylic acid functional deirvative of formula $R_2OH$, wherein $R_2$ is as defined above, and subsequently freeing the terminal amine functional group by hydrogenolysis to yield the diamino alcohol of general formula II

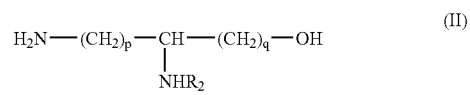

wherein $R_2$ designates an acyl group derived from a saturated or unsaturated, straight or branched chain-carboxylic acid having from 2 to 24 carbon atoms, which is unsubstituted or bears one or more substituents as defined above, p and q each designate an integer ranging from 1 to 10, which amino alcohol is condensed in presence of a peptide condensing agent in an inert solvant, together with a ω-hydroxy, ω-amino or ω-thio amino acid compound of general formula III

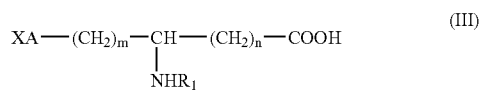

wherein $R_1$ designates an acyl group derived from a saturated or unsaturated, straight or branched chain-carboxylic acid having from 2 to 24 carbon atoms, which is unsubstituted or bears one or more substituents as defined above m is an integer ranging from 1 to 10, and n is an integer ranging from 0 to 10, and X is an acid group as specified previously which is optionally in an ester form in order to produce a dipeptide-like compound of general formula IV

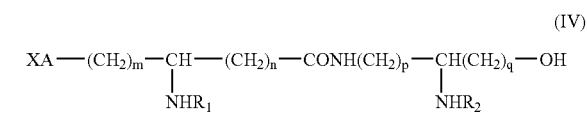

wherein substituents $R_1$, $R_2$, and subscripts n, m, p and q have the same meanings as specified above, the terminal free alcohol functional group of which can be—if necessary—alkyl or acyl or otherwise substituted by an alkyl or acyl or an otherwise substitution reagent, if needed, in presence of a coupling agent, and subjected to a catalytic hydrogenation or some other deprotection treatment in order to obtain the derivative of general formula I

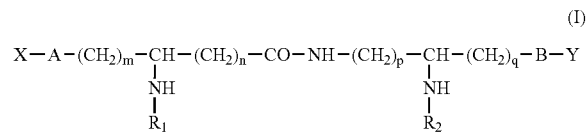

wherein A, B, as well as substituents and subscripts X, Y, $R_1$, $R_2$, n, m, p and q have the same meanings as those given above.

The invention is also directed to a method for obtaining phosphodipeptide-like compounds of general formula I'

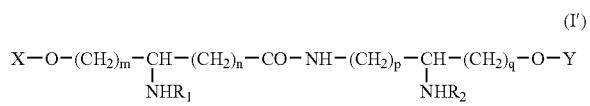
(I')

wherein $R_1$ and $R_2$ each designate an acyl group derived from a saturated or unsaturated, straight or branched chain-carboxylic acid having from 2 to 24 carbon atoms, which is unsubstituted or bears one or more substituents selected from the group comprises of hydroxyl, alkyl, alkoxy, acyloxy, amino, acylamino, acylthio and $((C_{1-24})alkyl)$thio groups, subscripts m, p and q are integers ranging from 1 to 10, subscript n is an integer ranging from 0 to 10, X and Y each designate a hydrogen atom or a phosphono group, which consists in blocking amine functional groups in positions (q+1) and ω of a diamino acid of formula $H_2N(CH_2)_p CHNH_2(CH_2)_{q+1}COOH$ by blocking reagents which readily undergo acidolysis and hydrogenolysis, respectively, reacting the still free carboxylic functional group with a reducing agent to yield a corresponding alcohol, freeing the amine functional group in position (q+1) and then acylating by means of a carboxylic acid functional deirvative of formula $R_2OH$ wherein $R_2$ is as defined above, then freeing the terminal amine functional group by hydrogenolysis to obtain an amino alcohol of general formula II

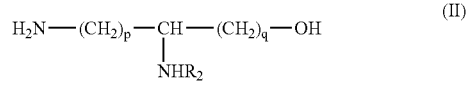
(II)

wherein $R_2$ designates an acyl group derived from a saturated or unsaturated, straight or branched chain-carboxylic acid having from 2 to 24 carbon atoms, which is unsubstituted or bears one or more substituents as specified above, p and q designate an integer ranging from 1 to 10 which amino alcohol is condensed in presence of a peptide condensing agent in an inert solvent, together with an ω-hydroxy amino acid functional derivative of general formula III':

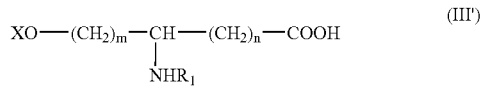
(III')

wherein $R_1$ is an acyl group derived from a saturated or unsaturated, straight or branched chain-carboxylic acid having from 2 to 24 carbon atoms, which is unsubstituted or bears one or more substituents, m is an integer ranging from 1 to 10, n is an integer ranging from 0 to 10, and X is dialkyloxy- or diaryloxy-phosphoryl radical of formula

to yield the peptide-like compound of general formula IV'

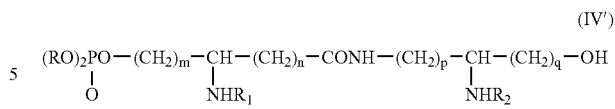
(IV')

wherein substituents $R_1$, $R_2$, and subscripts m, n, p and q are as defined above, and R is a radical which readily undergoes hydrogenolysis, the other alcohol functional group of which can be—if desired—phosphorylated by a phosphorylating agent in presence of a coupling agent, if needed, and subjected to a catalytic hydrogenation on one hand in order to unblock the alcohol functional group optionally present on acyl group $R_2$ and on the other, free the phosphate functional group and then unblock through hydrogenolysis the second optionnally present phosphate functional group, in order to obtain the derivative of general formula V

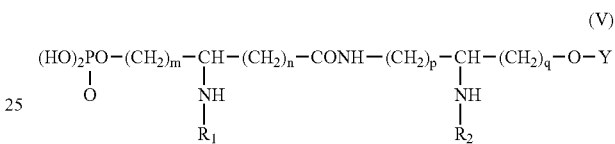
(V)

wherein Y designates either a hydrogen atom or a phosphono group, and optionally performing the further step of salt formation by means of an organic or mineral base.

Stereochemistry of chiral centers of acylamino groups is determined by initially used amino acid configuration whereas stereochemistry of acylamino groups depends on initially used fatty acid configuration. One can start from a diamino acid having L or D configuration or of a racemic nature. One can start from a hydroxylated amino acid of L, D configuration or of a racemic mixture. All such stereoisomers or diastereoisomers are included in the scope of the invention.

BRIEF DESCRIPTION OF THE DRAWINGS

FIGS. 32(a) and 32(b) are graphs of anti-LmCPb immune response;

FIGS. 33 to 38 are schemes outlining the synthetic processes of the invention;

FIGS. 42 and 43 are $^1$H-NMR spectra of the compounds of the invention;

Figure 33:
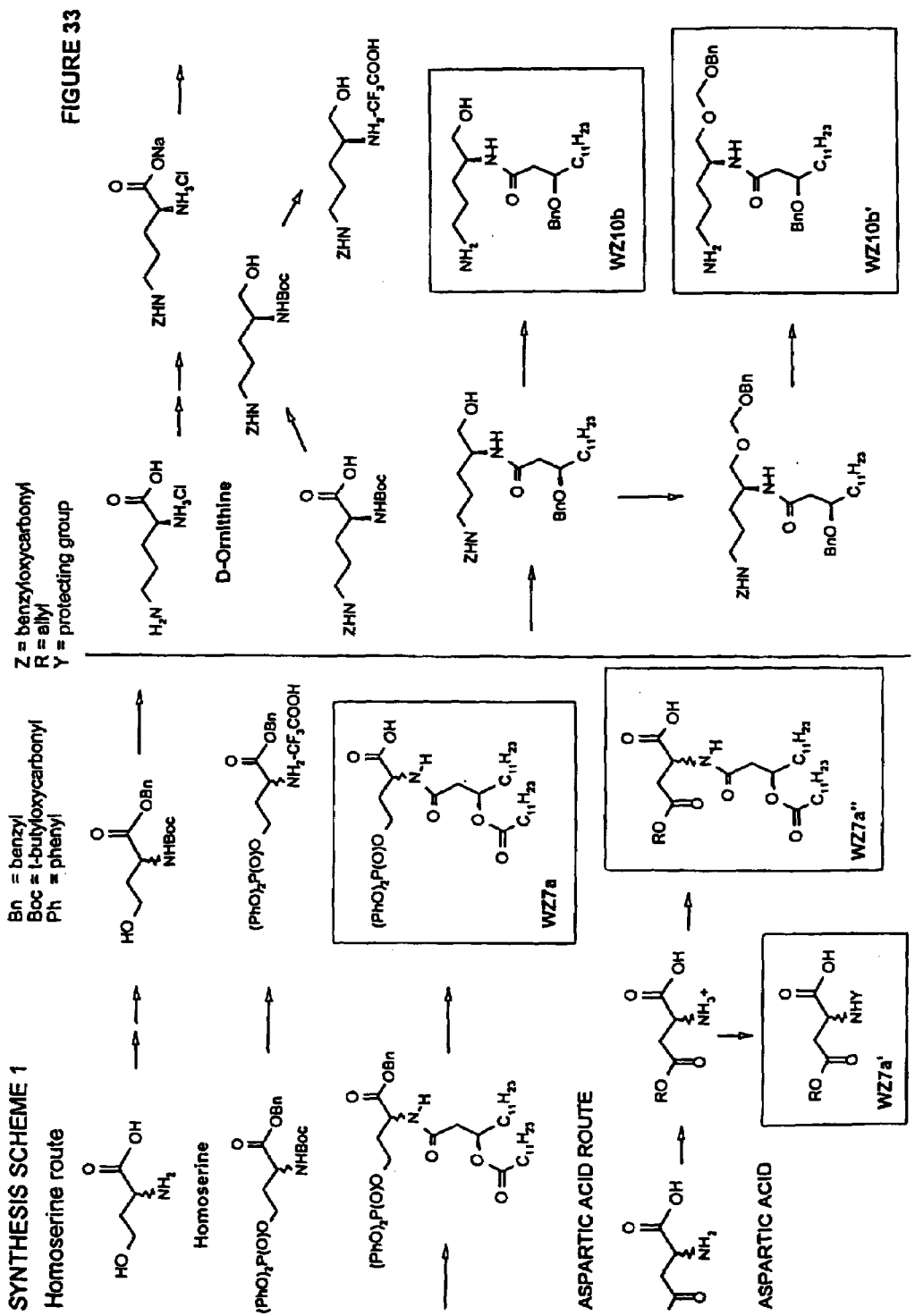
Figure 34:
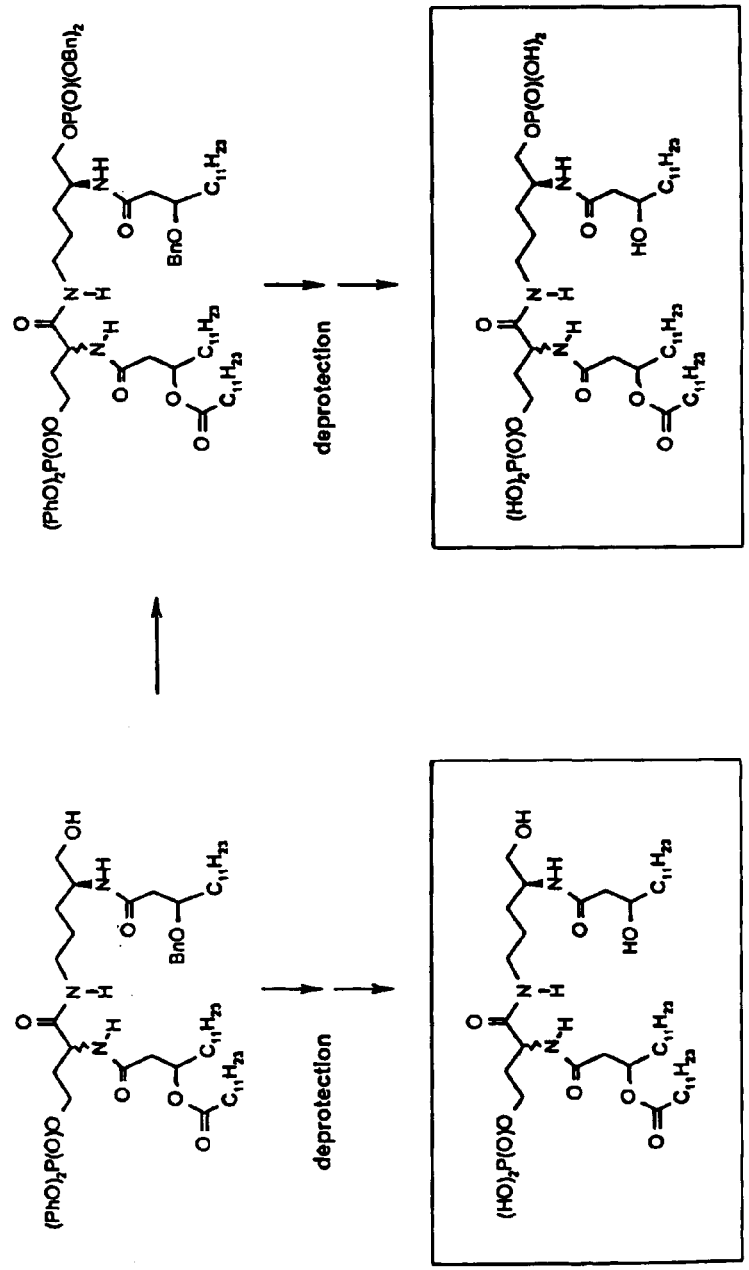
Figure 36:
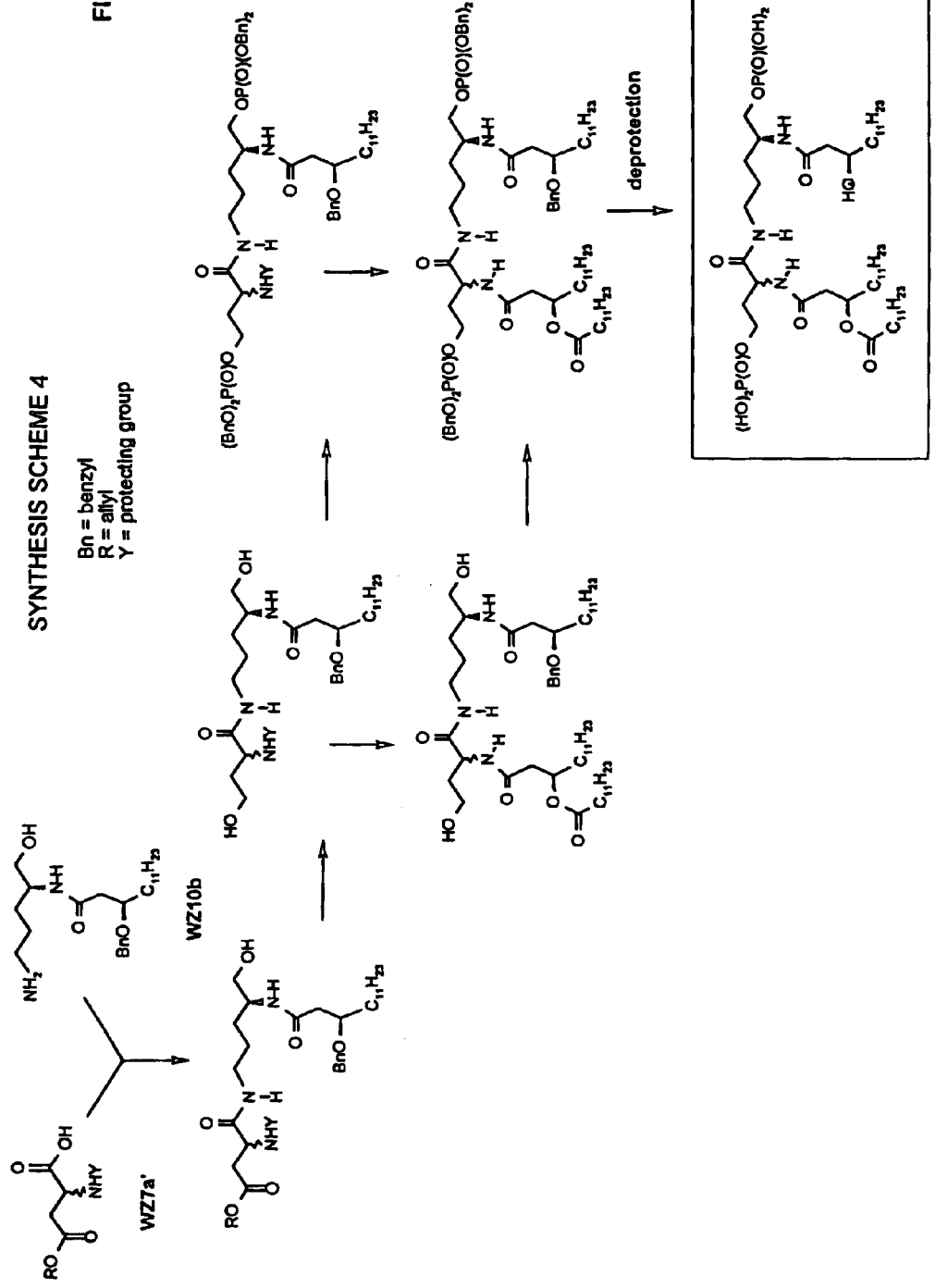
Figure 37:
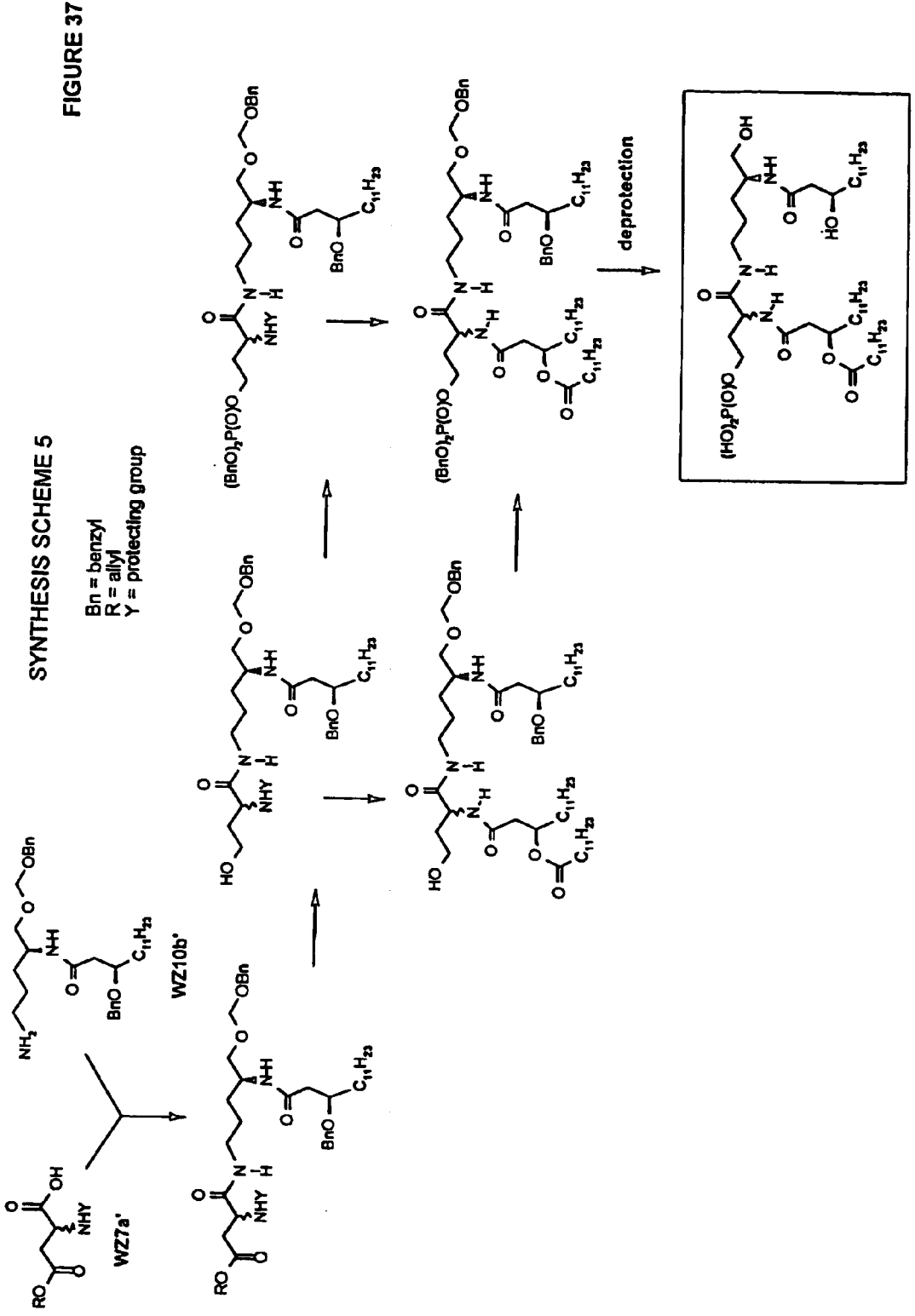
Figure 38:
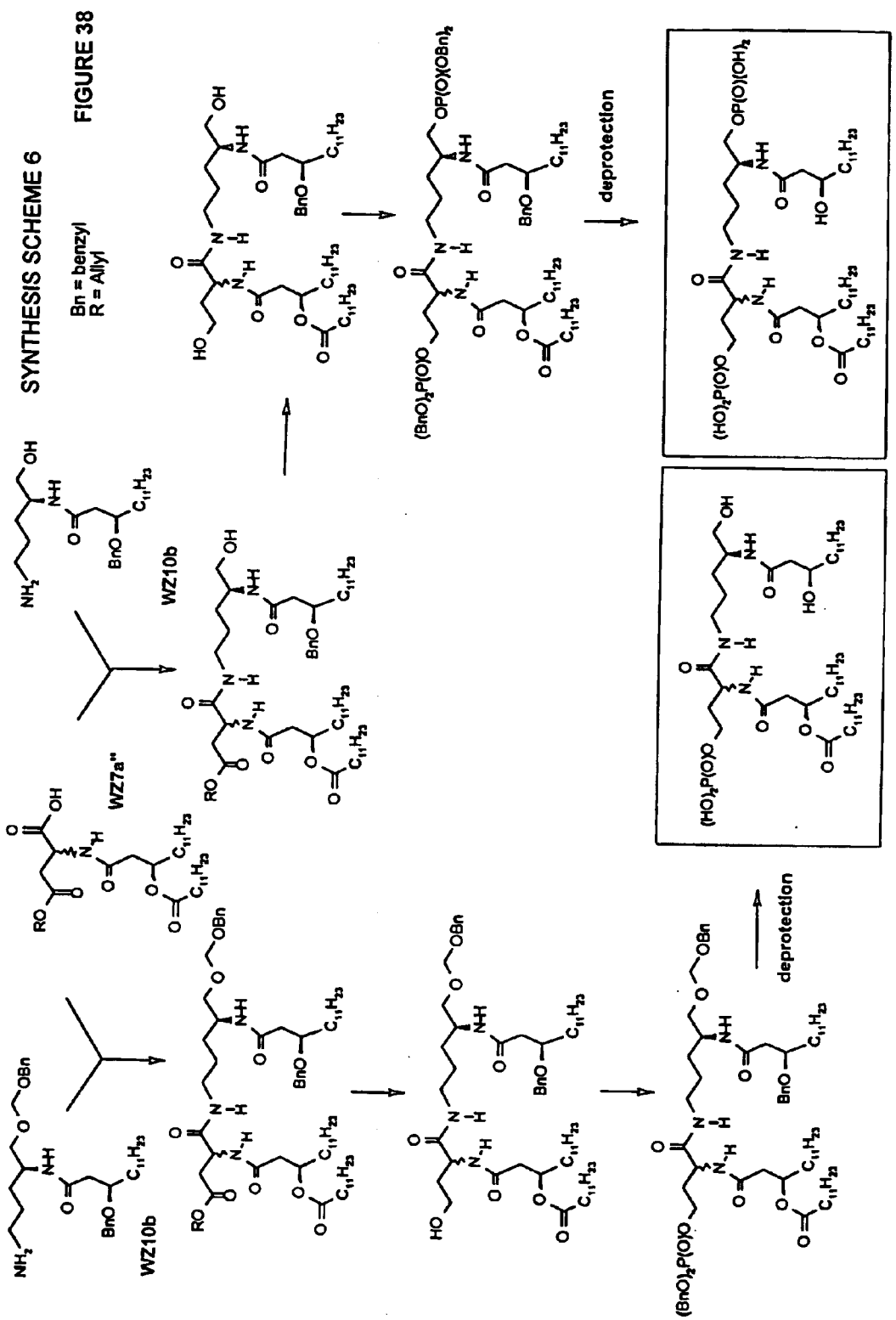

The method according to the invention can still further be defined by the following currently preferred operating procedures which are outlined is reaction schemes 1, 2 and 3 (FIGS. 33, 34 and 35):

1. Blocking the amine functional group in position ω of the ornithine derivative chain is accomplished by N-benzyloxycarbonyl substitution after initially reacting the acid functional group with a copper salt, in alkaline medium, reacting this copper carboxylate with benzyl chloroformate and freeing the carboxylic functional group by chelating copper in an acid environment, in order to obtain an N-benzyloxycarbonyl-substituted derivative, according to the method disclosed in "Organic Preparations and Procedures International, 23 (1992): 191–194".

2. Blocking the amine functional group in position α of the ornithine derivative carboxyl moiety is performed by terbutyloxycarbonyl substitution by means of an alkyl pyrocarbonate such as terbutyl pyrocarbonate in alkaline medium.

Terbutyl pyrocarbonate reacts with the proximal amine functional group to give the ω-benzyloxycarbonylamino α-terbutylcarbonylamino carboxylic derivative.

3. Conversion of the carboxylic functional group into a primary alcohol functional group is effected according to the method disclosed in Tetrahedron Letters, 32 (1991) 923–926 which consists in reacting the carboxylic derivative with an alkyl chloroformate, such as isobutyl chloroformate, to form a mixed anhydride which is reduced by means of an alkaline or an alkali-earth metal borohydride, to finally yield the corresponding hydroxylated derivative, having a primary alcohol functional group.

4. Removal of the terbutyloxycarbonyl group in position α is performed using trifluoroacetic acid which at the same time allows the formation of an amine functional group corresponding trifluoroacetate.

5. Acylation of the thus freed amine functional group is accomplished starting from a trifluoroacetic salt by means of a mixed anhydride prepared from $R_2$OH acid and an alkyl chloroformate.

6. Freeing of the terminal amine functional group is accomplished by hydrogenolysis in presence of a noble metal-based catalyst such as platinium, palladium on a carbon or iridium support material.

7. Peptide coupling or linkage between the amino compound of formula II and the phosphoryl derivative of formula III' is accomplished in presence of a coupling agent such as 1-isobutyloxy-2-isobutyloxycarbonyl-1,2-dihydroquinoline in an inert solvent such as a halogen-containing solvent, or in presence of a carbodiimide.

Hence, there is obtained a dipeptide-like compound of general formula (IV') the hydroxyl functional group of which optionally born by the acyl group $R_2$ is blocked.

8. Freeing of the hydroxyl functional group of the acyl group $R_2$ involves hydrogenolysis in presence of a noble metal such as palladium, applied on a substrate like carbon.

9. Freeing of the phosphoric group is accomplished by catalytic hydrogenation in presence of a noble metal oxide such as platinium oxide.

10. Phosphorylation of the dipeptide-like derivative IV' is accomplished in a two-step process (*Helv. Chim. Acta,* 70 (1987), 175) During the first step, compound IV' is reacted with a dialkyl or diaryl-N,N-dialkyl phosphoramidite, in presence of a coupling agent such as [1H]tetrazole in a polar solvent such as tetrahydrofurane; the phosphite thus formed is then oxidized into a phosphate by means of an aromatic peroxycarboxylic acid such as for instance peroxyphtallic acid, m-chloroperbenzoic acid or nitroperbenzoic acid. Freeing of the phoshoric group Y (formula V) is done by catalytic hydrogenation in presence of a noble metal such as palladium impregnated on carbon.

11. Phosphorylation of the homoserine derivative is effected by means of a diphenylphosphoryl halide in presence of pyridine and N,N-dialkylaminopyridine (*Helv. Chim. Acta,* 58: (1975), 518), after blocking the amine functional group by terbutoxycarbonyl substitution by means of terbutyl pyrocarbonate in alkaline medium and blocking the carboxylic functional group following the formation of a cesium salt, and benzylation by means of a benzyl halide in dimethylformamide or dimethylacetamide.

12. Acylating the nitrogen atom of the homoserine derivative is accomplished by deprotecting the amine functional group by trifluoroacetic acid to obtain the amine trifluoroacetic salt, and reacting with the mixed anhydride resulting from the reaction between the carboxylic acid $R_1$OH and an alkyl chloroformate in presence of a reactive amine such as N-methylmorpholin.

The invention further relates to intermediates of general formula II and general formulae III and III', either in the form of a pure enantiomer or a mixture of stereoisomers.

The invention still relates to pharmaceutical compositions containing as an active ingredient at least one compound of general formula I, either in neutral or charged form, in combination or in admixture with a non toxic, pharmaceutically acceptable, inert excipient or carrier.

The invention relates more specifically to pharmaceutical compositions containing as an active ingredient at least one salt of a compound of general formula I, together with an organic or mineral base intended for therapeutic use.

The invention still further relates to pharmaceutical compositions based on a compound of general formula I, either in the form of a pure enantiomer or in the form of a mixture of stereoisomers, in combination or in admixture with a pharmaceutical excipient or carrier.

Among pharmaceutical formulations herein contemplated, mention should be made of those which are suitable to administration by mucosal, transcutaneous, topical, parenteral, digestive route or inhalation such as for instance coated or uncoated tablets, capsules, injection solutes or suspensions, spray, gels, plasters or rapid absorption solutes.

In preference, the compounds of the invention are administered by injection as aqueous solutions or suspensions, optionally neutralized by an amine or a hydroxyalkylamine.

The following non limiting examples further illustrate the invention. They are outlined in reaction schemes 1 to 6 (FIGS. 33–38).

EXAMPLE I 4-(diphenyloxyphosphoryloxy)-2-[(R)$_3$-dodecanoyloxytetradecanoylamino]butanoic acid

1. Nα-Terbutyloxycarbonyl-DL-homoserine 2 g of homoserine (16.78 mmol) were dissolved in 20 ml of water and to the solution 16.78 ml of 1 M NaOH and 3.006 g of cesium carbonate (9.23 mmol) were added. After stirring for 5 minutes, the solution was cooled in an ice/water bath. 60 ml of dioxane and terbutyl pyrocarbonate were then added. The reaction mixture was kept under stirring in an ice-cold water bath for 1 hour and thereafter at room temperature for 5 hours. The solvent was subsequently removed under vacuum. The dry residue was directly used in the next step.

2. Nα-Terbutyloxycarbonyl-benzyl-DL-homoserinate

To the residue of step 1, 20 ml of dimethylformamide were added and the solvent was evaporated to dryness then to the reaction mixture were added 60 ml of dimethylformamide and 4.5 ml of benzyl bromide (20.13 mmol). At this point, a white precipitate formed. The mixture was kept under stirring for 16 hours. The solvent was then driven away under vacuum. The residue was depleted or extracted twice with 20 ml of ethyl 10 acetate. The organic layer was respectively washed with water (20 ml) and with brine (20 ml), then dried on anhydrous magnesium sulfate. The solvent was evaporated and the residue was used as such in the next step.

3. benzyl Nα-Terbutyloxycarbonyl-O-(diphenyloxyphosphoryl)-DL-homoserinate

The residue of the previous step was dried under high vacuum then dissolved in methylene chloride (60 ml). 4,11 g of 4-dimethylaminopyridine (33.56 mmol) were then added to the solution, the reaction mixture was stirred for 10 minutes, and 12 ml of pyridine and 6.95 ml of chlorophosphate (33.56 mmol) were then added. The solution was stirred at room temperature for 18 hours then washed with 1N hydrochloric acid (5×20 ml), water (30 ml) and brine (30 ml). The organic layer was dried over anhydrous magnesium sulfate and the solvent was driven away under vacuum. The residue was purified by flash chromatography (hexane/ethyl acetate=4:1). The main fraction was concentrated to cristallize the residue. As a result, there was obtained 7,49 g of phosphorylated product, that is a yield of 82.4%. Melting point: 63.5–64.0° C.

4. Benzyl O-(diphenyloxyphosphoryl)-DL-homoserinate

The phosphorylated product of the previous step (7.88 g i.e 15.4 mmol) was dissolved in 15 ml of trifluoroacetic acid and the solution was kept under stirring at room temperature for 2.5 hours. The solvent was then driven away under vacuum, the residue was purified by flash chromatography (MeOH/CH$_2$Cl$_2$=10:1). The main fraction was concentrated and the residue was cristallized at room temperature. As a result, 7,17 g of phosphorylated product were recovered (88,9% yield). This was used in the next step with no further work-up.

5. Benzyl 2-[(R)-3-Dodecanovloxytetradecanovlamino]-4-(diphenyloxyphosphoryloxy)butanoate 4.284 g (10.07 mmol) of (R)3-dodecanoyloxytetradecanoic acid prepared acccording to the method disclosed in *Bull. Chem. Soc. Jpn.*, 60 (1987), 2205–2214, were dissolved in 30 ml of tetrahydrofurane and the solution was cooled down to −15° C. in an ice-cold brine bath. 1,108 ml (10.07 mmol) of N-methylmorpholin and 1.31 ml (10.07 mmol) of isobutyl chloroformate were then added. Stirring was continued for 30 minutes. To the reaction mixture, there was added 5.724 g (10.07 mmol) of benzyl O-(diphenyloxyphosphoryl)-DL-homoserinate in a mixture of 30 ml of tetrahydrofurane and 5 ml of triethylamine. After stirring overnight at room temperature, the solvent was driven away under vacuum and 20 ml of water were added to the residue. The mixture was then extracted with ethyl acetate (2×30 ml). The organic layers were pooled, washed in succession with water (20 ml) and brine (20 ml) and dried over magnesium sulfate. The solvent was evaporated and the residue was purified by flash chromatography (hexane-ethyl acetate 2:1, R$_f$=0.29); yield 7.455 g i.e 87.1% m.p. 31.0°–32.1° C., $^1$H-NMR (CDCl$_3$, 250 MHz), δ in ppm: 7.4–7.1 (m, 15H), 6.90 (2d, 1H, $^3$J=7.6 Hz, NH), 5.3–5.1 (m, 3H), 4.7 (m, 1H), 4.35 (m, 2H), 2.45 (m, 2H), 2.4–2.1 (m, 4H), 1.6 (m, 4H), 1.4–1.1 (m, 34H), 0.9 (t, 6H). $^{13}$C-NMR (CDCl$_3$, 63 MHz), δ in ppm: 173.01, 171.08, 169.66, 150.18, (d, $^2$J$_{P,C}$=7.1 Hz), 135.01, 129.60, 128.33, 128.14, 127.96, 125.21, 119.80 (d, $^3$J$_{P,C}$=5.0 Hz), 70.69, 67.05, 65.19 (d, $^2$J$_{P,C}$=5.6 Hz), 49.13, 40.97, 40.77 (2 diast.), 34.20, 33.98, 33.82, 31.70, 29.42, 29.34, 29.14, 28.94, 25.01, 24.47, 13.91.

6. 4-(diphenyloxyphosphoryloxy)-2-[(R)-3-dodecanoyloxytetradecanoylamino]-butanoic acid A solution was prepared from the benzyl ester obtained in step 5 (2.23 g i.e. 2.6 mmol) in 300 ml of HPLC-grade methanol in a three neck-round flask and then 1,0 g of carbon-10% palladium was added. Air contained in the round flask was discharged under vacuum, and the flask was loaded with hydrogen gas under atmospheric pressure.

The reaction mixture was stirred at room temperature for 1 hour, the catalyst was then quickly filtered off on a membrane and the filtrate was concentrated to obtain a colorless liquor. This product was homogeneous as assessed by thin layer chromatography and NMR, and was used directly with no further purification treatment in the coupling step; Rf=0.75 (dichloromethane-methanol-triethylamine, 10:1:0.5). $^1$H-RMN (CDCl$_3$, 250 MHz), δ in ppm: 7.4–7.1 (m, 10H), 6.85 (2d, 1H, NH), 5.15 (m, 1H), 4.6 (m, 1H), 4.35 (m, 2H), 2.45 (m, 2H), 2.4–2.15 (m, 4H), 1.6 (m, 4H), 1.4–1.1 (m, 34H), 0.9 (t, 6H). $^{13}$C-NMR (CDCl$_3$, 63 MHz), δ in ppm: 173.35, 171.30 (2 diast.), 172.75, 170.37, 150.0 (d, $^2$J$_{P,C}$=7.5 Hz), 129.55, 125.28, 119.71 (d, $^3$J$_{P,C}$=4.4 Hz), 70.78, 65.65, (d, $^2$J$_{P,C}$=5.9 Hz), 49.00, 40.77, 40.63 (2 diast.), 34.13, 33.86, 33.76, 31.59, 29.31, 29.25, 29.03, 28.82, 24.88, 24.68, 22.36, 13.76.

The 4-(diphenyloxyphosphoryloxy)-2-[(R)-3-benzyloxytetradecanoylamino]-butanoic acid can be prepared using the same reaction scheme by replacing in step 5 of example I, (R)-3-dodecanoyloxytetradecanoic acid by (R)-3-benzyloxytetradecanoic acid.

EXAMPLE II (2R)-5-amino-2-[(R)-3-benzyloxytetradecanoylamino]-pentan-1-ol

1. Copper Salt of D-ornithine

To a solution of D-ornithine (5.25 g i.e. 30 mmol) in 30 ml of 1M sodium hydroxide, 50 ml of a solution of cupric sulfate pentahydrate (3.814 g i.e. 15.3 mmol) in water were added. Stirring was continued for 2 hours. The solvent was evaporated to dryness. 60 ml of methanol were added to form a purple-colored solid which was separated, washed with dioxane and methanol, respectively.

2. copper (2R)-5-Amino-5-benzyloxycarbonylamino) pentanoate

The purple-colored solid was dissolved in 40 ml of 1M soda lye and 70 ml of dioxane, the solution was cooled in an ice-cold water bath and 5.14 ml (i.e. 36 mmol) of benzyl chloroformate were added. Stirring was continued in an ice-cold water bath for 3 hours and thereafter at room temperature for 15 hours. The purple precipitate was collected and washed with 95% ethanol (40 ml), with water (50 ml) and with ethanol (60 ml), respectively. The precipitate was dried in an oven (T<45° C., under vacuum); the yield of the two-step process was 8.27 g, i.e. 93% of the predicted yield.

3. (2R)-5-(benzyloxycarbonylamino)-2-(terbutyloxycarbonylamino)pentanoic acid

The copper salt obtained in step 2 was dissolved in 2M hydrochloric acid (400 ml) and EDTA was added (8.15 g, 27.8 mmol) thereto. The mixture was stirred for 2.5 hours, and neutralized to pH 7 by adding soda lye (about 160 ml). A white precipitate was formed. The mixture wa stirred for 2.5 hours in an ice-cold water bath. The precipitate was filtered, washed with cold water until washing effluents were colorless, then dried in an oven under 60° C. This solid was dissolved in 156 ml of 1M NaOH and the solution was cooled with an ice-cold water bath. To this solution, 7,7 g (35.2 mmol) of terbutyl pyrocarbonate in dioxane (160 ml) were added. The mixture was stirred at 0° C. for 45 minutes then for 16 hours at room temperature. The organic solvent was evaporated and 70 ml of ethyl acetate were added to the residue. The aqueous layer was acidified by adding 2N hydrochloric acid down to pH ≈3. The aqueous layer was extracted once again with 100 ml of ethyl acetate. The organic layers were combined and washed with water (30 ml) and with brine (30 ml). The solvent was removed under vacuum to therby provide a colorless oil after flash chromatography purification (yield: 8.42 g in 2 steps i.e. 76.7% of the predicted yield) (Rf=0.19, dichloroethane-MeOH 20:1).

4. (2R)-5-(Benzyloxycarbonylamino)-2-(terbutyloxycarbonylamino)pentan-1 ol

To a cold solution (−15° C.) of the diamino pentanoic acid derivative obtained in step 3 (5.45 g i.e. 14.8 mmol) in 60 ml of THF, 1.654 ml (i.e. 14.8 mmol) of N-methylmorpholin and 9.6 ml (i.e. 14.8 mmol) of isobutyl chloroformate (IBCF) were added. The solution was stirred at −15° C. for 1 minute followed by addition of sodium borohydride (5.104 g i.e. 44.6 mmol) in 10 ml of water. The stirring was conducted at −15° C. for further 10 minutes then 400 ml of water were added to stop the reaction. The solution was extracted with ethyl acetate (100 ml×2). The organic layers were combined and washed with 50 ml of water and with 60 ml of brine then dried over anhydrous magnesium sulfate. The solvent was removed and the residue recristallized from an ethyl acetate/hexane mixture (4.95 g, 94.9% yield) m.p. 47.5–48° C.

5. Unblocking of the 2,5-diaminopentan-1-ol derivative 6.32 g (18 mmol) of (2R)-5-(benzyloxycarbonylamino)-2-(terbutyloxycarbonylamino)-pentan-1-ol obtained in step 4 were dissolved in 25 ml of trifluoroacetic acid followed by stirring the solution for 2.5 hours at room temperature. The solvent was then evaporated and the residue was purified by running flash chromatrography (MeOH/CH$_2$Cl$_2$=10:1). A colorless vitreous bulk product was obtained as a result which melts at room temperature. Yield was 5.45 g in terms of trifluoroacetic salt (yield=82.7%). The hydrochloride compound melts at 133.0°–134.3° C. (recristallization from methanol).

6. (2R)-5-(Benzyloxycarbonylamino)-2-[(R)-3-benzyloxytetradecanoylamino]pentan-1-ol To a previously cooled solution to −15° C., 5.27 g (15.8 mmol) of (R)-3-benzyloxytetradecanoic acid (*Bull. Chem. Soc., Jpn.*, 60 (1987), 2197–2204) in 30 ml of tetrahydrofuran, 1.89 ml (15.8 mmol) of N-methylmorpholin and 2.21 ml of IBCF (15.8 mmol) were added. The reaction mixture was kept under stirring at −15° C. for 30 minutes. Then, 5.25 g of trifluoroacetate salt of the preceding example (14.4 mmol) in 30 ml of tetrahydrofuran and 1.44 ml of triethylamine were added to the solution. Stirring was continued at room temperature for 16 hours then 30 ml of water and 60 ml of ethyl acetate were added; the organic layer was separated and the aqueous layer was extracted once again with ethyl acetate (60 ml). The organic layers were pooled and washed with water (30 ml) and with brine (30 ml) then dried over anhydrous magnesium sulfate. The solvent was evaporated and the residue was recristallized from an ethyl acetate/hexane mixture (5.842 g, i.e. 71.2% yield), m.p.=117.5–118° C. Rf=0.32, ethyl acetate-petroleum ether 3:1. $^1$H-NMR (CDCl$_3$, 250 MHz), δ in ppm: 7.4–7.2 (m, 10H), 6.5 (2d, 1H, NH), 5.1 (s, 2H), 4.9 (m, 1H, NH), 4.5 (2d, AB, 2H), 3.8 (m, 2H), 3.5 (m, 2H), 3.1 (m, 2H), 2.4 (m, 2H), 2.4 (m, 2H), 1.6–1.4 (m, 6H), 1.4–1.2 (m, 18H), 0.9 (t, 3H). $^{13}$C-NMR (CDCl$_3$, 63 MHz), δ in ppm: 172.24, 156.49, 138.06, 136.53, 128.46, 128.04, 127.87, 76.76, 71.39, 66.60, 65.44, 51.54, 41.43, 40.65, 33.76, 31.87, 29.61, 29.30, 28.01, 26.47, 25.05, 22.65, 14.09.

7. (2R)-5-Amino-2-[(R)-3-benzyloxytetradecanoylamino]pentan-1-ol

In a three neck-flask, 150 mg of 20% palladium/carbon were added to the solution of (2R)-5-(Benzyloxycarbonylamino)-2-[(R)-3-benzyloxytetradecanoylamino]pentan-1-ol (3.0 g, i.e. 5.27 mmol) and 6 ml of triethylamine in 300 ml of HPLC-grade ethanol, Air was discharged under vacuum then the flask was loaded with hydrogen. The reaction mixture was stirred at room temperature for 2 hours then the catalyst was filtered off by membrane filtration and the filtrate was concentrated to provide a homogenous white solid as shown by TLC, to be used as such in the next step with no further purifcation, Rf=0.2, dichlormethane-methanol-triethylamine 5:10.5, m.p.=47–48° C.

$^1$H-NMR (CDCl$_3$, 250 MHz), δ in ppm: 7.4–7.2 (m, 5H), 6.75 (d, 1H, NH) 4.5 (2d, AB, 2H), 3.9 (m, 2H), 3.5 (m, 2H), 2.3–2.6 (m, 7H), 1.7–1.2 (m, 24H), 0.9 (t, 3H). $^{13}$C-NMR (CDCl$_3$, 63 MHz), δ in ppm: 171.86, 138.13, 128.37, 127.87, 127.75, 76.81, 71.50, 64.57, 51.38, 41.51, 41.17, 33.89, 31.82, 29.26, 28.57, 28.03, 25.07, 22.60, 14.04.

(2R)-5-amino-2-[(R)-3-dodecanoyloxytetradecanoylamino]pentan-1-ol can be obtained according to the same reaction scheme by replacing in step 6 of example II, (R)-3-benzyloxytetradecanoic acid by (R)-3-dodecanoyloxytetradecanoic acid.

EXAMPLE III

3-[(R)-3-dodecanoyloxytetradecanoylamino]-4-oxo-5-aza-9-[(R)-3-hydroxytetradecanoylamino]-decane-1,10-diol 1-dihydrogenphosphate 1. Peptide Coupling In a solution of (2RS)-4-(diphenyloxyphosphoryloxy)-2-[(R)-3-dodecanoyloxytetradecanoylamino]butanoic acid (1.0 mmol) as obtained in Example I, dissolved in 20 ml of methylene chloride, 363.6 mg (1.2 mmol) of IDQ (1-isobutyloxy-2-isobutyloxycarbonyl-1,2-dihydroquinoline) are suspended. After stirring for 15 minutes, addition is made of 1.0 mmol of (2R)-5-amino-2-[(R)-benzyloxytetradecanoylamino]pentan-1-ol from Example II, being dissolved in 10 ml of methylene chloride and the reaction mixture is kept under stirring for 4 hr.

The solution is concentrated and the residue is purified by a flash chromatography treatment (CH$_2$Cl$_2$/acetone=5:2, Rf 0.23). The solvent is removed thus obtaining a colorless thick liquor (0.620 g i.e. 52.7% yield) of a phosphorylated dipeptide-like compound. Rf=0.49, dichloromethane-methanol-triethylamine, 10:1:0.5. $^1$H-NMR (CDCl$_3$, 250 MHz), δ in ppm: 7.40–7.15 (m, 15), 7.00 (m, 1H), 6.90 and 6.80 (2d, 2 diast., 1H), 6.65 (d, 1H) (3×NH), 5.15 (m, 1H), 4.50 (m, 3H), 4.30 (m, 2H), 3.85 (m, 2H), 3.45 (m, 2H), 3.15 (m, 2H), 2.41–2.14 (m, 8H), 1.6–1.4 (m, 8H), 1.4–1.1 (m, 54H), 0.9 (t, 9H, 3CH$_3$). $^{13}$C-NMR (CDCl$_3$, 63 MHz), δ in ppm: 173.11, 171.68, 170.52 (2 diast.), 169.94 (2 diast), 150.0 (d, JPC=7.2 Hz), 138.0 (2 diast.), 129.58, 127.99, 127.49, 127.26, 125.24, 119.73 (t, JPC=5.0 Hz), 76.48, 71.12, 70.71, 65.86 (broad spin), 64.22, 50.96, 49.71 (broad spin), 41.46, 41.05, 39.07, 34.13, 34.00, 32.70, 31.61, 29.34, 29.06, 28.87, 27.98, 25.25, 24.92, 24.72, 22.38, 13.80.

2. 1-(Diphenyloxyphosphoryloxy)-3-[(R)-3-dodecanoyloxytetradecanoylamino]-4-oxo-5-aza-9-[(R)-3-hydroxytetradecanoylamino]decan-10-ol The phosphorylated dipeptide-like compound solution (488 mg i.e. 0.42 mmol) obtained above and acetic acid (1.9 ml) in 65 ml of HPLC-grade ethanol were introduced in a three-neck round flask and 200 mg of palladium on carbon containing 10% Pd were added. Air was discharged under vacuum and the flask was loaded with hydrogen. The reaction mixture was stirred at room temperature for 2 hr., then the catalyst was filtered off by membrane filtration, the solvent was driven away under vacuum, to thereby recover the crude product with a yield of 92%. A sample of the product was purified by flash chromatography (CH$_2$Cl$_2$/acetone 5:4, Rf=0.24). As a result, a glass-like solid was obtained. Rf=0.68, 5:2 methylene chloride-methanol. ($^{13}$C-NMR (CDCl$_3$, 63 MHz), δ in ppm (a few signals in doublet form due to the presence of diastereoisomers were observed): 173.60, 173.15, 170.67, 170.60, 170.27, 170.07, 150.24 (d), 129.92, 125.66, 120.05, 119.90 (2d), 71.11, 71.05, 68.83; 66.21 (broad spin), 64.71, 51.38; 50.32, 50.12, 43.25, 43.12, 41.66, 41.57, 39, 30, 37.26, 34.45, 32.84, 31.86, 29.62, 29.5, 29.29, 29.13, 28.08, 25.57, 25.19, 24.97, 22.62, 14.03.

3. 3-[(R)-3-Dodecanoyloxytetradecanoylamino-4-oxo-5-aza-9-[(R)-3-hydroxytetradecanoylamino] decan-1,10-diol 1-dihydrogenphosphate In a three-neck round flask, platinium oxide (137 mg) was preactivated with hydrogen in absolute ethanol (5 ml) for 10 min. Addition was then made of a solution of 1-(diphenyloxyphosphoryloxy)-3-[(R)-3-dodcanoyloxytetradecanoylamino]-4-oxo-5-aza-9-[(R)-3-hydroxytetradecanoylamino) decan-10-ol (411 mg i.e. 0.38 mmol) in absolute ethanol (20 ml). Air was discharged under high vacuum, and the flask was then loaded with hydrogen. The reaction mixture was stirred at room temperature for 2–3 hr., the catalyst was filtered off by membrane filtration, and finally the solvent was driven away under vacuum. As a result, a crude product in the form of a white solid was finally obtained. (crude product yield: 98%). Rf=0.50, chloroform-methanol-water, 6:4:0.6.

3-[(R)-3-hydroxytetradecanoylamino]4-oxo-5-aza-9-[(R)-3-dodecanoyloxytetradecanoylamino]-decan-1,10-diol 1-dihydrogenphosphate can be obtained starting from 4-(diphenyloxyphosphoryloxy)-2-[(R)-3-benzyloxytetradecanoylamino]butanoic acid and (2R)-5-amino-2-[(R)-3-dodecanoyloxytetradecanoylamino]pentan-1-ol according to the same reaction scheme (scheme 3) (FIG. 35).

Alternatively, 3-[(R)-3-dodecanoyloxytetradecanoylamino]-4-oxo-5-aza-9-[(R)-3-hydroxytetradecanoylamino]-decan-1,10-diol 1-dihydrogenphosphate is obtained starting from aspartic acid according to the following reaction scheme (reaction schemes 1, 5 and 6) (FIGS. 33, 37 and 38): protecting the free OH functional group of (2R)-5-(benzyloxycarbonylamino)-2-[(R)-3-benzyloxytetradecanoylamino]pentan-1-ol by a benzyloxymethyl group, freeing the 5-amino functional group of this compound by hydrogenolysis, effecting peptide coupling of this amine with a monoesterified derivative of D or L-aspartic acid bearing at the amine functionality thereof either a protecting group or an (R)-3-dodecanoyloxytetradecanoyl group, freeing and reducing the terminal carboxylic functional group by means of a mixed anhydride, deprotecting, if needed, the amine functional group derived from aspartic acid then N-acylating with an (R)-3-dodecanoyloxytetradecanoic acid derivative, phosphorylating the hydroxy functional group at C$_1$ and finally unblocking the phosphate and hydroxyl functional groups through hydrogenolysis.

EXAMPLE IV

Preparation of 3-[(R)-3-dodecanoyloxytetradecanoylamino]-4-oxo-5-aza-9-[(R)-3-hydroxytetradecanoylamino]decan-1,10-diol 1, 10-bis(dihydrogenphosphate)

1-(diphenyloxyphosphoryloxy)-3-[(R)-3-dodecanoyloxytetradecanoylamino]-4-oxo-5-aza-9-[(R)-3-benzyloxytetradecanoylamino]decan-10-ol (985 mg i.e. 0.84 mmol) is reacted with dibenzyl N,N'-diethylphosphoramidite (0.58 ml, 85% pure), in presence of [1H]-tetrazole (182 mg) in tetrahydrofurane (35 ml) for 30 minutes at room temperature. The phosphite intermediate is oxidized by addition of a solution of m-chloroperoxybenzoic acid (535 mg) in 25 ml of methylene chloride at a temperature range of 0° to −20° C. After 20 min., a solution of $Na_2S_2O_3$ (20 ml) is added to neutralize any excess oxydant, then the organic layer is diluted with ether. The organic layer is separated, washed in succession with an aqueous solution of $Na_2S_2O_3$ (5×20 ml), then a solution of $NaHCO_3$ (2×20 ml), thereafter with aqueous hydrochloric acid (20 ml), dried over $MgSO_4$ and concentrated. The crude product is purified by flash chromatography treatment over a silica gel ($CH_2Cl_2$-acetone 10:3). The protected diphosphorylated derivative thus obtained (900 mg, 75% yield) (Rf 0.64, 5:2 dichloromethane-acetone) is subjected to a catalytic hydrogenation in HPLC-grade methanol (1000 ml) in presence of 10% palladium-carbon (300 mg) under atmospheric pressure, for 4 hr. at room temperature. The catalyst is filtered off by membrane filtration and the filtrate is concentrated under reduced pressure, to thereby recover crude 10-(dihydroxyphosphoryloxy)-1-(diphenyloxyphosphoryloxy)-3-[(R)-3-dodecanoyloxytetradecanoylamino]-4-oxo-5-aza-[(R)-3-hydroxytetradecanoylamino]decane (Rf=0.63, chloroform-methanol-water 6:4:0.6) with a yield of 89%. This product is then submitted to a catalytic hydrogenation on platinium oxide (380 mg) in HPLC-grade ethanol (130 ml) for 24 hr. at room temperature, under atmospheric pressure. The catalyst is filtered off by membrane filtration and the filtrate is concentrated to thereby obtain the free bis dihydrogenophosphate compound (Rf=0.20, chloroform-MeOH-water, 6:4: 0.6).

3-[(R)-3-hydroxytetradecanoylamino]-4-oxo-5-aza-9-[(R)-3-dodecanoyloxytetradecanoylamino]-decan-1,10-diol 1,10-bis(dihydrogenphosphate) can be obtained starting from 4-(diphenyloxyphosphoryloxy)-2-[(R)-benzyloxytetradecanoylamino]butanoic acid and (2R)-5-amino-2-[(R)-3-dodecanoyloxytetradecanoylamino]pentan-1-ol according to the same reaction scheme (scheme 3) (FIG. 35).

Alternatively, 3-[(R)-3-dodecanoyloxytetradecanoylamino]-4-oxo-5-aza-9-[(R)-3-hydroxytetradecanoylamino]decan-1,10-diol 1, 10-bis(dihydrogenphosphate) is obtained starting from aspartic acid using the following reaction scheme (reaction schemes 1, 4 and 6): freeing the 5-amino functional group of (2R)-5-(benzyloxycarbonylamino)-2-[(R)-3-benzyloxytetradecanoylamino]pentan-1-ol by hydrogenolysis, performing peptide coupling of this amine with a monoesterified derivative of D or L-aspartic acid bearing at the amine functionality thereof either a protecting group or a (R)-3-dodecanoyloxytetradecanoyl group, freeing and reducing the terminal carboxylic functional group by means of a mixed anhydride, deprotecting, if needed, the amine functional group derived from aspartic acid then N-acylating with an (R)-3-dodecanoyloxytetradecanoic acid derivative, phosphorylating the hydroxy functional group at $C_1$ and $C_{10}$ and finally unblocking the phosphate and hydroxyl functional groups through hydrogenolysis.

EXAMPLE V

Purification and Analysis of Compounds According to the Invention

1. Purification of Monophosphorylated and Diphoshorylated Compounds

The monophosphorylated and diphosphorylated synthetic products were dissolved in a water-isopropanol mixture (1:1 vol./vol.) with 0.1% triethylamine to ajust the pH in the range of 8 to 9. The required amount of 2 M ammonium bicarbonate was subsequently added to achieve a concentration of 25 mM.

The purification was run by preparative reverse phase HPLC under the following conditions:

Column: Bondapack C18 Prep Pak, 40×200 mm, 15–20 µm, 300 Å, Waters

Mobile phase:

A: isopropanol-water (1:1, vol./vol.), 50 mM ammonium bicarbonate

B: isopropanol-water (2:8, vol./vol.), 50 mM ammonium bicarbonate

Flow rate: 40 ml/min.

Elution: Isocratic adsorption onto column: 40% B (60% A), 10 minutes.

A: B gradient: 40–80% B within 10 minutes

Isocratic elution: 80% B, 30 minutes

Washing step: 100% B, 10 minutes

Detection: UV, 210 nm (wavelength)

In the aforementioned eluting conditions, the retention time of the monophosphorylated compound varies from 25 to 30 min while that for the diphosphorylated compound varies from 18 to 25 minutes. Should the presence of monophenyl-products be observed (incomplete deprotection treatment during final dephenylation), a finer purification step is required. This further purification is performed in the following conditions:

Column: Kromasil C18, 21×250 mm, 5 µm, 100 Å, Macherey-Nagel

Mobile phase:

A: isopropanol-water (1:1-v/v), 50 mM ammonium bicarbonate.

B: isopropanol-water (2:8, v/v), 50 mM ammonium bicarbonate

Flow rate: 10 ml/min.

Elution: Isocratic adsorption onto column: 40% B (60% A), 10 minutes

Isocratic elution:

monophosphorylated compound: 80% B, 30 minutes diphosphorylated compound: 74% B, 30 minutes Washing step: 100% B, 10 minutes Detection: UV; 210 and 254 nm (wavelength)

Fractions containing the monophosporylated or diphosphorylated compounds in the form of an ammonium salt are collected and concentrated by adsorption on C18 phase Bondapack, 15–20 µm, 300 Å, Waters, The sodium salt of monophosphorylated or diphosphorylated compounds is obtained through washing with a 10 g/l NaCl solution in water-isopropanol (9:1, v:v). After removal of excess NaCl by flowing over the column 5 volumes of a water-isopropanol mixture (9:1, v/v), the compound is eluted with pure isopropanol. This solvent is then evaporated to dryness on a Rotavapor. Final dissolution is conducted with the required volume of water (with adjunction of 0,1% triethanolamine in case of a monophosphorylated compound) to achieve a target concentration of 2 mg/ml. Sterile filtration is then performed on a 0,2 µm filter, Express Membrane, Millipore (if volume is less than 50 ml: the Steriflip system is recommended, if volume greater than 50 ml: the Steritop system is recommended).

In handling a monophosphorylated compound, it is advisable to sonicate the solution (3×10 seconds) at room temperature before running sterile filtration.

2. Monitoring and Yield of Purification

After termination of each step, the fractions are analyzed by reverse phase analytic HPLC chromatography according to the following conditions:

Column: Supelcosil C18, 3 µm, 4.6×150 mm, 100 Å, Supelco

Mobile phase:
A: water:acetonitrile (1:1, v/v), 5 mM TBAP
B: water-isopropanol (1:9, v/v) 5 mM TBAP
TBAP: tetrabutylammonium phosphate
Flow rate: 1 ml/min.
Elution: A: B gradient (75:25–0:100) within 37.5 minutes.
Detection: UV, 210 and 254 nm (wavelength)

When chromatography is conducted accordingly, the retention times observed for mono- and diphosphorylated compounds are 25.5±0.5 and 20.8±0.5 minutes, respectively. The purification yields achieved range from 57 to 94% for the monophosphorylated compound and from 71 to 92% for the diphosphorylated compound. 311 mg and 189 mg of mono- and diphosphorylated compounds are obtained, respectively.

3. Assay and Analysis of the Final Product Purity Level

Quantitative assays and purity level analysis of the products obtained were conducted by HPLC/UV according to the chromatography operating conditions stated previously. According to such assays, the purity levels obtained for different batches of mono- and diphosphorylated compounds vary from 99 to 100%. To show the presence of inactive impurities in the UV range, LC/ES-MS analysis were conducted (electrospray type ionization, positive mode). For the latter, the (5 mM) tetrabutylammonium phosphate was replaced by (25 mM) ammonium acetate to meet the requirements of ionization at the electrospray interface.

Alternative determination methods were used to assay the final solutions. For example, quantitative analysis of total phosphates (adapted from Ames, B. N., *Methods in Enzymology* VII (1966), 115–117), amino acids (adapted from Hughes et al., *J. Chromatography*, 389: (1987), 327–333) and acyl chains (adapted from Miller, L. T., Hewlett Packard Application Note (1984), 228–237) can be listed.

4. Spectroscopic Analysis 4.1. Mass Spectrometry

ES-MS spectra (negative and positive modes) of mono- and diphosphorylated compounds were plotted using three types of mass spectrometers. (Finnigan LCQ, ion trap; Micromass Quattro II, triple stage quadrupole; Hewlett-Packard MSD, single quadrupole). Complementary MS/MS analysis were also conducted. Spectra demonstrating the identity and purity of said products are included in the appendix.

ES-MS Spectra (positive mode)

Figure 39:
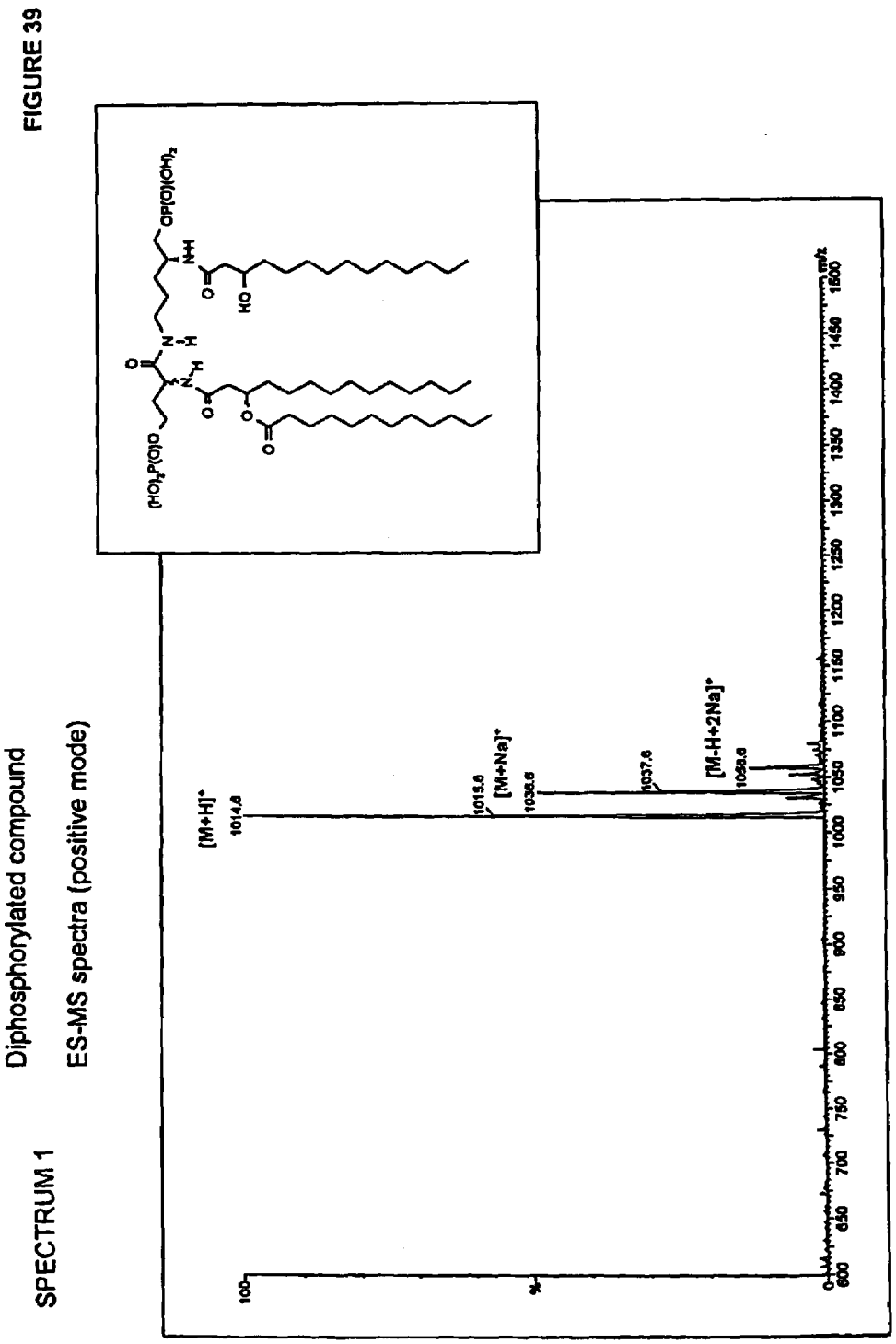
FIGS. 39 to 41 are Mass spectra of the compounds of the invention.
Figure 41:
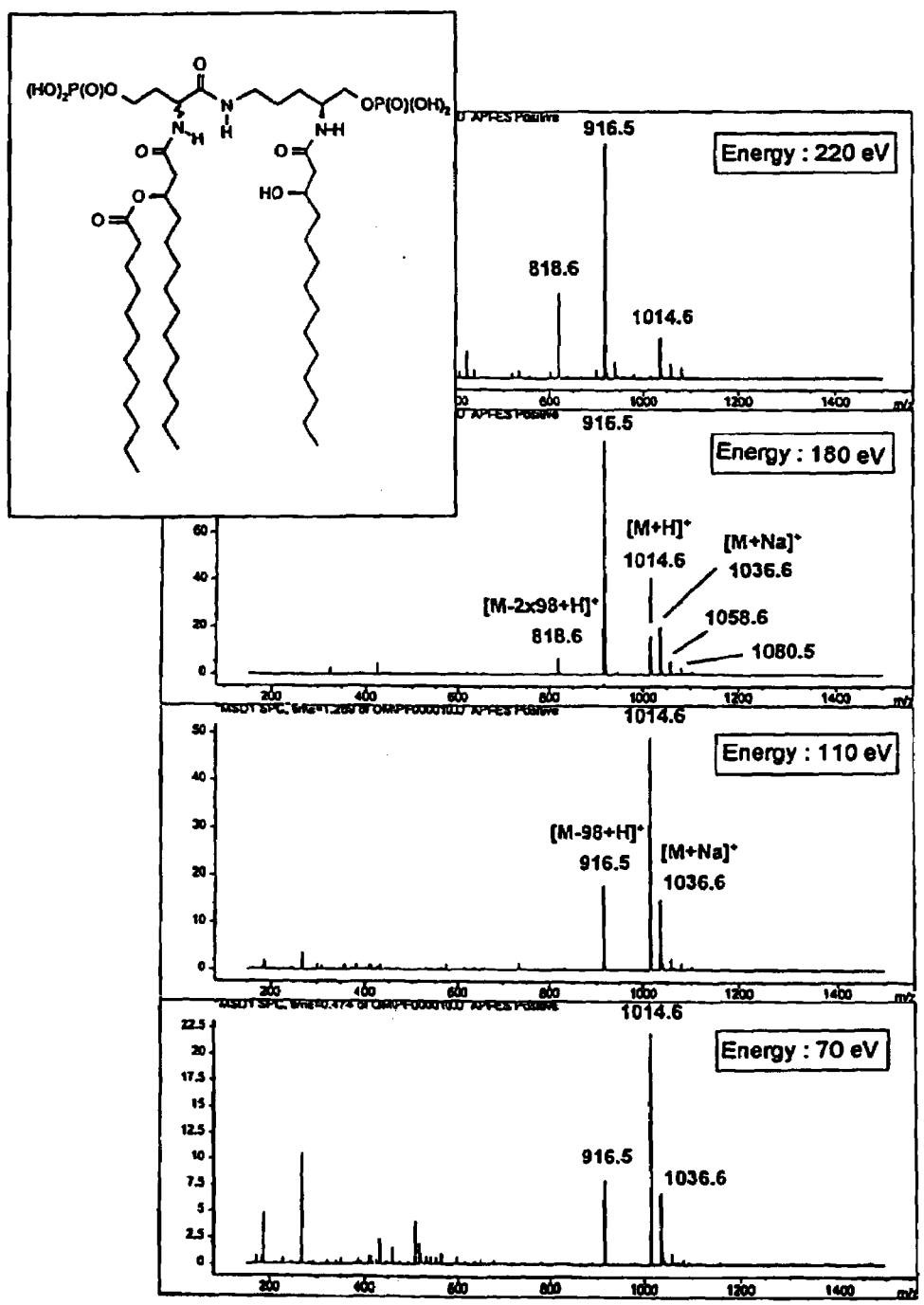

Diphosphorylated compound:

(Micromass Quattro II: Spectrum 1; HP-MSD: Spectrum 3) (FIGS. 39 & 41)

At low energy level, a major pseudomolecular ion is observed at an m/z ratio of 1014.6 $[M+H]^+$. Sodium adducts at an m/z ratio of 1036.6 $[M+Na]^+$, 1058.6 $[M-H+2Na]+$ and at 1080.5 $[M-2H+3Na]^+$ are also visible.

Depending on the degree of fragmentation, two 916.5 $[M-98+H]^+$ and 818.6 $[M-98-H]^+$ m/z fragments are observed, a fact which demonstrates the presence of two phosphoryl group on the molecule. As depicted by spectrum 3 (FIG. 41), the relative intensity of observed ions varies considerably according to the extent of energy level being applied.

Figure 40:
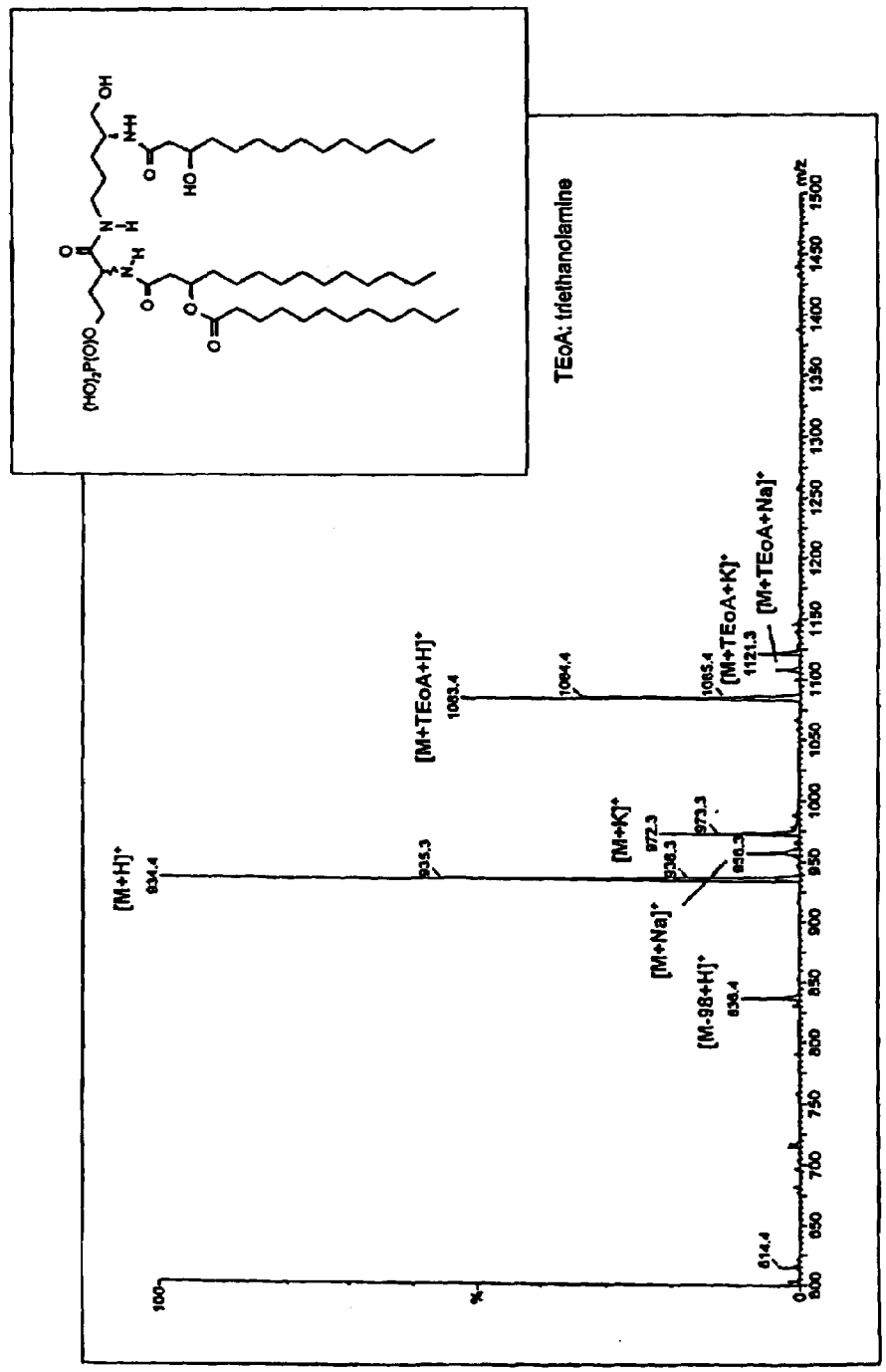

Monophosphorylated compound:

(Micromass Quattro II: Spectrum 2) (FIG. 40)

A somewhat different ionization diagram is obtained for the monophosphorylated compound due to the presence of triethanolamine (TEoA) in the solutions being analyzed. A major pseudomolecular ion is observed at an m/z ratio of 934.4 $[M+H]^+$ as well as sodium adducts $[M+H]^+$ and potassium adducts $[M+K]^+$ at an m/z ratio of 956.3 and 972.3, respectively. A second group of adducts at an m/z ratio of 1083.4 $[M+TEA+H]^+$, an m/z ratio of 1105.3 $[M+TeOH+Na]$ and an m/z ratio of 1121.3 $[M+TeOH+K]^+$ is equally visible. The presence of a phosphoryl group inside the molecule is evidenced by a fragment being detected at high energy level corresponding to an m/z ratio of 836.4 $[M-98+H]^+$.

ES-MS Spectra (negative mode)

Ion species observed in negative mode ES-MS spectra for mono- and diphosphorylated compounds are quite in agreement with results obtained in the positive mode.

FAB ionization analysis (positive mode) were also conducted. At low resolution level, the mono- and diphosphorylated compounds show sodium adducts $[M+Na]^+$ at 956.5 and 1036.5 m/z ratio, respectively.

At high resolution level (3-nitro benyl alcohol matrix), a peak was observed at an m/z ratio of 956.667 for the the monophosphate compound, corresponding to the expected molecular formula: $C_{49}H_{69}O_{11}N_3PNa$ (predicted mass: 956.668 amu).

For the diphosphated compound, a peak at an m/z ratio of 1036.635 was recorded, corresponding to the expected molecular formula $C_{49}H_{97}O_{14}N_3P_2Na$ (calculated mass: 1036.634 amu).

All MS analysis provided evidence of the high purity level of the obtained products.

4.2 Nuclear Magnetic Resonance $^1$H-NMR and $^{13}$C-NMR spectra for mono- and diphosphorylated compounds were determined using a DPX Brucker model apparatus operating at 250.13 and 62.89 MHz, respectively, and a Varian Unity Inova system operating at 500–499.87 and 125.7 MHz, respectively. $^{31}$P-RMN spectra were recorded at 121.6 mHz (DPX Brucker). Spectra showing the identity and purity of the these products are included in the appendix.

Figure 43:
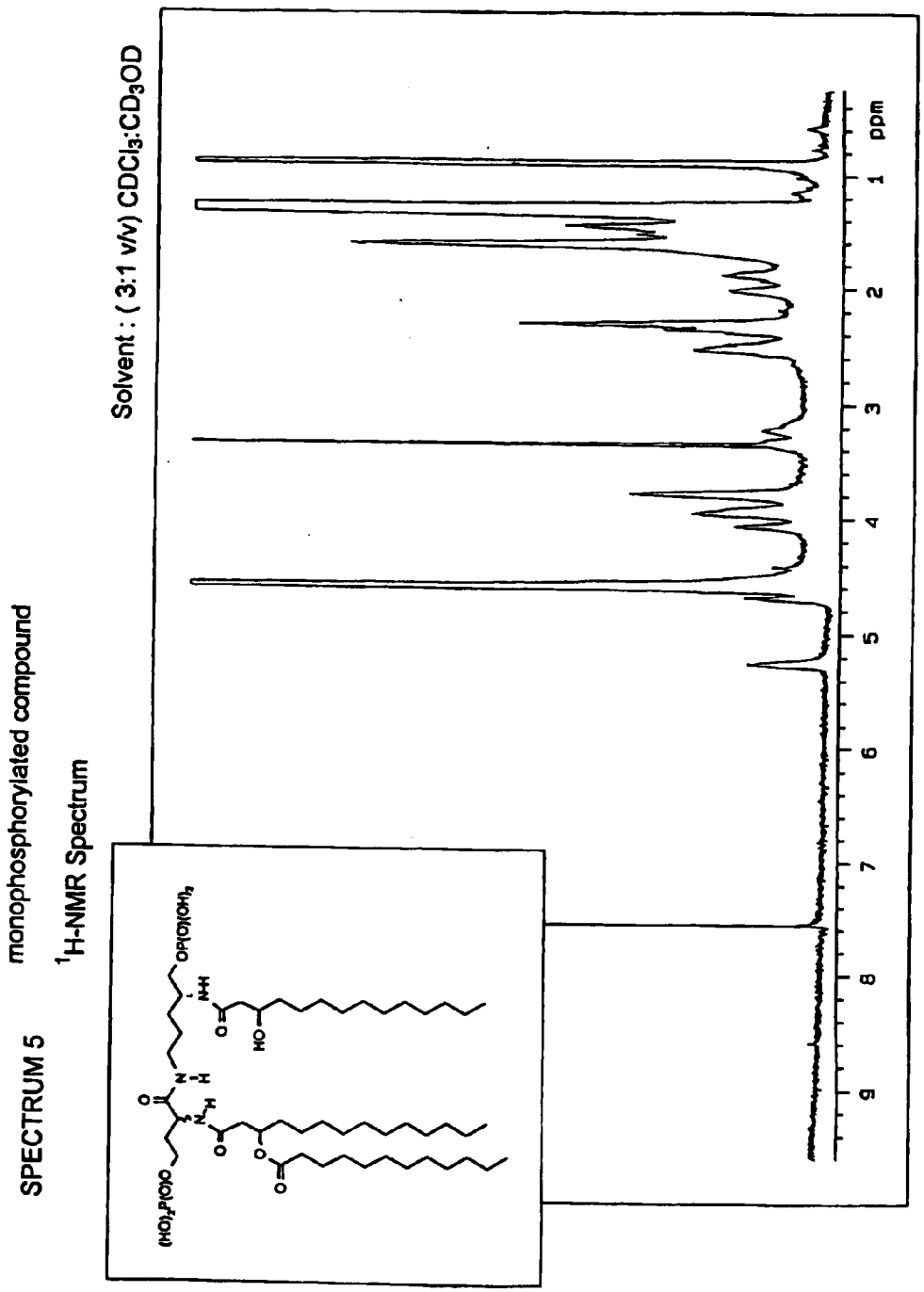

$^1$H-NMR Spectra (Spectra 4 & 5) (FIGS. 42 & 43)

Monophosphorylated compound: On spectra recorded in CDCl$_3$+0.1% triethanolamine (TEoA) (Spectrum A), signals corresponding to three protons born by nitrogen atoms N(5), N(2a) and N(2b) between 7 and 9.5 ppm (see magnified view of the spectral window) were observed. Signals ascribed to H—N(2a) and H—N(2b) appear in the form of 2 doublets which show the presence of a mixture of stereoisomers. One of the diastereoisomers is observed to be prevailing (as a result of the different purification steps).

Diphosphorylated compound: On the spectrum recorded in CDCl$_3$—CD$_3$OD (3:1, v/v) (Spectrum 5), signals corresponding to H—N(5), H—. N(2a) and H—N(2b) are no longer visible as a result of species exchange in presence of CD$_3$OD.

Additional information regarding the assignment of differents signals were gained from homo- and heteronuclear correlation experiments ($^1$H-$^1$H-NMR: COSY, $^1$H-$^{13}$C-NMR: HSQC & HMBC).

Figure 44:
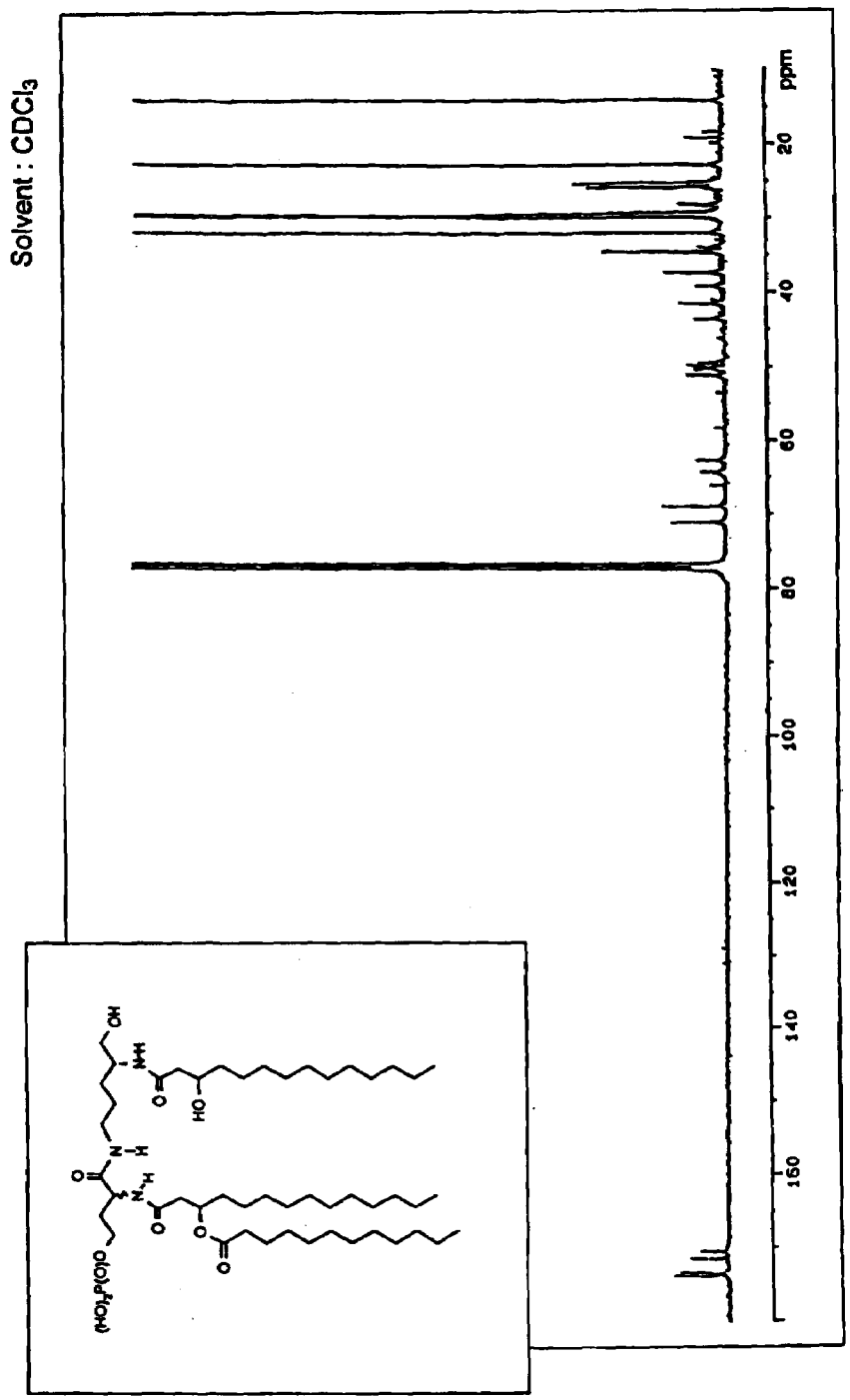
FIGS. 44 and 45 are $^{13}$C-NMR spectra of the compounds of the invention.
Figure 45:
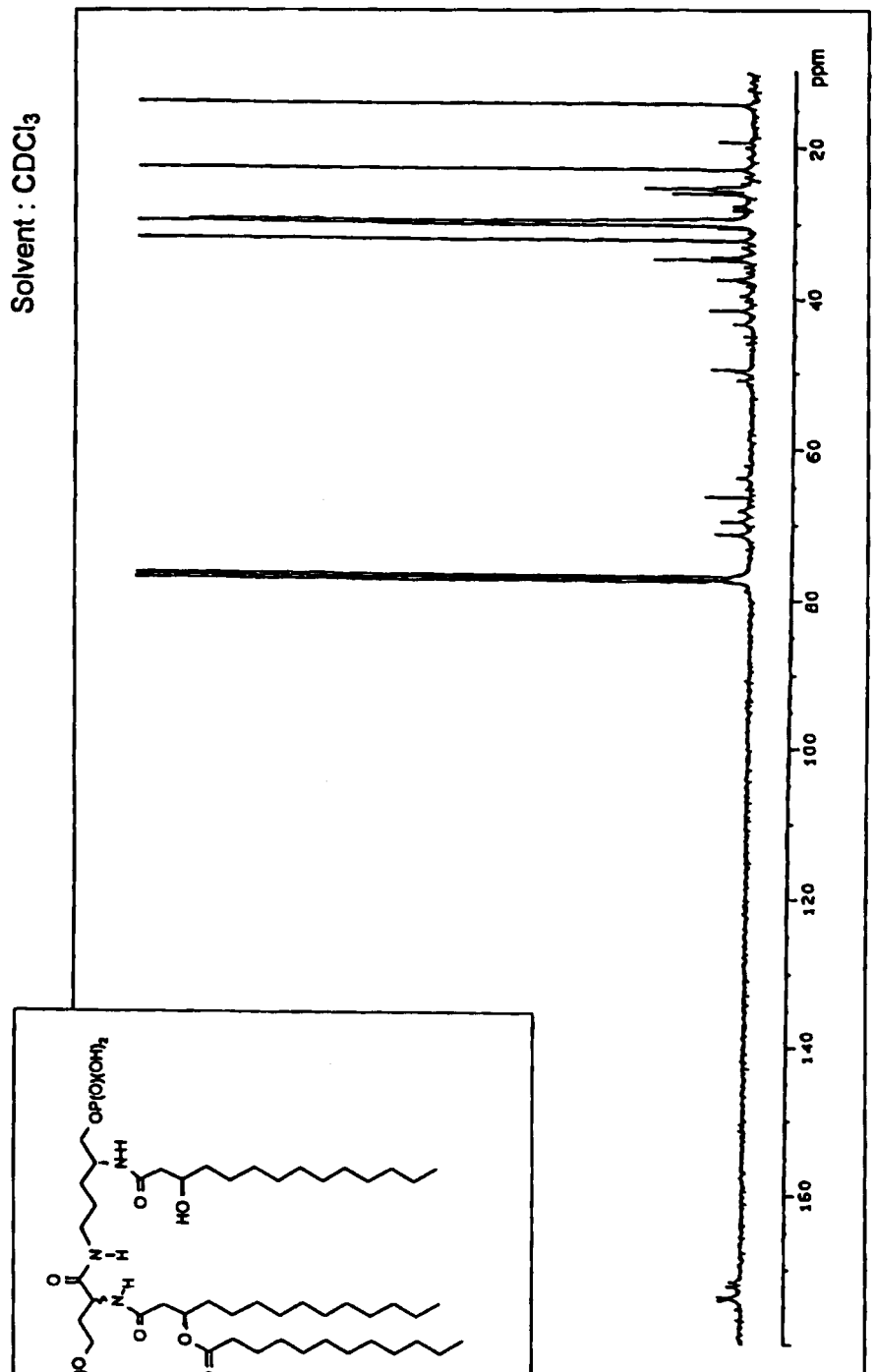

$^{13}$C-NMR Spectra (Spectra 6 & 7) (FIGS. 44 & 45)

Recording of $^{13}$C-NMR spectra is extremely difficult to carry out due to the rather low solubility of mono- and diphosphorylated compounds.

Figure 46:
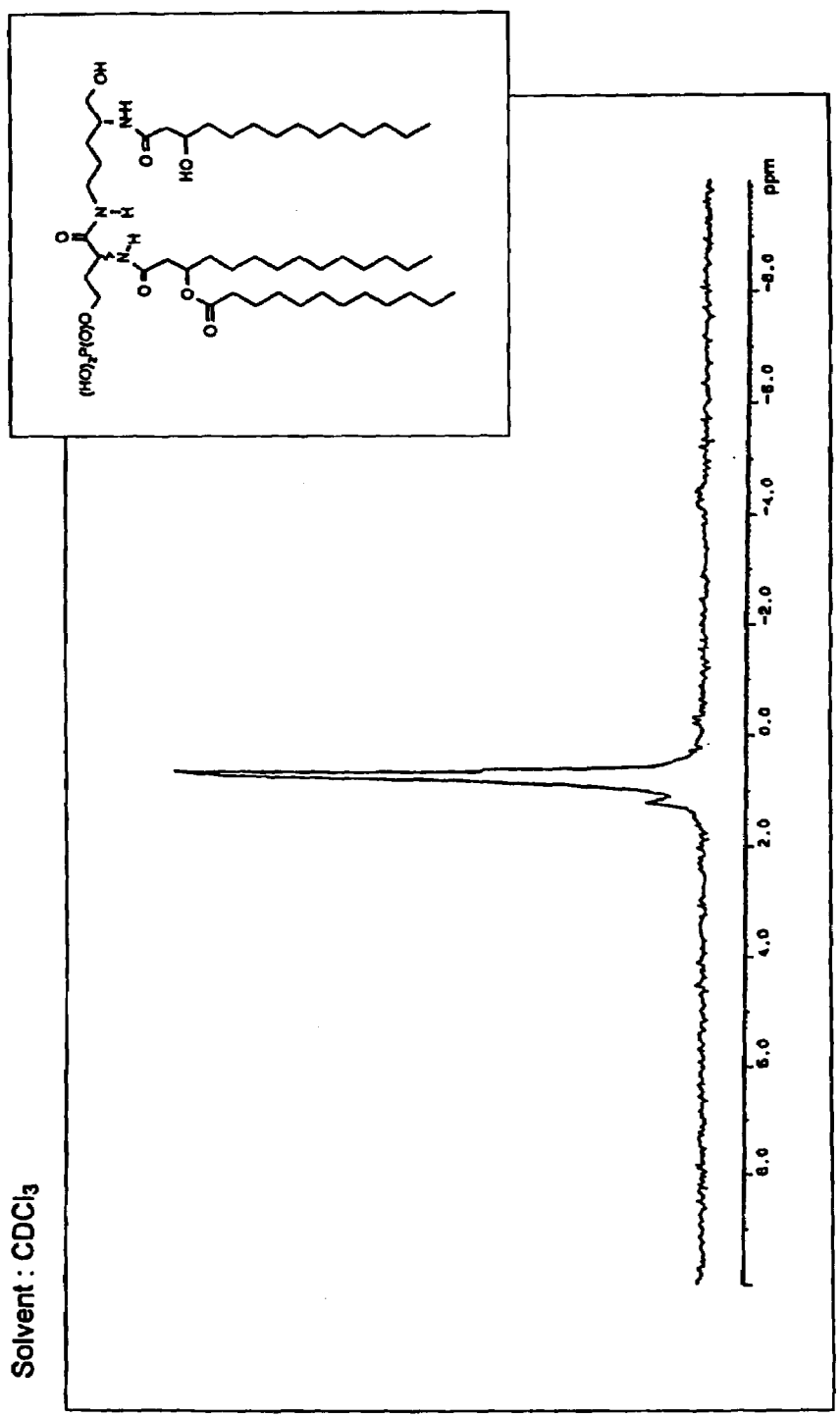
FIGS. 46 and 47 are $^{31}$P-NMR spectra of the compounds of the invention.
Figure 47:
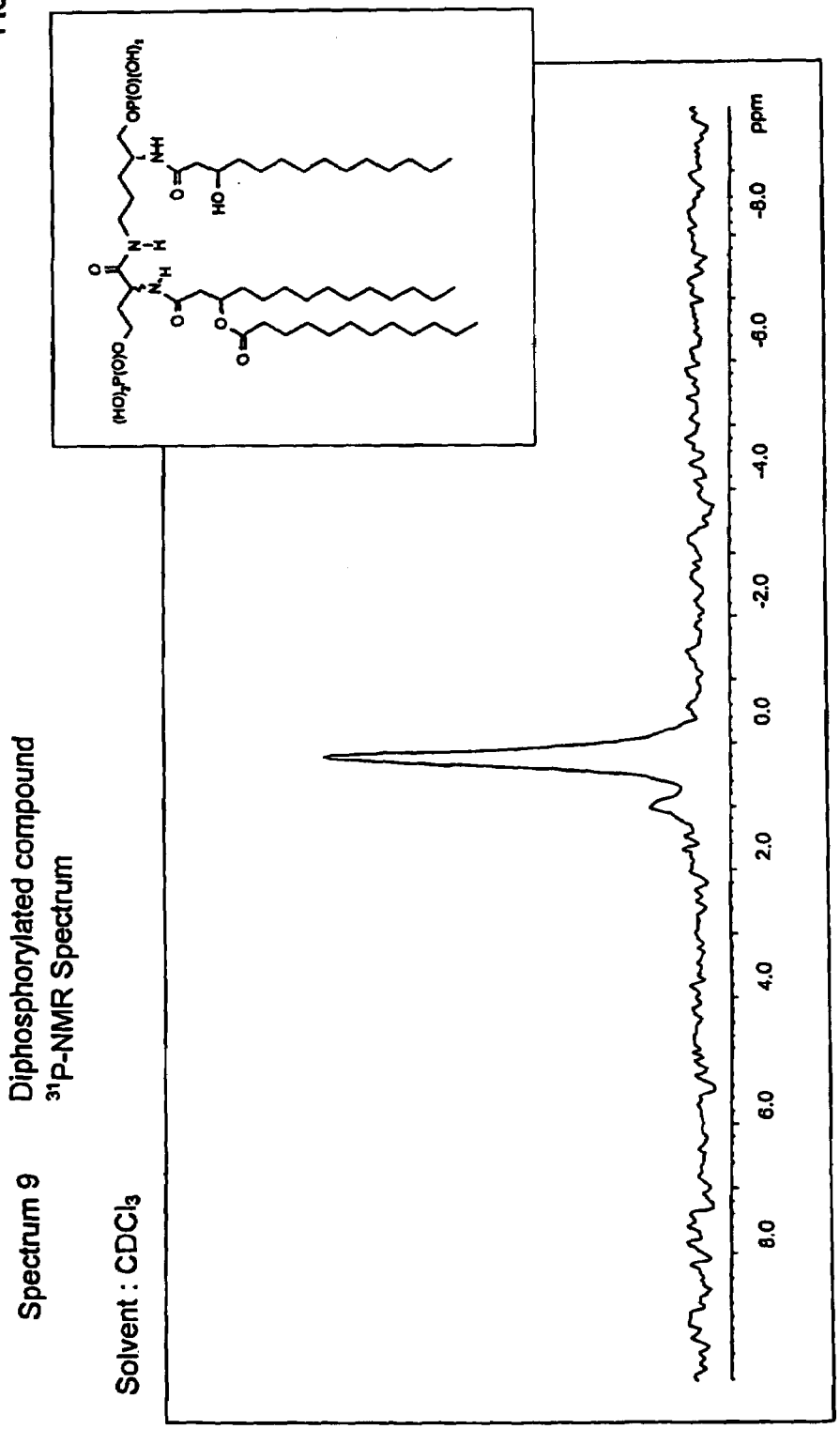

$^{31}$P-NMR spectra (Spectra 8 & 9) (FIGS. 46 & 47)

For both mono- and diphosphorylated compounds, a single peak is observed.

EXAMPLE V

Pharmacological Studies of the Compounds According to the Invention

1. Endotoxicity Determination by the Limuls Chromogenic Test

Endotoxicity was determined by a chromogenic Limuls Amoebocyte Lysate test (Chromogenic LAL of Charles River Endosafe, batch # EK412E, Charleston, USA). This test is based on activation by a lipopolysaccharide (LPS) or structurally analogous products, of an enzymatic cascade present in LAL. This enzymatic activation is demonstrated by cleavage of a chromogen linked to a peptide under the action of a protease, at the final stage of this enzymatic cascade according to the following reaction scheme:

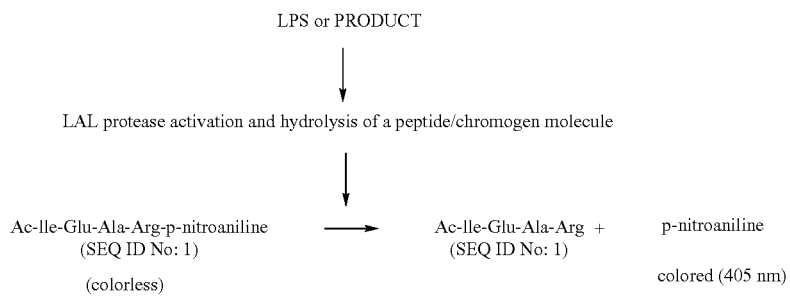

The enzymatic reaction is conducted at 37° C. and the time-course chromogen formation is measured at 405 nm. In the final stage of this time-course determination assay, the time required to achieve an OD of 0.2 unit is recorded and the endotoxic activity is calculated based on an LPS standard (standard curve).

Results are expressed in EU (Endotoxin Unit) in relation to a standardized preparation of $E.\ coli$ lipolysaccharides. For this series of assays, 1 EU corresponds to 0.08 mg of LPS equivalent.

The results show a relatively high degree of variability, though this is normal for such a kind of quantitative assays which provides, in essence, an indication on magnitude. LAL testing is chiefly conducted to demonstrate the absence of pyrogens (upper limit of endotoxin concentration) in pharmaceutical preparations. It is mandatory to compare the quantitative assay of the pyrogen content with a given well standardized single series of experiments.

Results

The results (mean±standard deviation) obtained for the products of the invention are set forth in Table (A):

TABLE (a) Activation of limulus amoebocyte lysate (LAL)

| Products | LAL activity in EU/mg | LAL activity in LPS equivalents ng eq. LPS/mg |
|---|---|---|
| OM-294-DP | 56 ± 48 | 6.2 |
| OM-294-MP | 13 ± 2 | 1.4 |
| $E.\ coli$ LPS (reference) | $7.7 \pm 1.6 \times 10^6$ | $0.85 \times 10^6$ |

The compounds of the invention are $10^6$-fold less active than LPS in the LAL test. OM-294-DP and OM-294-MP are therefore particularly interesting products by virtue of their low toxicity, when taken together with their ability to mediate biological activites and act as immunomodulators (both in vivo and in vitro).

2. Determination of Bone Marrow Stem Cell Proliferation of Mice in Response to LPS Stimulation or Compounds According to the Invention Procedure Two six-week old male C57/BL6 mice were killed by $CO_2$ inhalation followed by cervical dislocation. The mice were washed with alcohol, and the skin of the posterior members was entirely removed. The hip, femur and tibia bones were removed by joint disruption. The flesh was grossly removed using a scalpel. The bones were cleaned and the bone ends were cut with scissors. The marrow was extracted from the bone lumen by injecting three times 1 ml of Dulbecco's Modified Eagle Medium (DH medium) from the the extremities which were cut with scissors. The cells were suspended in DH medium and centrifuged at 300×g for 5 minutes. The supernatant fluid was discarded and the stem cells were suspended in DH medium supplemented with 20% foetal calf serum (FCS) The cell concentration was adjusted to 500 000 cells/ml.

Products previously dissolved in DH medium supplemented with FCS, amino acids and antibiotics were serially diluted, directly into 96-well microtiter plates. 9 dilutions are performed using a dilution factor of 3.16. The products are tested in series of six and each microtiter plate includes a negative control containing plain medium. The final volume in each well is 100 μl. The microplates are incubated for 1 hour at 37° C. under 8% $CO_2$-100% RH incubator to buffer the medium. After 1 hour, 100 μl of the cell suspension are added to the products and incubation is continued for 7 days.

Proliferation is determined by measuring the oxydation of a chromogenic substrate (XTT) in mitochondria of viable cells.

7 days later, the microtiter plates are centrifuged for 5 minutes at 400×g, and 100 μl of the supernatant fluid are withdrawn and discarded. 50 μl of a 1 mg/ml XTT sodium 3-[1-phenylamino-carbonyl)-3,4-tetrazolium]-bis[(4-methoxy-6-nitro)benzene sulfonate] and 0.008 mg/ml PMS ((N-methyl dibenzopyrazine, methyl sulfate) in RPMI medium are added to each well. After 8 hour incubation at 37° C. under 8% $CO_2$ in an incubator at 100% RH, the microtiter plates are read with a spectrophotometer at 480 nm against a standard at 690 nm.

The results are expressed as mean values (+standard deviation) by plotting a dose versus response curve. The values of the negative control composed of DH medium (mean±standard deviation of all experimental data) are also graphically shown.

Figure 1:
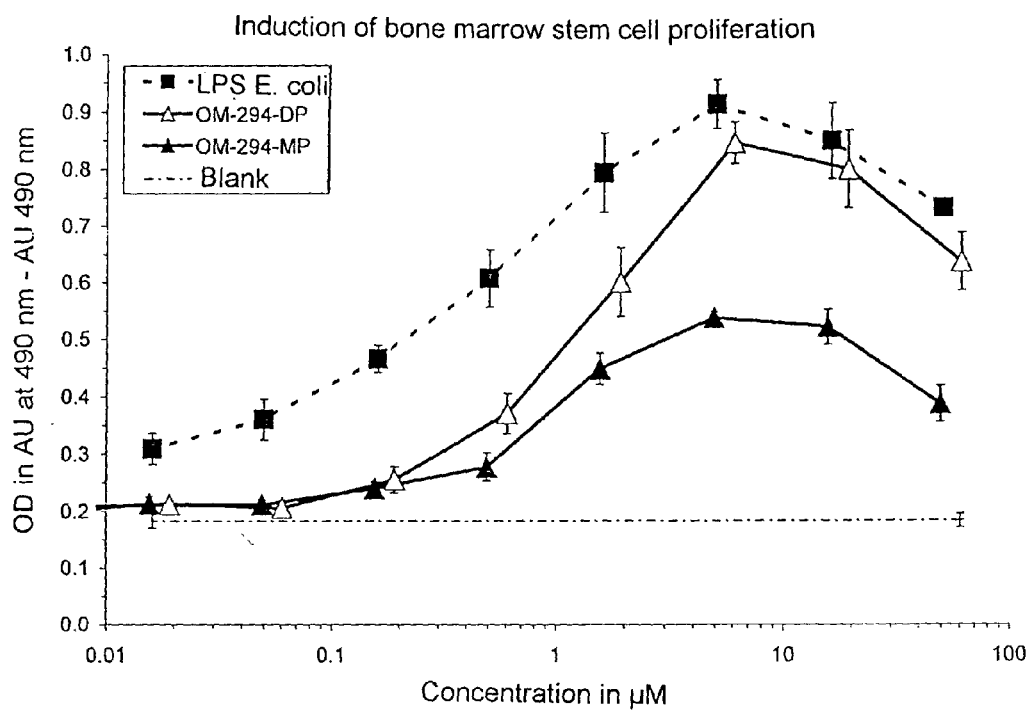
FIG. 1 is a graph of murine bone marrow stem cell proliferation and FIG. 2 is a graph of NO production in murine macrophage cells.

In this experiment, compounds according to the invention induce a significant cell proliferation of mouse bone marrow stem cells. The extent of such a response is nearly equal to that induced by E. coli LPS, but the minimal concentration required to induce a significant response is higher. The monophosphorylated product induces a more moderate response than the diphosphorylated product. FIG. 1 depicts a representative experiment derived from a set of three independant studies run on different cellular preparations.

3. Determining the Production of Nitric Oxide in the Supernatant Fluids of Macrophage Cultures.

Procedure

Two six-week old male C57/BL6 mice were killed by $CO_2$ inhalation followed by cervical dislocation. The mice were washed with alcohol, and the skin of the posterior members was entirely removed. The hip, the femur and the tibia bones were removed by joint disruption. The flesh was grossly removed using a scalpel. The bones were cleaned and the bone ends were cut with scissors. The marrrow was aspirated by injecting three times 1 ml of Dulbecco's Modified Eagle Medium (DH medium) in the bone lumen. The cells were resuspended in DH medium and centrifuged at 300×g for 5 minutes. The supernatant fluid was discarded and the cells were resuspended at a density of 40 000 cells/ml in DH medium supplemented with 20% horse serum (HS) and 30% L929 culture supernatant. L929 is a murine fibroblast cell line the supernatant fluid of which is rich in growth factor for macrophage (M-CSF). The cell suspension was divided into 12 ml aliquots in Petri dishes which were incubated for 8 days in an incubator at 37° C. under 8% $CO_2$ and 100% RH. After 8 days, the stem cells differenciated into mature macrophage cells. The macrophage cells were scraped off by incubating them for 45 minutes at 4° C. in cold PBS buffer. After centrifugation and removal of the supernatant fluid, the cells were resuspended in DH medium supplemented with 5% foetal calf serum (FCS), glutamine, asparagine, arginine, folic acid, mercaptoethanol, and antibiotics (penicillin and streptomycin). The stem cells were collected and cellular density was adjusted to 700 000 cells/ml.

Products previously dissolved in DH medium supplemented with FCS, amino acids and antibiotics were serially diluted directly in 96-well microtiter plates. 9 to 10 dilutions depending on the products were conducted using a 3.16 dilution factor. The products were tested in triplicate and each microtiter plate comprised a negative control containing plain medium. The final volume in each well was 100 μl. The microtiter plates were incubated for 1 hour in an incubator at 37° C. under 8% $CO_2$ and 100% RH to buffer the medium. After 1 hour, 100 μl of the cell suspension were added to the products and incubation was extended for 22 hours.

After 22 hours, the microtiter plates were centrifuged, 5 minutes at 400×g and 100 μl of supernatant fluid were withdrawn and transferred into a microtiter plate. 100 μl of Griess reagent [5 mg/ml of sulfanilamide+0.5 mg/ml of N-(1-napthtylethylene diamine) hydrochloride in 2.5% aq. phosphoric acid], were added to each well. The microtiter plates were read with a spectrophotometer at 562 nm wavelength against a reference at 690 nm. The nitrite concentration was proportional to nitric oxide content. The nitrite content is determined based on a standard curve, which shows a linear relationship in the range of 1 to 25 μM.

The results are expressed as mean±standard deviation after deduction of the negative control value and plotted as a dose versus response curve.

Figure 2:
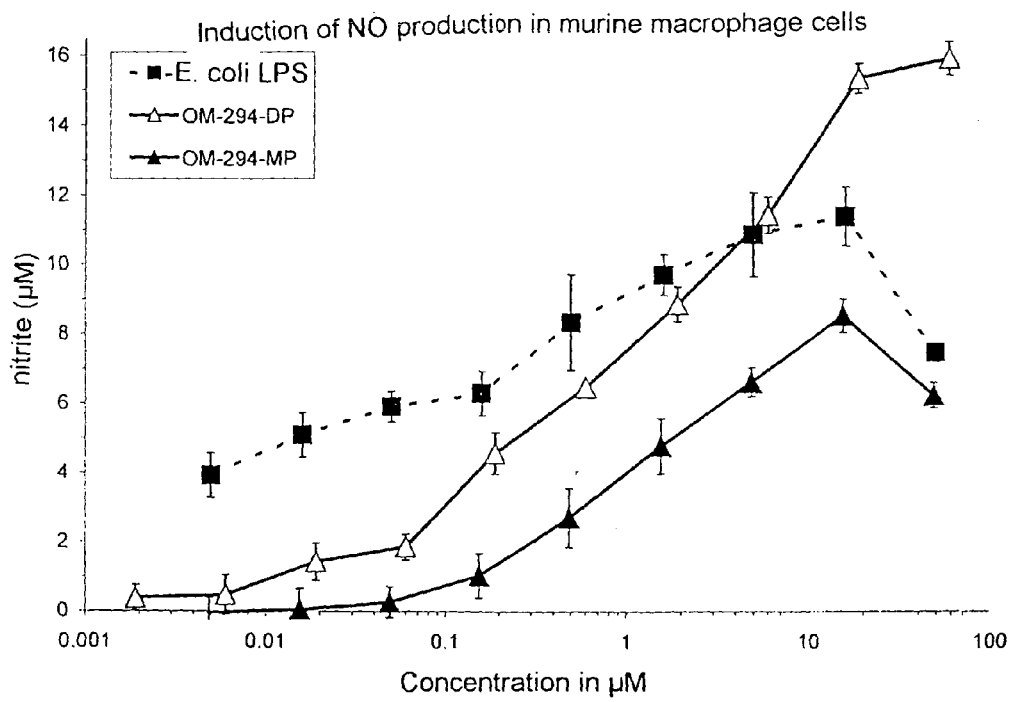
Figure 3:
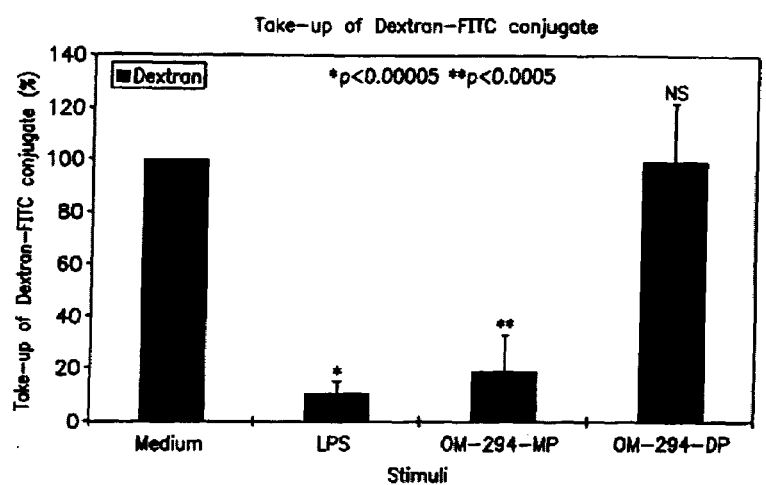
FIGS. 3, 4 and 5 are graphs of Dextran-FITC conjugate take up by human dendritic cells differentiated from monocytes isolated from peripheral blood.

In this experiment, the compounds according to the invention induce the production of nitric oxide by murine macrophage cells in a manner consistent with a dose vs. response curve. The diphosphorylated product induces proliferation to a much greater extent than E. coli LPS, but the concentration required to induce a significant response is higher. The monophosphorylated product induces a weaker response compared to that obtained using the diphosphorylated product and that of E. coli LPS. FIG. 2 depicts a representative experiment derived from a set of 3 independant measurements run on different cell preparations.

4. Determination of the Ability of Compounds According to the Invention to Elicit the Production of α-TNF by Human Alveolar Macrophage Cells Procedure Preparation of alveolar macrophage cells: Human alveolar macrophage cells were obtained by bronchoalveolar washing (BAL) of lungs in patients suffering from lung cancer. BAL is conducted immediately after pulmonary tissue surgery involving healthy parts of the pulmonary lobe. Washings are performed using 0.8% NaCl with the aid of a 50 ml capacity syringe. Cells recovered are made up for greater than 85% of macrophage cells, the majority of other cells being lymphocytes. After centrifugation, the cells are suspended into RPMI medium and the red blood cells are removed by centrifugation on (Research-Grade) Ficoll Pack. The macrophage cells are washed 3 times with HBSS and seeded into 24-well microtiter plates at a rate of 1 ml per well containing a total of 1 000 000 cells. After incubation for 1 hour at 37° C., the resulting macrophage cells become adherent and the wells are washed three times with 1 ml of HBSS in order to remove non adherent cells. After the washing step, 1 ml of RPMI is added to each macrophage cell-containing well.

Incubation with products and assay of α-TNF: Alveolar macrophage cells are incubated at 37° C. under 5% $CO_2$ in the presence of 0.1 μg/ml, 1 μg/ml and 10 μg/ml concentrations of the following products:

Negative control: RPMI

Positive control: E. coli LPS (serotype 05: B5, Difco, Detroit, U.S.A.)

Monophosphorylated compound according to the invention (OM-294-MP)

Diphosphorylated compound according to the invention (OM-294-DP)

The culture supernatants are recovered after 24 hours and analyzed for α TNF content (BioSource Cytoscreen Kit, Camarillo, Calif., U.S.A) which has a sensitivity of 1 pg/ml.

Results

The monophoshorylated and diphosphorylated derivatives persuant to the invention induce moderate production of α TNF in concentration as low as from 10 μg/ml. The monophosphorylated derivative according to the invention induces α TNF production to a higher extent than the diphosphorylated one. The LPS positive control induces at all three tested concentrations high production of α TNF.

The results are listed in Table (a)

TABLE (a) Induction of α TNF production by OM-294-MP and OM-294-DP in human alveolar macrophage cells

| Product | α TNF [pg/ml] mean ± standard deviation of 3 independant experiments | | | |
|---|---|---|---|---|
| | 0 µg/ml | 0.1 µg/ml | 1 µg/ml | 10 µg/ml |
| Negative control: RPMI | 195 ± 70 | | | |
| Positive control: E. coli LPS | | 7667 ± 115 | 9858 ± 2148 | 10390 ± 3415 |
| OM-294-MP-1 | | 246 ± 38 | 353 ± 75 | 1049 ± 295 |
| OM-294-MP-2 | | 205 ± 62 | 291 ± 70 | 1124 ± 406 |
| OM-294-DP-1 | | 156 ± 66 | 117 ± 85 | 329 ± 141 |
| OM-294-DP-2 | | 171 ± 79 | 88 ± 61 | |

5. Determining the Capacity of Compounds in Accordance with the Invention to Inhibit α TNF Production in Human Alveolar Macrophage Cells, in Response to *E. coli* Lipopolysaccharide (LPS)

Procedure

Preparation of alveolar macrophage cells: Human alveolar macrophage cells were obtained by bronchoalveolar washing (BAL) of lungs in patients suffering from lung cancer. BAL is conducted immediately after pulmonary tissue surgery involving healthy portions of the pulmonary lobe. Washings are performed using 0.8% NaCl with the aid of a 50 ml capacity syringe. Cells recovered are made up for greater than 85% of macrophage cells, the majority of other cells being lymphocytes. After centrifugation, the cells are suspended into RPMI medium and the red blood cells are removed by centrifugation on (Research-Grade) Ficoll Pack. The macrophage cells are washed 3 times with HBSS and seeded into 24-well microtiter plates at a concentration of 1 ml per well containing a total of 1 000 000 cells. After incubation for 1 hour at 37° C., the resulting macrophage cells become adherent and the wells are washed three times with 1 ml of HBSS in order to remove non adherent cells. After the washing step, 1 ml of RPMI is added to each macrophage-containing well.

Incubation with products and α TNF assay: Alveolar macrophage cells are incubated at 37° C. under 5% $CO_2$ in the presence of *E. coli* LPS (O5: B5 serotype, Difco, Detroit, U.S.A.) at 1 mg/ml to which are added simultaneously the following products at a concentration of 10 µg/ml:

Negative control: RPMI

Monophosphorylated compound according to the invention (OM-294-MP)

Diphosphorylated compound according to the invention (OM-294-DP)

The culture supernatant fluids are recovered after 24 hours and analyzed for α TNF content (BioSource Cytoscreen Kit, Camarillo, Calif., U.S.A) which has a sensitivity of 1 pg/ml.

Results

The diphosphorylated derivative considerably inhibits the production of αTNF normally induced by LPS. The monophosphorylated derivative partially inhibits α TNF producton induced by LPS.

The results are set forth in Table (a)

TABLE (a) Inhibition of LPS-induced α-TNF production by OM-294-MP and OM-294-DP in human alveolar macrophage cells

| Product | α TNF [pg/ml] | % inhibition |
|---|---|---|
| RPMI (negative control) | 73 | — |
| E. coli LPS (10 µg/ml) (positive control) | 8470 | 0 |
| OM-294-MP-1 (10 µg/ml) + E. coli LPS (1 µg/ml) | 4577 | 44 |
| OM-294-MP-2 (10 µg/ml) + E. coli LPS (1 µg/ml) | 4789 | 41 |
| OM-294-DP-1 (10 µg/ml) + E. coli LPS (1 µg/ml) | 1267 | 84 |
| OM-294-DP-2 (10 µg/ml) + E. coli LPS (1 µg/ml) | 1280 | 84 |

6. Effect of OM-294-MP and OM-294-DP Products on Dendritic Cell Maturation

The ability of OM-294-MP and OM-294-DP products to induce maturation of predendritic cells into dendritic cells was evaluated. The following parameters were measured: FITC-Dextran conjugate incorporation and expression of CD40, CD80, CD83, CD86 surface markers.

Procedure

Cells: Mononucleated cells of peripheral blood are isolated from buffy coats of six healthy donors. Donors did not undergo any treatment prior to blood donation.

Cell preparation: Purified monocytes by adherence selection are resuspended in RPMI-1640 medium (Sigma-Aldrich: St.-Louis, Mo., U.S.A) containing 10% of foetal calf serum, GM-CSF (10 ng/ml; IM-HGMI, Immungenex Corp., Los Angelos, Calif., U.S.A.) and IL-4 (10 ng/ml; No 204-IL, R&D System, Minneapolis, Minn., USA) at a density of $1 \times 10^6$ cells/ml and divided into Petri Dishes of 10 cm in diameter (P10, Falcon, Becton Dickinson, Plymouth, UK) ($10 \times 10^6$ cells per dish P10) and cultured for 6 days (with a change to fresh medium after 3 days). These cells are called predendritic cells (DC-6). Maturation of predendritic cells into mature dendritic cells is achieved by incubating cells with OM-294-MP, OM-294-DP or LPS for 3 further days at concentrations set below under Product section. At day 9, (DC-9) cells were harvested and analyzed for different indicators of dendritic cell maturation: assessment of CD40, CD80, CD83, CD86 surface markers as well as of their ability to take up FITC-Dextran conjugate. All theses parameters are analyzed by an EPICS-XL-MCL model FACS (Coulter Immunology, Hialeah, Finland).

Lanzavecchia et al., *J. Exp. Med.*, 179 (1994) 1109; Lanzavecchia et al., J. Exp. Med., 182 (1995) 389.

Data analysis: Expression of surface markers is expressed as % of mean fluorescence of cells stimulated by LPS (positive control); FITC-Dextran conjugate take-up is calculated with respect to take-up rate for cells maintained in basic medium and is expressed in %. Statistic analysis by t-student test involves comparing data obtained from different tests with the data of a positive control. Data significance level is set at $p<0.05$.

Figure 4:
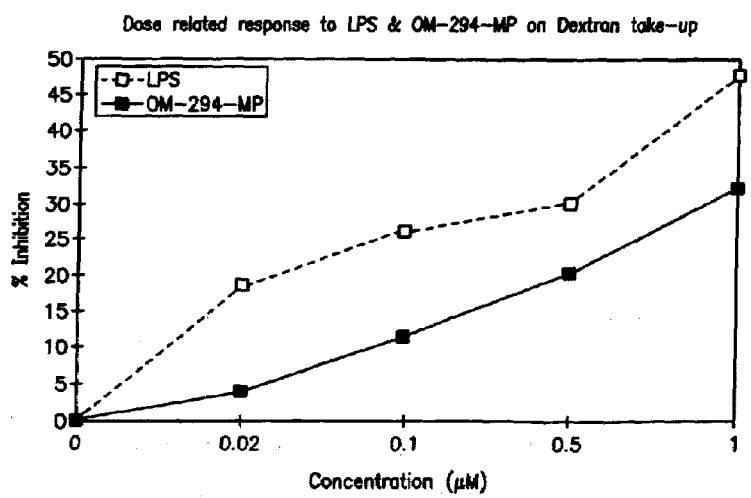
Figure 5:
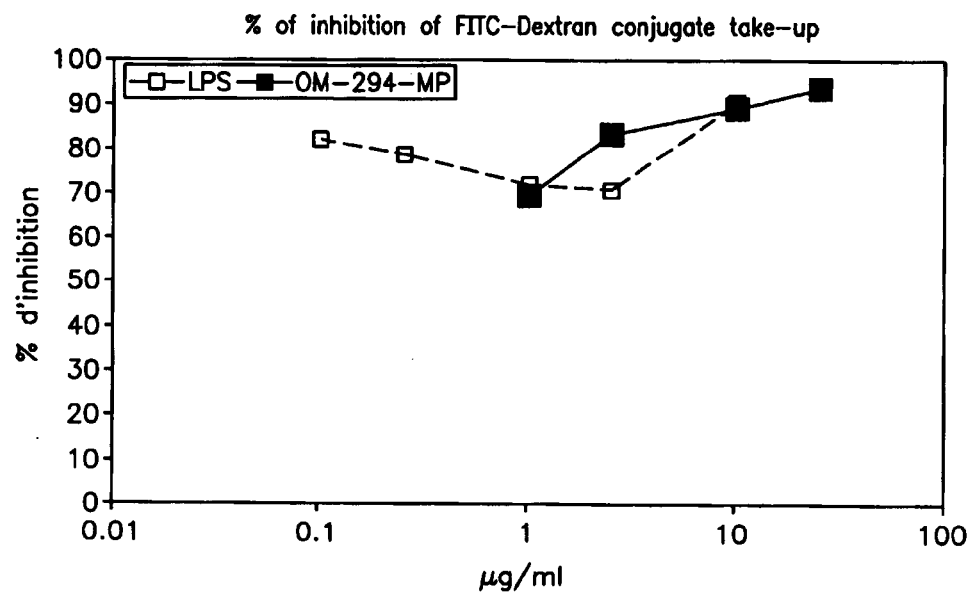
Figure 6:
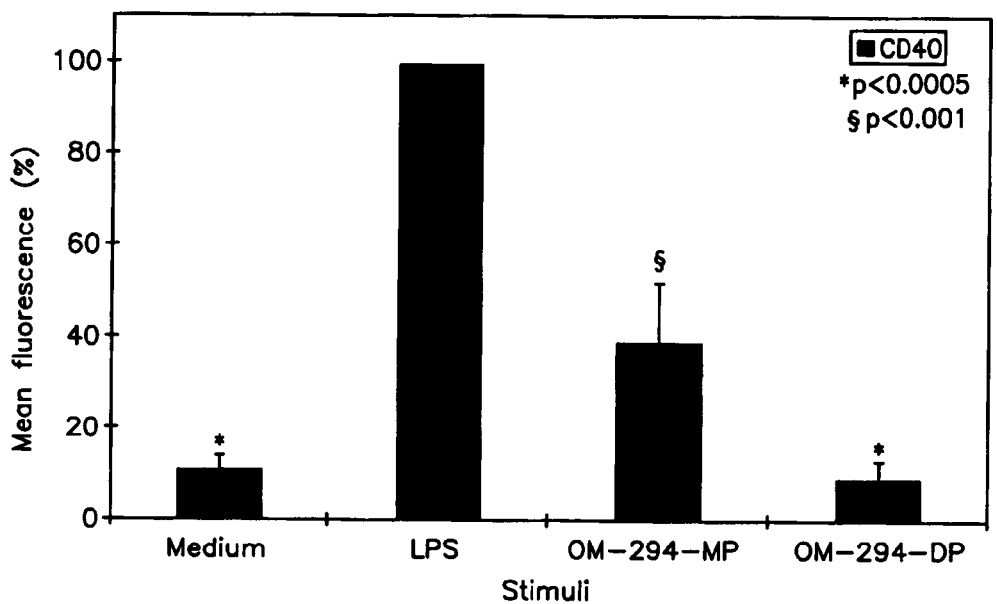
FIG. 6 is a graph of CD40 surface marker expression from human dendritic cells.
Figure 7:
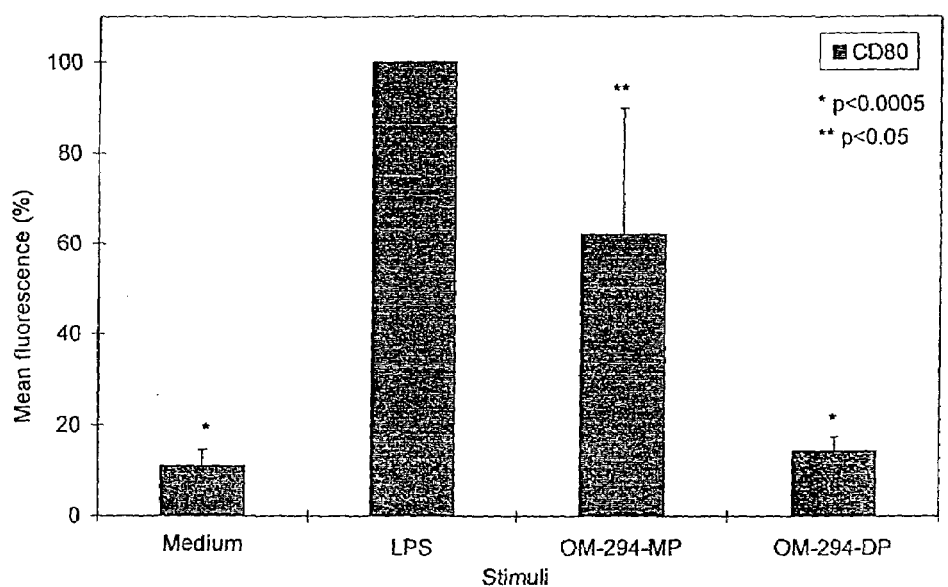
FIGS. 7, 8 and 9 are graphs of CD86, CD83 and CD80 surface marker expression, respectively, from human dendritic cells.
Figure 8:
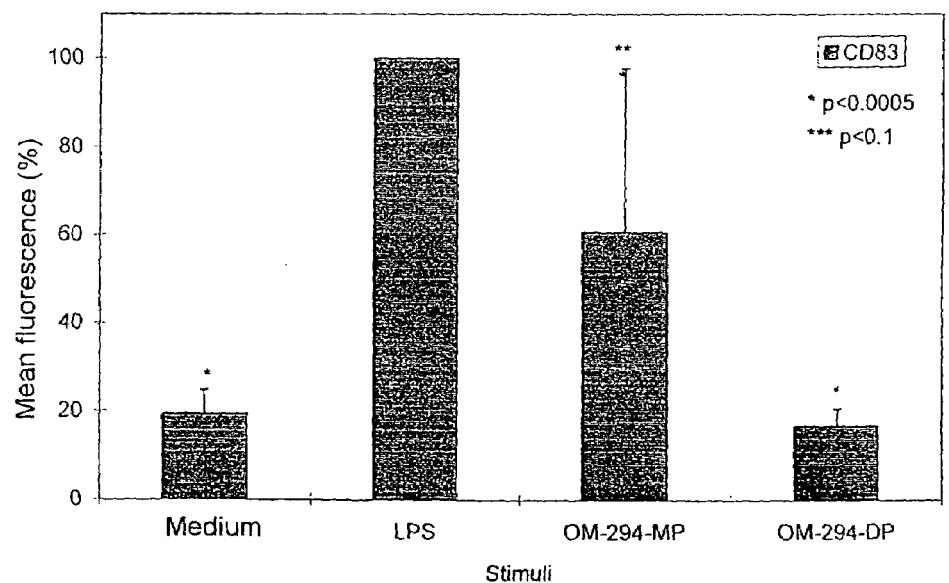
Figure 9:
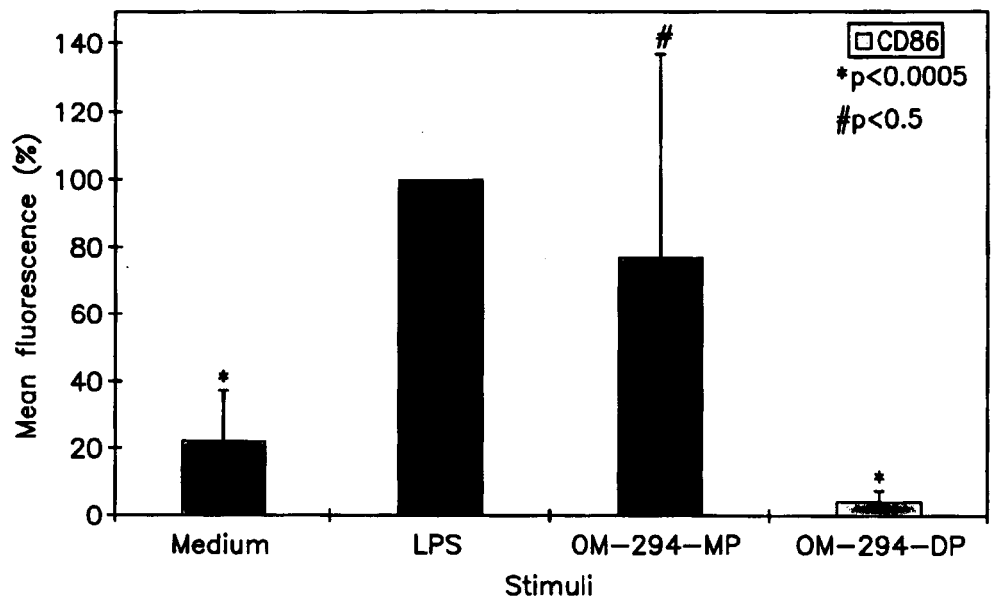

Products: Stock solutions of OM-294-MP and OM-294-DP are prepared at a concentration of 1 mg/ml in 0.9% NaCl/water, with 0.1% triethylamine being added in case of OM-294-MP. Solutions are incubated at 37° C. for 20 minutes, subjected to vigorous stirring during 3 minutes then diluted to 100 µg/ml in RPMI-1640 culture medium and used either at a concentration of 10 mg/ml (FIGS. 3, 6, 7, 8) or at concentrations ranging from 0.02 to 25 µg/ml (FIGS. 4, 5).

Reference Product: *E. coli* lipopolysaccharide (LPS, DIFCO, Detroit, Mich., USA), as a 5 mg/ml stock solution in PBS. An intermediate 100 µg/ml solution is prepared in RPMI 1640 culture medium. Concentrations being tested are either 10 µg/ml (FIGS. 3, 6, 7, 8) or in the range of 0.02 to 10 µg/ml (FIGS. 4, 5).

Results

Immature dendritic cells (DC-6) resulting from monocyte differenciation, through the joint action of GM-CSF and IL-4, are able to incorporate FITC-Dextran conjugate. During the maturation process, cells lose their ability to incorporate the FITC-Dextran conjugate. Analysis are conducted upon reaching the DC-9 differenciation stage.

Results are expressed in terms of % incorporation of FITC-Dextran conjugate observed in non stimulated cells (basic medium) FIG. (3). Cells treated with LPS or OM-294-MP retain respectively only 10% and 19% of their phagocytic capacity, whereas cells stimulated with OM-294-DP totally retain their ability to incorporate FITC-Dextran conjugate (98 and 99%). A dose vs. response curve indicates that OM-294-MP has an outstanding capacity to induce differenciation of DC-6 into DC-9 cells at concentrations ranging from 0.02% g to 25 µg per ml, see FIG. (4) where low concentrations and FIG. (5) where higher concentrations have been tested.

Expression of co-stimulating surface markers is another criterion to assess DC maturation. Expression of CD40, CD80, CD83, CD86 is tested. Results are expressed in terms of % of mean fluorescence based on LPS-induced expression of these markers.

OM-294-MP increases the expression of all surface markers being tested: CD40 (39%), CD80 (62%), CD83 (60%), CD86 (77%) see FIGS. (6, 7, 8, 9).

OM-294-DP exerts an effect similar to that of basic culture medium upon expression of the investigated markers. Such an effect does not exceed 20% of LPS action.

7. Effect of OM-294-MP and OM-294-DP Products on Production of α TNF and IL-12 p70 by Monocytes and Predendritic Cells at DC-6 Stage DC-6 cells ($5\times10^5$/500 µl of medium) are stimulated during 4 hr., 6 hr., and 24 hr., either by LPS (10 µg/ml) or by OM-294-MP (10 µg/ml) or OM-294-DP (10 µg/ml).

Procedure

In vivo experimental conditions: Mononuclear cells of peripheral blood are recovered from buffy coats of 6 healthy donors (donors did not undergo any treatment prior to blood donation). Monocytes are isolated in a Ficoll gradient then purified by adherence selection. Loosely adherent monocytes are harvested and one fraction of the cells is stored as monocytes. Purified monocytes are resuspended into RPMI-1640 medium containing 10% of FCS, at a rate of $1\times10^6$ cells/ml and divided into Petri dishes measuring 10 cm in diameter (P10—Falcon, Becton Dickinson, Plymouth, UK) at a rate of $10\times10^6$ cells/P10 type dish. Cells are cultured in whole RPMI 1640 medium containing GM-CSF (10 ng/ml) and IL-4 (10 ng/ml) during 6 days. At day 6, cells are harvested, washed with HBSS and seeded into a 24-well plate at a density of $5\times10^5$ cells/well in 500 µl of whole RPMI medium and stimulated with LPS (10 µg/ml), OM-294-MP (10 µg/ml) or OM-294-DP (10 µg/ml). α TNF as well as IL-12 p70 are assayed by ELISA in culture supernatants which are recovered after 4, 6 and 24 hours.

Products: OM-294-MP and OM-294-DP products (1 mg/ml stock solution in sterile water) are incubated at 37° C. during 20 min. and kept under vigorous stirring during 3 minutes then diluted to 100 mg/ml and used at a final concentration of 10 µg/ml in RPMI 1640 culture medium.

Reference Product: *E. coli* lipopolysaccharides (LPS, DIFCO, Detroit, Mich., USA), 5 mg/ml stock solution in PBS, intermediate solution in culture medium: 100 µg/ml, used at a final concentration of 10 µg/ml.

Assay of α TNF and IL-12 p70: α TNF KHC3012 kit from Biosource, batch # PP003-J061703 (Biosource International, Camarillo, CA, USA) ELISA was run according to the supplier's instruction manual. IL-12 p70 is assayed in culture supernatants by ELISA using the human IL-12 kit (No. D1200, batch 990 6232, R&D Systems, Minneapolis, Minn., USA).

Results

α TNF

Figure 10:
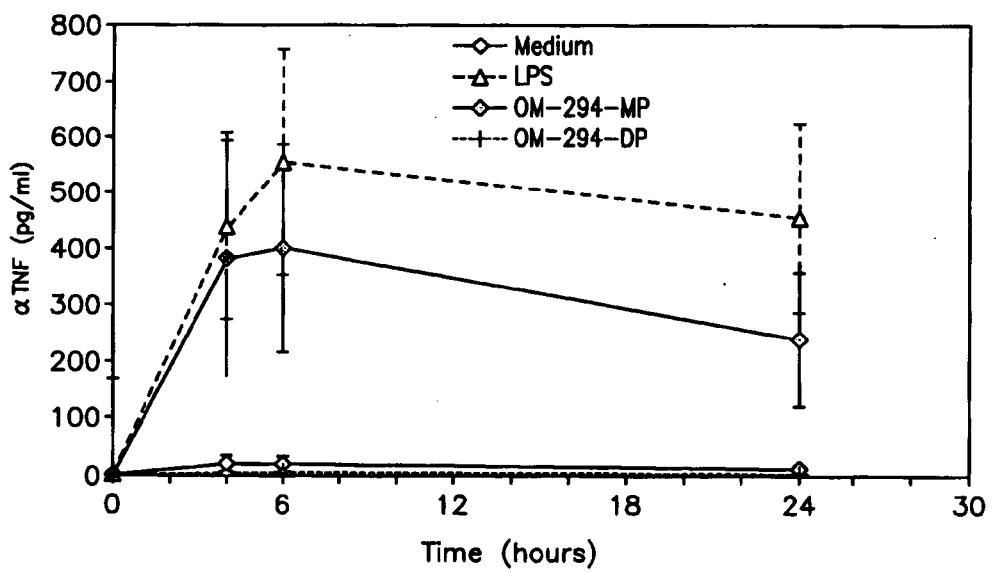
FIG. 10 is a graph of OM-294-MP and OM-294-DP effects of TNF-α production by predentritic cells at DC-6 stage.

OM-294-MP stimulates α TNF production by DC-6 cells in a way similar to LPS both with respect to time-course production rate and α TNF concentration. (FIG. 10)). An α TNF peak is noted for both products between 6 hr. and 24 hr.

OM-294-DP has only a minor stimulating effect on α TNF production by DC-6 cells.

IL-12 p70

Figure 11:
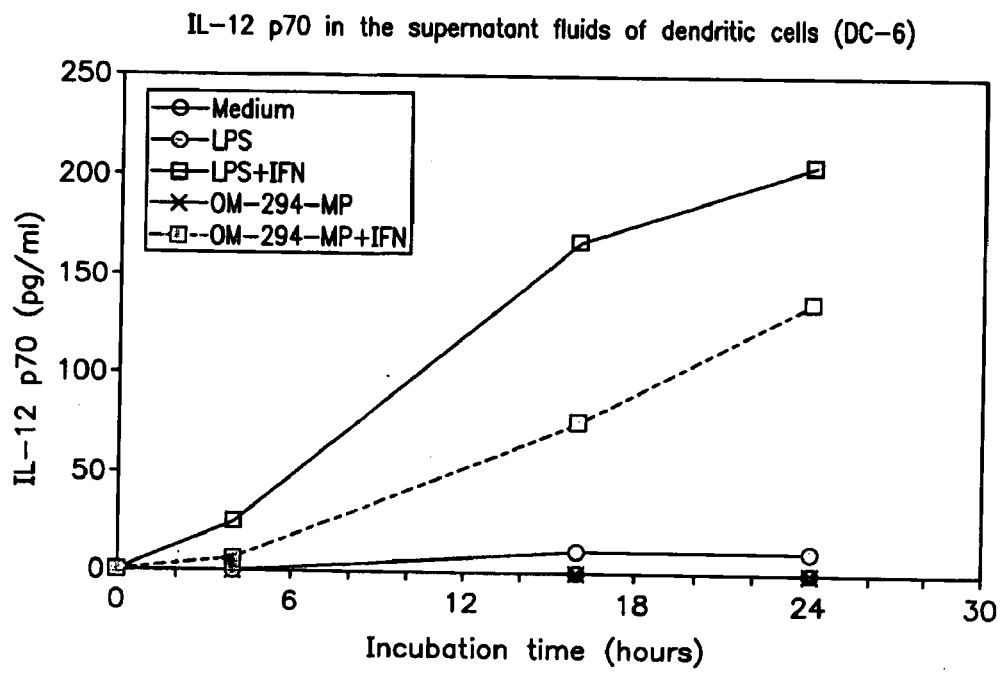
FIG. 11 is a graph of OM-294-MP and OM-294-DP on IL12 p70 production by predentritic cells at DC-6 stage.
Figure 12:
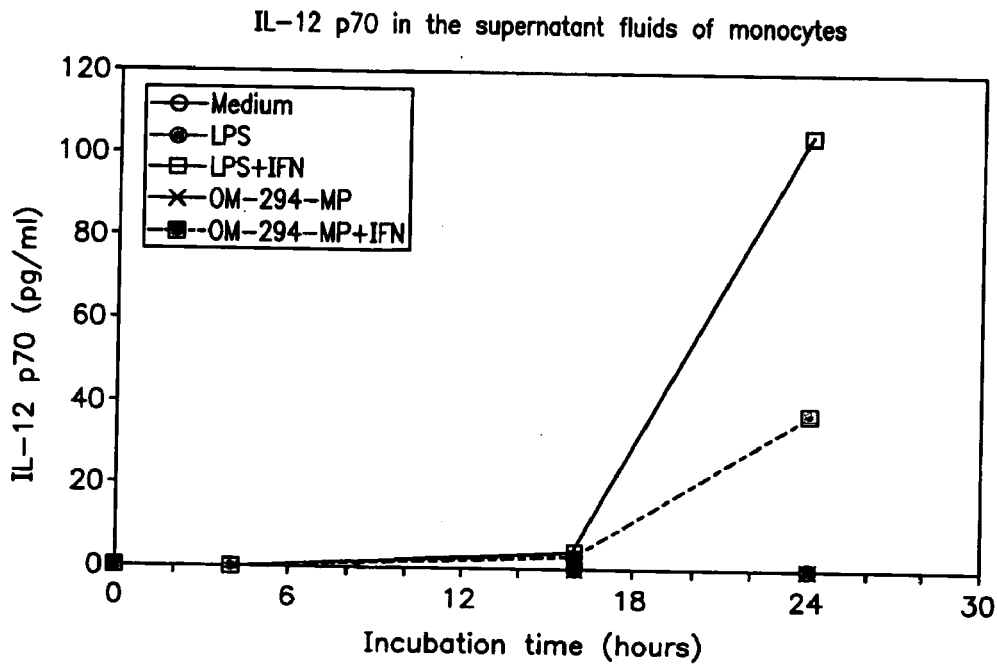
FIG. 12 is a graph of the effect of OM-294-MP on IL12 p70 production in the supernatant fluid of monocytes.
Figure 13:
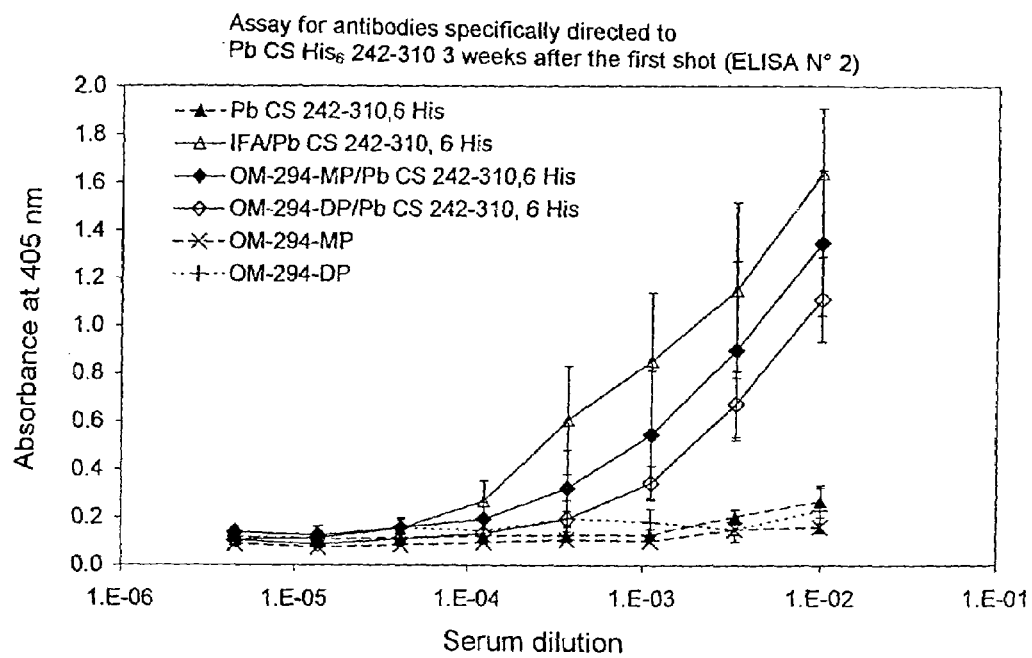
FIGS. 13, 14 and 15 are graphs of ELISA 2, 3 and 4 weeks after the first, second and third immunization of mice with the synthetic peptide Pb CS His6 242-310 amino acid sequence of *Plasmodium berghei* circumsporozoite.
Figure 14:
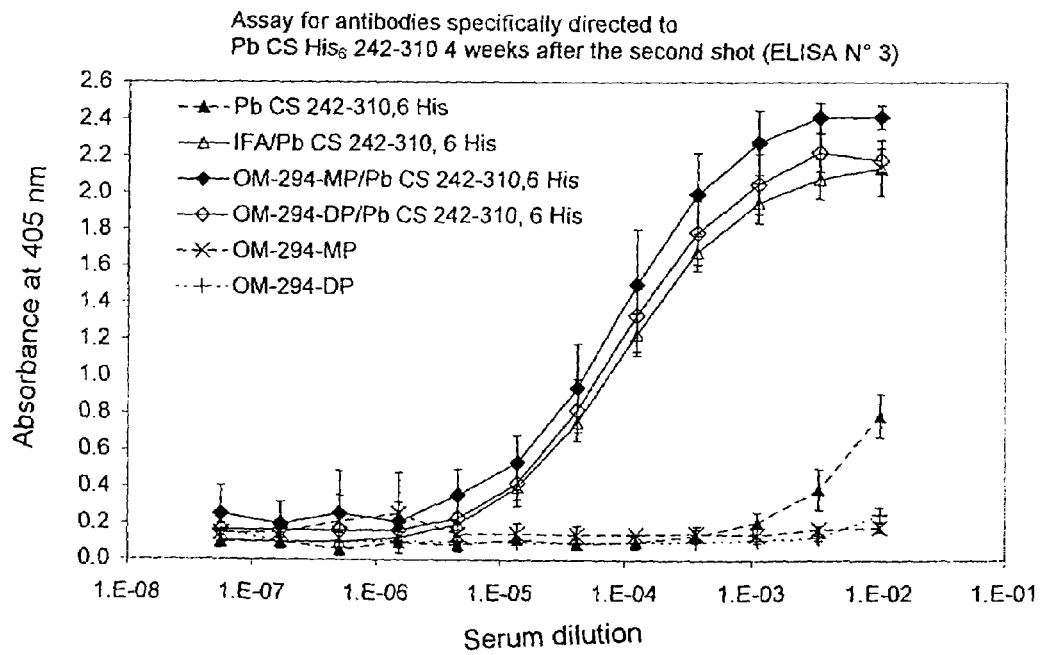
Figure 15:
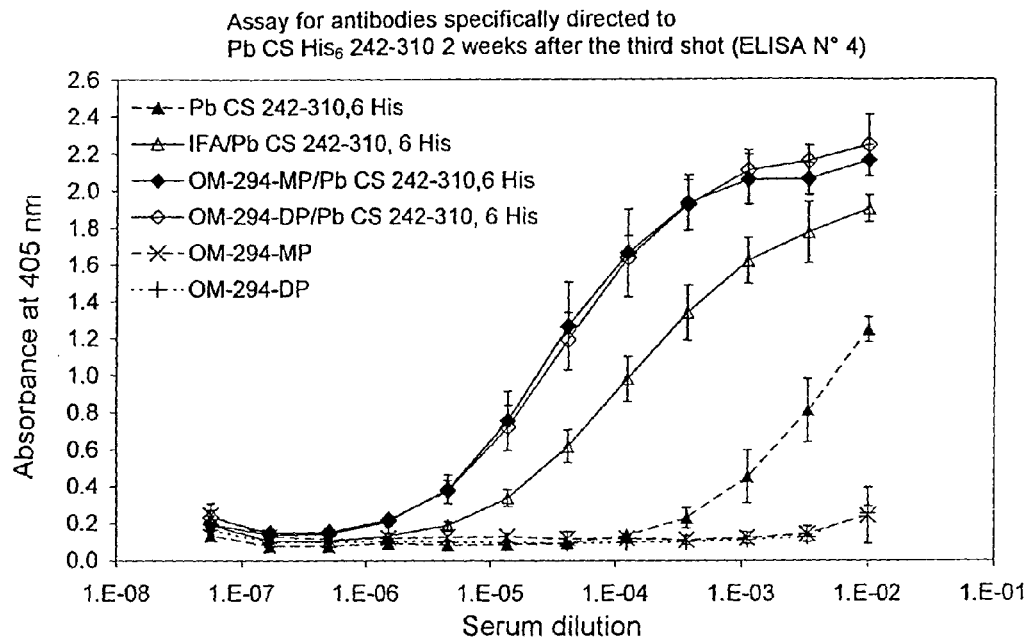
Figure 16:
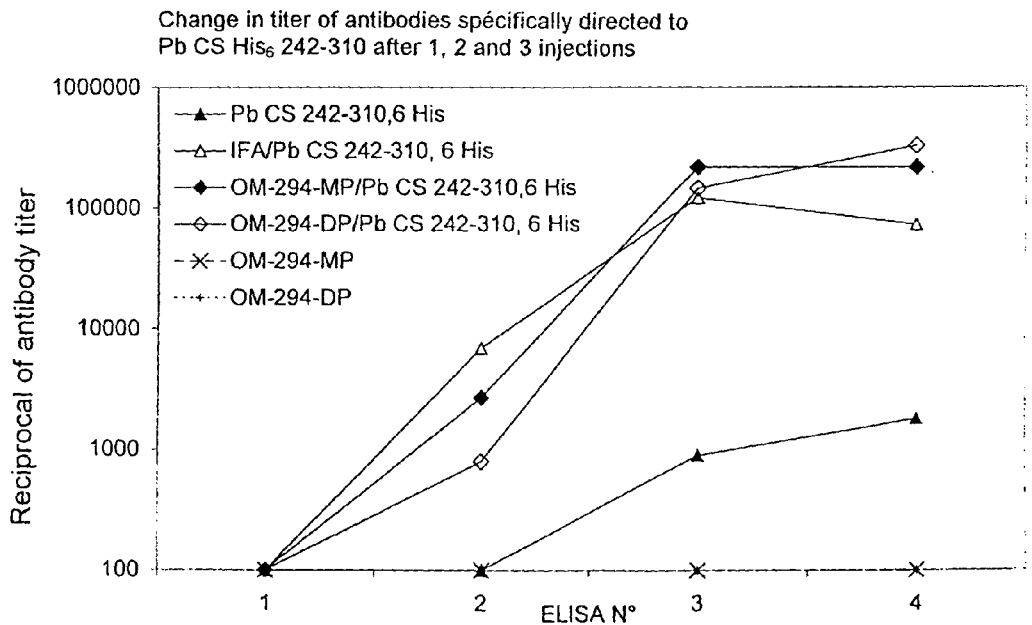
FIG. 16 is a graph of antibody titer before and after immunization of mice with the synthetic peptide Pb CS His-6 242-310 amino acid sequence of *Plasmodium berghei* circumsporozoite.
Figure 17:
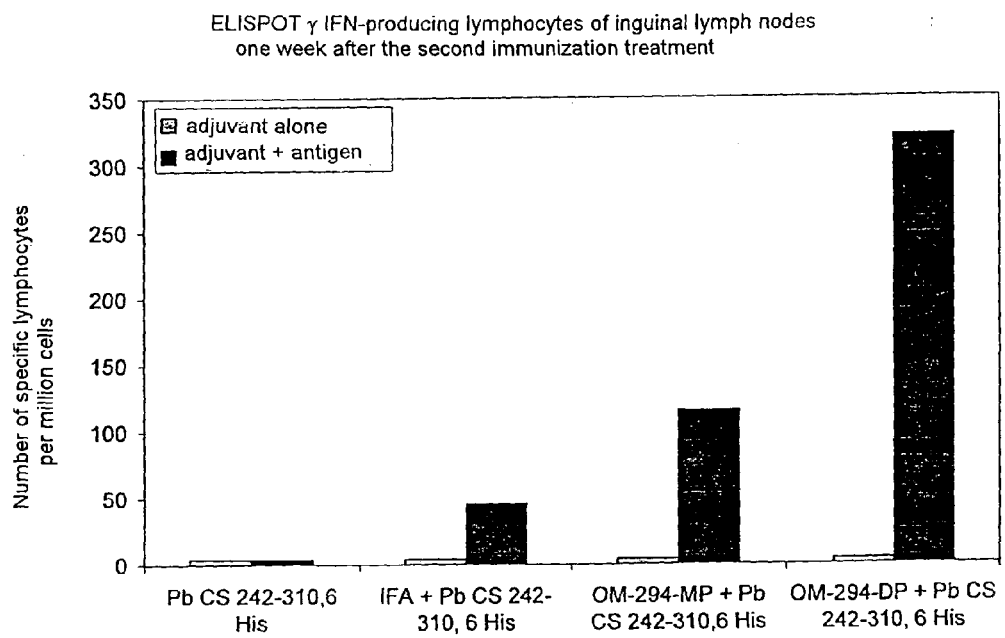
FIGS. 17 to 20 are graphs of ELISPOT IFN-γ IFN producing lymphocytes after immunization of mice with the synthetic peptide Pb CS His-6 242-310 amino acid sequence of *Plasmodium bergei* circumsporozoite.
Figure 18:
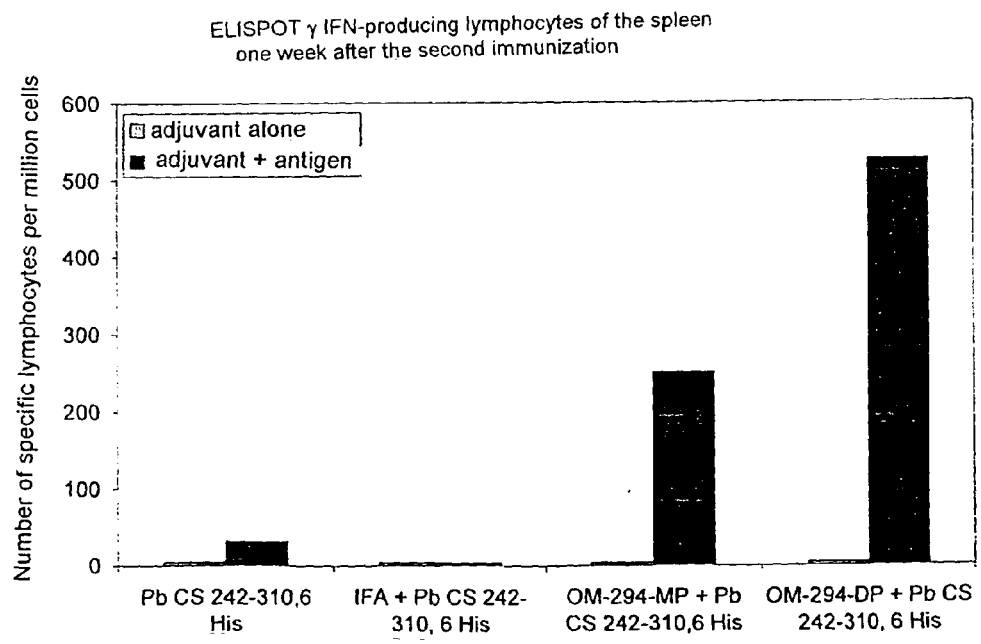
Figure 19:
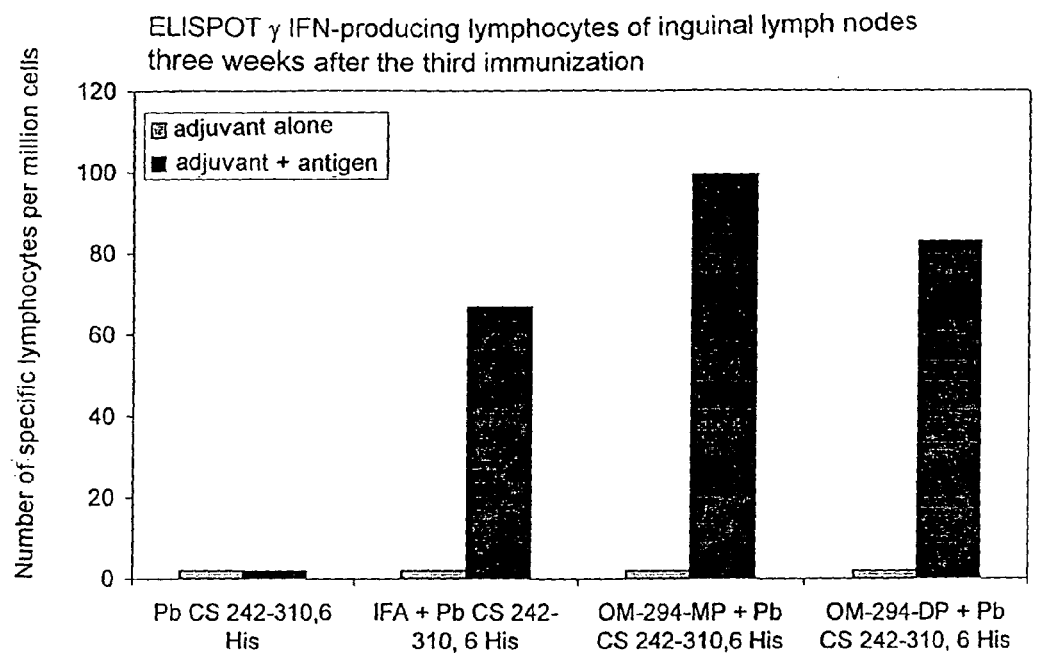
Figure 20:
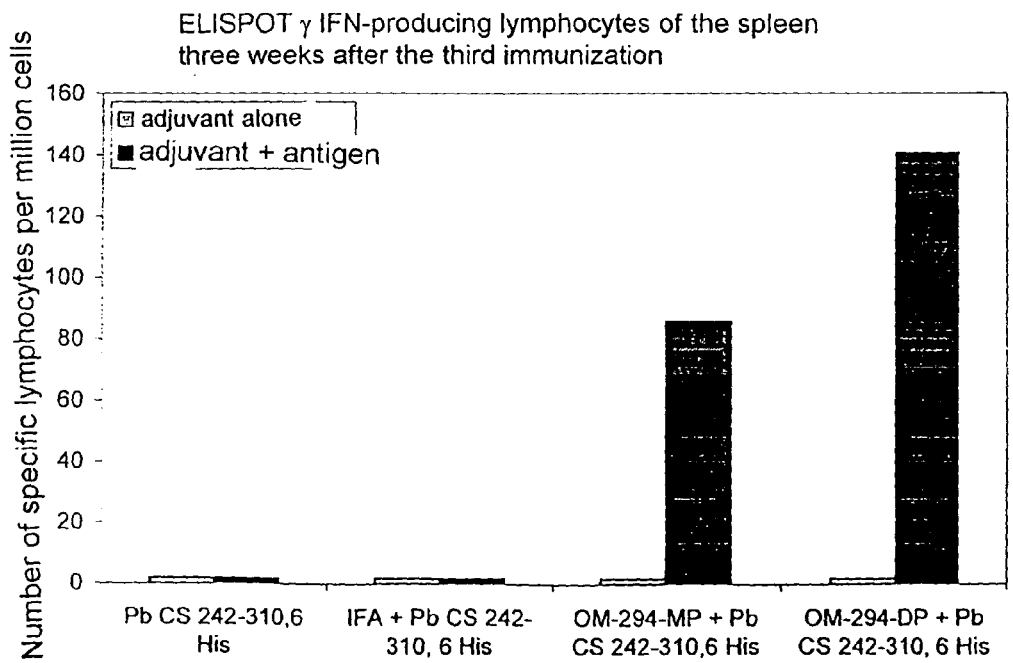
Figure 21:
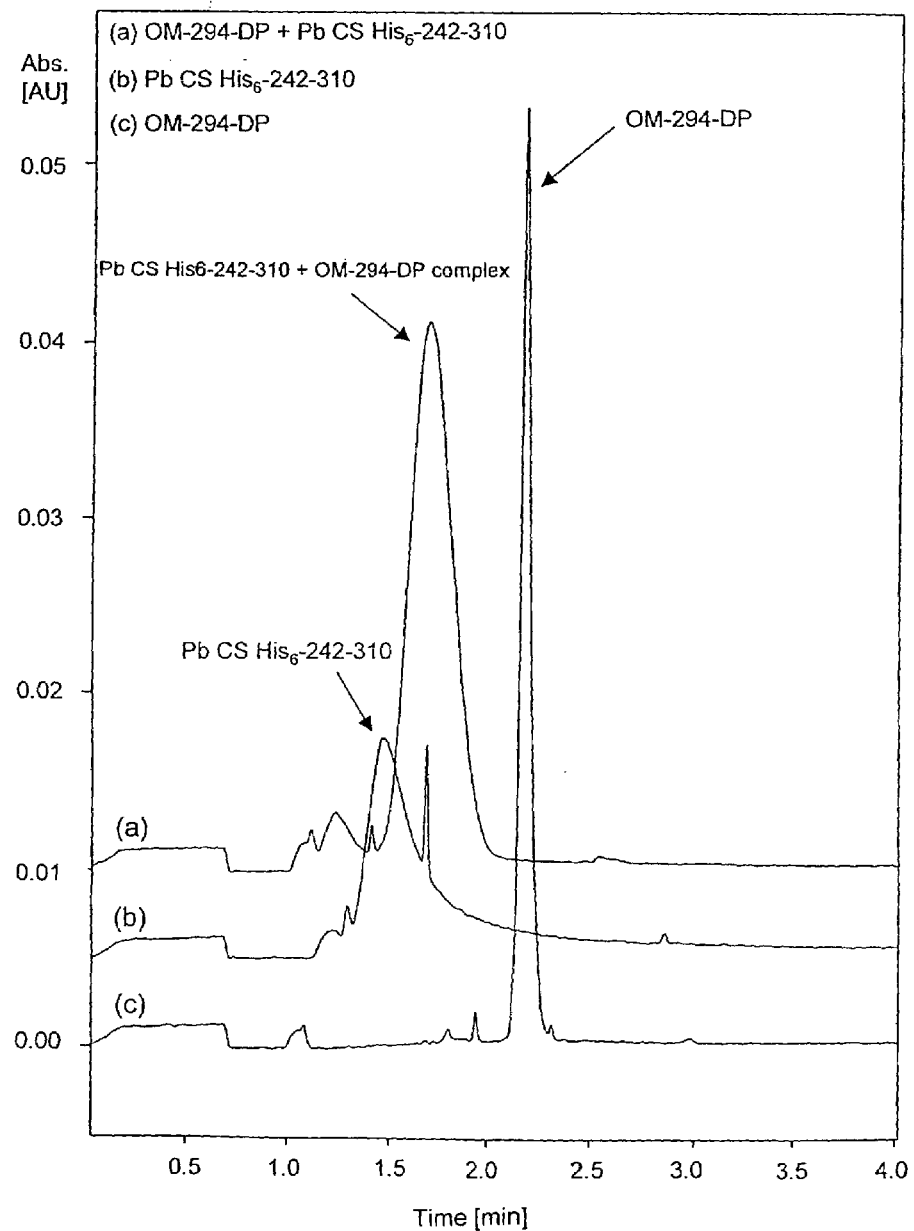
FIG. 21 is an electropherogram.

Generally speaking, IL-12 is induced in presence of γ IFN (LPS+γ INF, OM-294-MP+γ IFN) in monocytes ((FIG. (12)) and DC-6 cells ((FIG. 11)). Cytokine production onset is earlier in DC than in monocytes.

8. Evaluation of OM-294-MP and OM-294-DP Adjuvant Properties in a Murine Immunization Model with a Synthetic Peptide (Pb CS $His_6$-242-310) of the C-Terminal Region of *Plasmodium berghei* Circumsporozoite Surface Proteine Procedure Antigen: Pb CS(HHHHHHGGMN NKNNNNDDSY IPSAEKILEFVKQIRDSITE EWSQCNVTCG SGIRVRKRKRG SNKKAEDLTL EDIDTEI) (SEQ ID No.2) peptide, hereinafter referred to as $His_6$-242-310 amino acid sequence of *Plasmodium berghei* circumsporozoite ANKA strain surface protein plus an N-terminal stretch of 6 histidine, 2 glycine and one methionine residues is obtained by the Merrifield and Atherton synthesis method (Athenon et al, Bioorg. Chem., 8: (1979) 350–341). The polypeptide was prepared on a p-alkoxybenzylalcohol resin (Wang resin) having a substitution rate of 0.4 mmol/g. A 10-fold molar excess of F-moc amino acid derivatives is used with a coupling time of 30 min. The peptide is purified by size exclusion chromatography (W-Porex 5 C-4, 250×10 mm, Phenomenex, Torrance, Calif. U.S.A.) using a 40 min. gradient, ranging from a 10–50% acetonitrile-0.1% trifluoroacetic acid mixture (v/v), at a 3 ml/min. flow rate.

The amino acid composition of the peptide is determined according to the method of Knecht and Chang (*Anal. Chem.*, 58 (1986) 2373–2379) and the molecular weight is checked by mass spectrometry using a Voyager DE model apparatus (Perspective Biosystem, Framingham, Mass., USA). Antigen stock solution is prepared at a concentration of 0.4 mg/ml in 0.9% NaCl/water at pH 8.0.

Adjuvants: Stock solutions of OM-294-DP and OM-294-MP are prepared at a concentration of 1 mg/ml in 0.9% NaCl-water, incorporating 0.1% triethylamine for OM-294-MP. The positive control is comprised of Incomplete Freund's Adjuvant (IFA from Difco, Detroit, Mich., USA) with the negative control being a 0.9% NaCl solution.

Antigen-adjuvant mixture: One volume of antigen and one volume of adjuvant are mixed by vortexing for 3 min.

Immunization regimen: 6-week old female BALB/c mice (6 mice per group) are immunized three times, with a subcutaneous shot in the tail end containing 0.1 ml of the following mixtures:

| Group | adjuvant 0.05 mg/injection | antigen 0.02 mg/injection | number of mice |
|---|---|---|---|
| 1 | — | Pb CS His$_6$-242-310 | 6 |
| 2 | IFA | Pb CS His$_6$-242-310 | 6 |
| 3 | OM-294-MP | Pb CS His$_6$-242-310 | 6 |
| 4 | OM-294-DP | Pb CS His$_6$-242-310 | 6 |
| 5 | OM-294-MP | — | 6 |
| 6 | OM-294-DP | — | 6 |

| Immunization and sampling schedual: | | | | | |
|---|---|---|---|---|---|
| Weeks | 0 | 3 | 4 | 7 | 9 |
| Immunizations | ↑ | ↑ | | ↑ | |
| Antibody specific response | ↑ | ↑ | | ↑ | ↑ |
| CTL response | | | ↑ | | ↑ |

Lymphoid organ and blood sampling:

Serum sampling: Blood sampling is conducted at weeks 0, 3, 7 and 9. Blood is allowed to stand for 6 min. at 37° C., then is kept overnight at 4° C. Serum is subsequently frozen at −80° C. until time of antibody assay.

Recovery of inguinal lymph nodes and spleen: A portion of each animal group is killed after 4 or 9 weeks, respectively. Inguinal lymph nodes and the spleen are surgically removed.

Determination of anti-Pb CS His$_6$ 242-310 antibody titer:

Assay of antibodies specifically raised against Pb Cs His$_6$ 242-310 antigen is performed by ELISA. Binding of antigen is done in 96-well microtiter plates (Maxisorp F96, Nunc, DK) by conducting overnight incubation in a moist chamber at 4° C. with each well containing 0.1 ml of PBS (phosphate buffered saline) containing 0.001 mg/ml of Pb CS His$_6$242-310 antigen. Blocking of the microtiter plate is performed with PBS containing 1% of bovine serum albumin (BSA, Fluka, Switzerland). Plates are washed with PBS containing 0.05% Tween 20 (Sigma, St. Louis, Mo., USA). Serum samples collected at 0, 3, 7 and 9 weeks are serially diluted with dilution buffer (PBS containing 2.5% of skimmed milk powder and 0.05% of Tween 20), then transferred into a microtiter plate and allowed to stand for 1 hr. at room temperature (RT). Plates are then washed with PBS, a diluted solution containing mouse polyclonal anti-immunoglobulin coupled to alkaline phosphatase (Sigma, St. Louis, Mo., USA) is then dispensed into those plates and incubated for 1 hr. at RT. Plates are washed with PBS and specific antibodies are revealed by a color reaction by adding the alkaline phosphatase substrate, p-nitrophenylphosphate (Sigma, St. Louis, Mo., USA). Absorbance at 405 nm is read with a microtiter plate reader (Dynatech 25000 ELISA reader, Ashford, Middlesex, UK), each serum sample is measured in duplicate. Results stand for the mean of all measurements relating to mice in each group. The antibody titer is given by the highest dilution giving a significantly positive response, i.e. an OD greater to background noise level±3 SD.

ELISPOT assay:

Antibodies specifically directed to murine γ-interferon (O1E703B2) are bound by running an overnight incubation at 4° C. in a moist chamber, adding an antibody solution at 50 μg/ml in an ELISPOT microtiter plate with the well bottom being covered by nitrocellulose (Millipore, Molsheim, France). The blocking step is effected by adding DMEM medium (Life Technologies, Grand Island, N.Y., USA) containing 10% of foetal calf serum (FCS, Fakola, Switzerland) and letting stand for 2 hours at 37° C. Cells obtained from lymphoid organs (inguinal lymph nodes and spleen) are cultured in microtiter plates at a density of 200 000 cells/well, then co-cultured during 24 hours at 37° C. with 100 000 P815 cells either challenged or not with the Pb CS 245-252 short peptide. After incubation, cells are removed and following the washing step, a second murine anti-γ IFN antibody-biotin complex (ANI, 2 μg/ml in PBS with 1% BSA) is added and incubated for 2 hr. A streptavidin-alkaline phosphatase conjugate (Boehringer Mannheim, Mannheim, GFR) is added and incubated for 1 hr at 37° C., and thereafter 3 washings are effected with PBS containing 0.05% Tween 20, followed by 3 washings with PBS. Presence of anti-γ IFN immune complexes is demonstrated by adding BCIP/NBT substrate (Sigma, St. Louis, Mo., USA). This reaction is stopped by washing with tap water. Spots which are positive for γ IFN are then counted under a stereomicroscope. Specific spot count is the difference between spots counted in presence of cells challenged with peptide and spots counted in absence of peptide. Results are given as mean measurement values recorded for mice in each group. They are expressed as the number of spots per million of cultured blood cells.

Results

Antibody response: Production of antibodies specifically directed to Pb CS His$_6$-242-310, as determined by ELISA, is graphically depicted for mice administered one, two and three immunization shots. The control involves one single shot of antigen alone and results in a very weak antibody titer. Antibody titer achieved with one single antigen shot in admixture with OM-294-MP or respectively OM-294-DP is almost as high as the response observed with Incomplete Freund's Adjuvant (IFA) in admixture with the same antigen (FIG. (13)). After two shots, OM-294-MP and OM-294-DP adjuvants are able to elicit a serological response which is respectively greater than that of IFA (FIG. (14)). Following three shots, OM-294-MP and OM-294-DP adjuvants are able to elicit a serological response which is greater than that of IFA (FIG. (15)).

FIG. (13) ELISA, run 3 weeks after the first immunization shot.

FIG. (14) ELISA, run 4 weeks after the second immunization shot.

FIG. (15) ELISA, run 2 weeks after the third immunization shot.

FIG. (16) Antibody titer as measured before and after one, two and three immunization shots.

Antibody titers of animals in each group before an immunization shot and after one, two and three immunization shots are given as mean values (FIG. (16)).

CTL Response: Recognition of the T-cell epitope Pb CS 245-252 present in Pb CS His$_6$-242-310 peptide previously used for immunization is well demonstated by the ELISPOT test. T-lymphocyte response recorded in immunized animals (inguinal lymph nodes and spleen, recovered one week after the second shot and respectively two weeks after the third shot) is demonstrated by the rise in positive spot count for γ interferon (γ IFN). Results set forth in the FIGS. (17, 18, 19 and 20) are calculated as mean value of measurements achieved with each dilution and for mice of each group. They are expressed in number of spots per million cells in culture.

Both OM-294-MP and OM-294-DP adjuvants result in a very significant increase in CTL response of lymphocytes derived from spleen and inguinal lymph nodes. Spleen responses are higher than those of inguinal lymph node responses. CTL activity induced by OM-294-MP and OM-294-DP adjuvants is clearly superior to the one induced by IFA.

9. Demonstrating Non Covalent OM-294-antigen Complexes by Capillary Electrophoresis Capillary electrophoresis is used in this example to demonstrate non covalent complex formation between OM-294-DP and Pb CS $His_6$-242-310 peptide during formulation of the vaccine preparation.

Procedure

Analysis method: 20 mM sodium borate buffer (di-sodium tetraborate decahydrate, Merck, No 6306) pH adjusted to 7.4 with 1 N NaOH (Fluka No 72072)

Zone-divided capillary tube (ungrafted), length 30 cm, diameter 50 µm.

Detection is performed at 200 nm using a Beckman PACE MDQ model apparatus (Beckman, Brea, Calif., USA).

| Separation conditions | | | |
|---|---|---|---|
| Time [min.] | process | Pressure | Solvent |
| 0.00 | Capillary wash | 20.0 psi | H₂O |
| 3.00 | Capillary wash | 20.0 psi | 1N NaOH |
| 6.00 | Sample injection | 0.5 psi | Borate buffer |
| 6.08 | Separation | 30.0 KV | Borate buffer |

Antigens: Pb CS $His_6$-242-310 synthetic peptide at 1 mg/ml in $H_2O$

Adjuvant: OM-294-DP at 1 mg/ml in $H_2O$

Antigen-adjuvant mixture: 250 µg/ml+250 µg/ml

Results

Antigen-adjuvant complex formation as observed in formulating this vaccine preparation is demonstrated on the electrophoresis diagram by the disappearance of the adjuvant peak and a shift in the antigen peak giving rise to a new peak which is specific of the newly formed complex (FIG. (21)).

10. Treatment of Peritoneal Carcinoma Induced by Injection of Cells Derived from PROb Syngenic Tumoral Line in BDIX Rats This experiment is aimed at demonstrating an antitumoral effect of OM-294-DP when administered in a series of i.v. shots to rats bearing macroscopic tumors of a few mm in size.

Procedure

Animals: In-bred BDIX rat strain was established by H. Druckrey in 1937. A pair of rats from Fribourg Max Planck Institute (RFA) was the initial source of this colony which has been maintained since 1971 in the laboratory animal house facility by the single line system. According to this system, one single pair of sister-brother subjects is selected to give rise to the descendants of the next generation. Rats used in this work are from the Experimental Animal Breeding Center in Iffa-Credo (Arbresle, France) which has been conducting the breeding on behalf of the applicant's laboratory. Rats used are males aged 3 months±1 week.

Tumor induction by PROb cell injection:

PROb Cell origin: DHD/K12 cell line was initially derived from a graft of a colon carcinoma fragment induced in an in-bred BDIX rat by 1,2-dimethylhydrazine treatment. This line of adherent cells was subdivided into two sublines depending on their sensitivity to trypsin treatment, and cells which are hard to break-off were given the name of DHD/K12-TR. DHD/K12-TR cells when injected in syngenic BDIX rats give rise to steady-developing tumors. This line has been cloned, only DHD/K12-TRb clone referred to as PROb was used in the present investigation.

Culture conditions: Adherent PROb cells were cultured in sealed bottles (Falcon, Becton Dickinson, N.J., USA) at 37° C. in complete medium made up of Ham's F10 medium (Bio-Whittaker, Walkersville, USA) to which 10% foetal calf serum (FCS, Anval, Betton, France) were added. Replacement of culture medium was done every 3 days. Upon reaching confluency, cells were released or scraped off within 3 to 5 min from the support by 2 ml of EDTA/trypsin solution, following 3 rinses with 2 ml of the same solution for 2–3 minutes; cells were resuspended into whole medium, with addition of FCS to stop trypsin action. The absence of contamination in cells of mycoplasma and bacterial origin was checked at regular intervals by DNA dyeing with Hoechst fluorochrome 33258 (Aldrich Chimie, Steinheim, GFR).

Induction of peritoneal carcinoma: PROb cells are released from their support as set forth in "culture conditions" section and are counted in a trypan blue coloring agent solution as a means for assessing cell viability. Cells are suspended in Ham's F10 medium. Peritoneal carcinomas are induced by intraperitoneal injection (i.p.) of $10^6$ viable PROb cells into a syngenic BDIX rat under ether anesthesia. Tumor cell injection is done on Day 10. In these conditions, all rats develop a peritoneal carcinoma with production of bloody ascites and die between the $6^{th}$ day and the $12^{th}$ day following cell injection.

Treatment of peritoneal carcinoma: Treatment is initiated 13 days after injection of tumoral cells when carcinoma masses are made up of nodules of a few mm in diameter. Treatment is administered by 10 i.v. injections of OM-294-DP at a rate of 1 mg/kg of body weight and in doses of 0.6 mg/ml dissolved in 0.9% NaCl solution. Injections are administered 3 times a week (monday, Wednesday and friday) in the penile vein. Control group is treated with vehicle alone i.e. 0.9% NaCl.

Assessing treatment efficiency: At D42, 6 weeks after injecting tumor cells, rats are killed and dissected, carcinoma development is assessed through a blind study. Measuring carcinoma volume is not feasable, instead, it is possible to classify carcinomas into 4 different types. Five classes are defined according to the number and diameter of nodules.

Class 0: No nodules are visible

Class 1: Nodules of 0.1 to 0.2 cm in diameter are readily counted

Class 2: Countless nodules of 0.1 to 0.5 are seen

Class 3: Peritoneal cavity is invaded by nodules, some of which measure 1 cm in diameter.

Class 4: Cavity is completely invaded with tumor masses of a few cm in size.

Ascite volume and animal weight change: Ascite volume is measured by weighing animals twice. A group of control rats, to which no treatment but only 0.9% NaCl injections had been administered, allows normal development of carcinomas to be assessed and treatment follow-up.

Assessing treatment efficiency: Survival rate of rats in treated groups is compared to survival rate in control groups; carcinoma and ascite volumes of rats in treated groups are compared to measurements derived from rats in the control group.

Statistical analysis: Statistical significance of immunotherapy effect is determined using Kruskal-Wallis test for classifying carcinomas. Likewise, a variance analysis test is conducted for ascite volume data, and a log rank test is performed for survival rates.

Results

Carcinomas: OM-294-DP shows a remarkable anti-tumor activity in this model. This activity is more specifically demonstrated by the number of tumor-free animals (class 0) and further the difference with NaCl control is significant ($p<0.05$) for tumor volume. Impact of treatment with OM-294-DP on ascite volume is also significant ($p<0.05$).

TABLE (a)

Carcinoma classification and ascite volume

| Treatment | Number of rats suffering from carcinoma belonging to class | | | | | Effect of product (*) | Volume ascite in ml/rat | | Effect of product (**) |
|---|---|---|---|---|---|---|---|---|---|
| | 0 | 1 | 2 | 3 | 4 | | range | mean ± σ | |
| NaCl[1] | 1 | 0 | 1 | 0 | 7 | — | 0–84 | 38 ± 29 | — |
| OM-294-DP[2] | 4 | 1 | 2 | 1 | 2 | $p < 0.05$ | 0–73 | 8 ± 23 | $p < 0.05$ |

(*): Kruskall-Wallis test, (**): Variance analysis.
[1]8 to 10 rats died from cancer before being killed, 1 rat at D34 displayed nodules and jaundice but no accurate class determination could be made (cannibalism), 1 rat at D37 belonged to (class 4), 2 at D38 belonged to (class 4); 1 at D39 belonged to (class 4), 2 at D40 belonged to (class 4) and 1 at D41 belonged to (class 4). One rat of class 0 displayed upon dissection a subcutaneous tumor, it is likely that injection of cancer cells failed.
[2]1 rat died at D14 at the time of the first treatment injection, the latter did not suffer from carcinoma. One of the rats killed in class 0 showed a subcutaneous tumor (injection of cancer cells failed).

Survival:

Animals are killed at D42. Survival was determined at day 42 following injection of tumor cells, 90% of animals treated with OM-294-DP survived, whereas for the untreated group only 20% of animals were still alive.

Rat survival rate is significantly extended by OM-284-DP ($p<0.001$).

Weight: OM-294-DP has no significant effect on weight change in comparison to animals administered NaCl alone as demonstrated by data in Table (b).

TABLE (b) Weight change in rats (mean ± standard deviation)

| Days | NaCl | OM-294-DP |
|---|---|---|
| 0 | 314 ± 19 | 277 ± 19 |
| 13 | 337 ± 18 | 310 ± 21 |
| 20 | 342 ± 20 | 304 ± 23 |
| 29 | 361 ± 23 | 317 ± 24 |
| 41 | 314 ± 38 | 327 ± 26 |

11. Evaluation of OM-294-DP Adjuvant Properties in a Murine Immunization Model Through Nasal Administration of Urease B Subunit of *Heliobacter pylori*

It has been shown that mice can be protected from *Heliobacter pylori* infection when immunized with urease B subunit of *Heliobacter pylori* either by oral or nasal administration in presence of a cholera toxin (CT) based adjuvant. Corthésy-Teulaz I., et al., *Gastroenterology*, 109: (1995): 115; Michetti P. et al., *Gastroenterology*, 116: (1999) 804; Saldinger P. F. et al., *Gastroenterology* 115: (1998) 891. This anti-Ure B humoral response as measured in serum of immunized mice is mainly of the IgG1 type (Th2 response). Adjuvant effect evaluation of OM-294-DP is conducted in BALB/c mice (n=6) immunized four times at intervals of one week by nasal administration of urease B subunit (UreB) of recombinant *Heliobacter pylori* in presence of OM-294-DP. BALB/c control mice were immunized with OM-294-DP adjuvant alone. Two weeks following the last booster, blood is sampled from each mouse to assay serum anti-UreB immunoglobulins by ELISA (total IgG, IgG1 and IgG2a).

Procedure

Animals: BALB/c/Ola/HsD mice (Harland, Horst, Netherlands): 24 mice.

Antigen: HpUreB 1-569, expressed as recombinant protein in *E. coli* (M15 strain, Qiagen, Hilden, GFR) according to a previously described method (Michetti et al., *Gastroenterology*, 107: (1994) 1002).

Adjuvant: OM-294-DP (2.2 mg/ml stock solution)

Immunization Regimen:

Four groups containing 6 mice each were formed:

Groups A: 6 BALB/c mice were immunized four times by nasal administration of 25 µg of OM-294-DP alone (25 µl per dose) once a week throughout 4 consecutive weeks.

Group B: 6 BALB/c mice were immunized four times by nasal administration of 50 µg of Ure B 1-569+25 µg OM-294-DP (25 µl per dose) once a week throughout 4 consecutive weeks Two weeks after the last nasal route immunization, blood was sampled by tail puncture from each mouse in groups A & B.

Assay for serum IgG:

Coating buffer (pH 9.6): per 1 liter, $Na_2CO_3$ (15 mM, 1.59 g), $NaHCO_3$ (34.8 mM, 2.93 g), Thimerosal (0.01%); PBS-Tween Buffer pH 7.4: per 1 liter, NaCl (137 mM, 8.0 g), $KH_2PO_4$ (1.5 mM, 0.2 g), $Na_2HPO_4$ (8.0 mM, 1.15 g), KCl (2.7 mM, 0.2 g), Tween 20 (0.1% 1 ml); Citrate/phosphate buffer pH 5.0: per 1 liter, citric acid (44.4 mM, 9.32 g), $Na_2 HPO_4$ (103 mM, 14.6 g); Substrate solution 10× (O-phenyldiamine =OPD) (10-fold concentrated.): (10 mg/ml in citrate buffer); Sodium azide solution: 1%, Stop solution: 0.01% sodium azide in citrate/phosphate buffer 0.1 M pH 5.0

Method: An antigen solution (UreB 1-569 prepared on May 26th, 1999, 0.5 mg/ml stock solution) is prepared at a concentration of 5 µg/ml in coating buffer pH9.6 (500 µl of UreB solution per 50 ml of buffer). 100 µl are pipetted into each well in 3 round bottom 96-well plates (0.5 µg UreB per well). The plates are incubated for 2 hours at 37° C. Supernatant fluids are discarded from the plates. Wells are blocked by adding 100 µl of PBS-0.1% Tween solution+5% milk powder per well. Plates are incubated for 30 minutes at 37° C. The blocking solution is discarded and wells are washed 3 times with 100 µl of PBS-Tween. Supernatant fluids are discarded. A 1:200 dilution of each mouse serum to be tested is prepared in PBS-0.1% Tween buffer (5 µl of serum in 1 ml of PBS-Tween). Sera (100 µl) are divided in duplicates into three plates (1 plate to detect total IgG, 1 plate to detect IgG1 and 1 plate to detect IgG2a). Incubation is carried out overnight at 4° C. Wells are washed 3 times with 100 µl of PBS-Tween. A 1:500 dilution of biotin-coupled-anti-IgG total antibody (Amersham, Cat # RPN 1177), anti-IgG1 antibody (Amersham Cat # RPN 1180) and anti-IgG2a antibody solutions (Pharmingen Cat #~02012D) in PBS-Tween buffer is individually prepared. 100 µl of the anti-IgG total antibody solution are added to plate No 1, 100 µl of the anti-IgG1 solution to plate No 2 and 100 µl of the anti-IgG2a antibody solution to plate No 3. Incubation is carried out for 1 hour at 37° C. Wells are washed 3 times with PBS-Tween. A 1:1000 dilution of streptavidin-HRP (Dako, Cat # p0397) is prepared in PBS-Tween buffer and 100 µl of the solution are added per well. Incubation is carried out for 1 hour at 37° C. The wells are washed 3 times with PBS-Tween buffer. A substrate solution is prepared by diluting 10-fold the OPD solution (10x) in 0.1 M citrate/phosphate buffer. 1 µl of $H_2O_2$ is added to the dilute OPD solution. 50 µl of the substrate solution are added to each well. Color development is allowed to occur for 10 to 20 minutes. The reaction is terminated by adding 50 µl of stop buffer. Absorbance is read at 492 nm (with a standard being read at 620 nm) using a negative control as blank.

Statistical analysis: Data stand for mean±SD (n=6). p values are derived from t-Student test. Data significance level is set at p<0.05.

Results

Previously immunized mice with UreB-1-569+ OM-294-DP through nasal route administration develop an anti-UreB humoral immunity: anti-UreB 1-569 IgG1 are present in the blood.

Presence of antibodies specifically directed against UreB of Hp in mouse serum is measured by ELISA. UreB (0.5 µg/well) is dispensed into round bottom 96-well plates together with carbonate buffer pH 9.6. Specific antibodies are detected by means of rabbit anti-IgG total antibodies, anti-IgG1 and IgG2a antibodies. Results are given as optical density (OD) reading at 492 nm. OD values 3 times greater than measured values in serum of naive mice are considered positive. No anti-UreB antibodies are detected in the serum of mice immunized with OM-294-DP alone. Mice which have been immunized with Ure+OM-294-DP also develop total anti-UreB IgG antibodies (OD=0.274±0.130, p<0.05) and anti-UreB IgG1 (OD=0.212±0.128, p<0.05), but do not develop anti-UreB IgG2a antibodies (OD=0.008+0.005, non significant).

BALB/c mice immunized with urease B subunit of *Heliobacter pylori* by nasal administration (UreB)+OM-294-DP develop an anti-UreB humoral response mainly of the IgG1 type. OM-294-DP can therefore act as an adjuvant by nasal route administration and promote development of a humoral immunity of the Th2 type.

12. OM-294-MP and OM-294-DP in Combination with H1N1 Antigen: Determining Specific Antibodies Raised in Mice after 1 or 2 Subcutaneous Administrations Procedure This study is aimed at demonstrating the adjuvant effect of OM-294-MP and OM-294-DP for influenza antigen H1N1 (262195 A/B Beijing haemagglutinin, Solvay Duphar, Weesp, NL). To this end, 60 BALB/c mice (females, 8 weeks-old at the beginning of treatment) are divided in 6 groups as follows:

| Groups | Antigen Final conc.: 2.5 µg per animal/injection | Adjuvants Final conc.: 50 µg per animal/injection | NaCl (0.9%) | Injected volume |
|---|---|---|---|---|
| A: NaCl | — | — | 150 µl | 150 µl |
| B: H1N1 | H1N1 (100 µl) | — | 50 µl | 150 µl |
| C: H1N1 + OM-294-MP | H1N1 (100 µl) | OM-294-MP (50 µl) | — | 150 µl |
| D: H1N1 + OM-294-DP | H1N1 (100 µl) | OM-294-MP (50 µl) | 100 µl | 150 µl |
| E: OM-294-MP | — | OM-284-MP (50 µl) | 100 µl | 150 µl |
| F: OM-294-DP | — | OM-284-DP (50 µl) | 100 µl | 150 µl |

Antigen: H1N1 stock solution is prepared at a concentration of 25 µg/ml in 0.9% NaCl.

Adjuvants: Stock solutions of OM-294-DP and OM-294-MP are prepared at a concentration of 1 mg/ml in injection water, with 0.1% triethanolamine being added to OM-294-MP. The negative control consists of a 0.9% NaCl solution without antigen.

Antigen-adjuvant mixture: Adjuvants are kept for 20 minutes at 37° C. before vortexing for 3 minutes. Then, the antigen and NaCl (0.9%) are added as stated in the Table given above, and the antigen-adjuvant mixture is vortexed briefly before placing it on a rotary stirrer for 15 minutes at room temperature, and finally the whole mixture is vortexed for 3 minutes.

Immunization regimen: Injections are scheduelled on days 0 and 14. Mixtures indicated in the aforementioned Table are administered by subcutaneous route (75 µl on the side, with a total 150 µl per animal). Blood sampling is scheduelled on days 14 and 18 (orbital punctures).

Assay for anti-H1N1 immunoglobulins: The following serum Immunolglobulins which are specifically directed against H1N1 are assayed in duplicate by ELISA: IgG1, IgG2a, and IgM. Briefly stated, microtiter plates (NUNC Immunoplate, Roskilde, DK) are incubated (overnight coating) at 4° C. with 100 µl H1N1 (0.5 µg) in bicarbonate buffer pH 9.6). After washing with 0.5% Tween-20 (Merck Hohenbrunn, D), sera are diluted 50-, 200- and 800-fold (diluting solution: phosphate buffered saline (PBS)+1% bovine serum albumin (BSA, Sigma, St. Louis, Mo., USA)+0.02% Tween-20)). 100 µl of each dilute serum sample are added to the wells. Incubation lasts 45 minutes at 37° C.

After a second washing step, IgG1, IgG2a and IgM specifically directed to $H_1N_1$ are incubated for 30 minutes at 37° C. together with 100 µl of anti-IgG1 antibodies (anti-mouse rat antibody)-peroxydase conjugate (Serotec, Oxford, UK), IgG2a-peroxydase conjugate (Pharmingen, San Diego, Calif., USA) and IgM-biotin conjugate (Pharmingen, San Diego, Calif., USA), diluted beforehand in PBS/BSA/Tween buffer (250-, 1000-, 500-fold dilutions, respectively). For IgM, after an extra washing step, a $3^{rd}$ incubation is required (30 min. at 37° C.) with a 1:100 dilute solution of streptavidin-peroxydase conjugate (Dako, Glostrup, DK).

After the washing step, 100 µl of a phenylene 1,2-diamine solution (OPD, Merck, Darmstadt, GFR) are added to detect peroxydase-coupled anti-IgG1 and anti-IgG2 secondary antibodies (whereas for IgM, the reagent being used is 3', 3', 5',5'-tetramethylbenzidine (TMB, Sigma, St. Louis, Mo., USA). After a 20 minute incubation period at room temperature, the reaction is stopped by adding 100 µl of 2N $H_2SO_4$. Absorbance values are read at 490 nm with a Bio-Rad 3550 model plate reader.

Results

Results of each reading at 490 nm are given in arbitrary units (A.U.) per ml. This is achieved by comparing each sample with a standard prepared from variable dilutions of a sample pool collected from group B (animals injected with H1N1 alone) at day 28. As the term implies, the sample pool diluted 50-fold is at a concentration of 1000 A.U./ml. Individual results are then corrected for the corresponding dilution factor (50, 200, or 800 times). Only the mean values of each group and the standard deviation (SD) are herein reported.

TABLE a) Immunoglobulins specifically raised again H1N1 of IgG1 subclass (Arbitrary units/ml ± SD, **p < 0.01 (Anova & (two sided) Dunnetts tests).

| Groups | Day 14 | Day 28 |
|---|---|---|
| A: NaCl | 3 ± 5 | 0 ± 0 |
| B: H1N1 | 11161 ± 5755 | 53950 ± 23403 |
| C: H1N1 + OM-294-MP | 34411 ± 13719 | 228467** ± 109123 |
| D: H1N1 + OM-294-DP | 30101 ± 19061 | 382325** ± 201314 |
| E: OM-294-MP | 69 ± 34 | 59 ± 31 |
| F: OM-294-DP | 59 ± 21 | 38 ± 25 |

TABLE b) Immunoglobulins specifically raised against H1N1 of IgG2a subclass (Arbitrary units/ml ± SD, **p < 0.01 (Anova & (two sided) Dunnetts tests).

| Groups | Day 14 | Day 28 |
|---|---|---|
| A: NaCl | 0 ± 0 | 0 ± 0 |
| B: H1N1 | 26883 ± 20779 | 50352 ± 30846 |
| C: H1N1 + OM-294-MP | 179344** ± 139781 | 1622722** ± 986195 |
| D: H1N1 + OM-294-DP | 103630 ± 96257 | 681441 ± 1072710 |
| E: OM-294-MP | 1619 ± 743 | 1767 ± 1034 |
| F: OM-294-DP | 452 ± 584 | 782 ± 857 |

TABLE c) Immunoglobulins specifically raised against H1N1 of IgM subclass (Arbitrary units/ml ± SD, *p < 0.05 & **p < 0.01 (Anova & (two sided) Dunnetts tests).

| Groups | Day 14 | Day 28 |
|---|---|---|
| A: NaCl | 22102 ± 5862 | 21531 ± 3693 |
| B: H1N1 | 37787 ± 15001 | 57306 ± 26886 |
| C: H1N1 + OM-294-MP | 67936** ± 21334 | 95108 ± 38669 |
| D: H1N1 + OM-294-DP | 598100* ± 18324 | 92920 ± 26971 |
| E: OM-294-MP | 19065 ± 4069 | 18018 ± 1016 |
| F: OM-294-DP | 20756 ± 7160 | 20944 ± 9065 |

Figure 22:
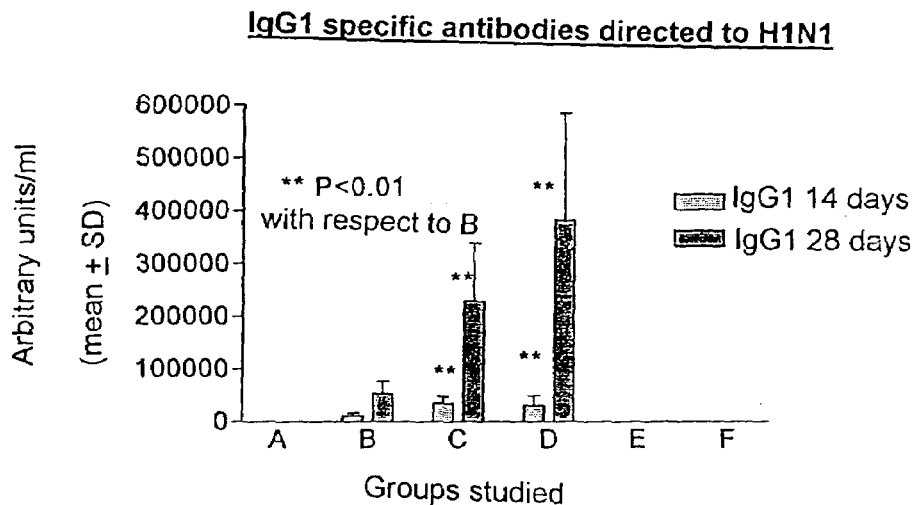
FIGS. 22 to 29 are graphs of specific mouse antibodies directed to specific antigens.
Figure 23:
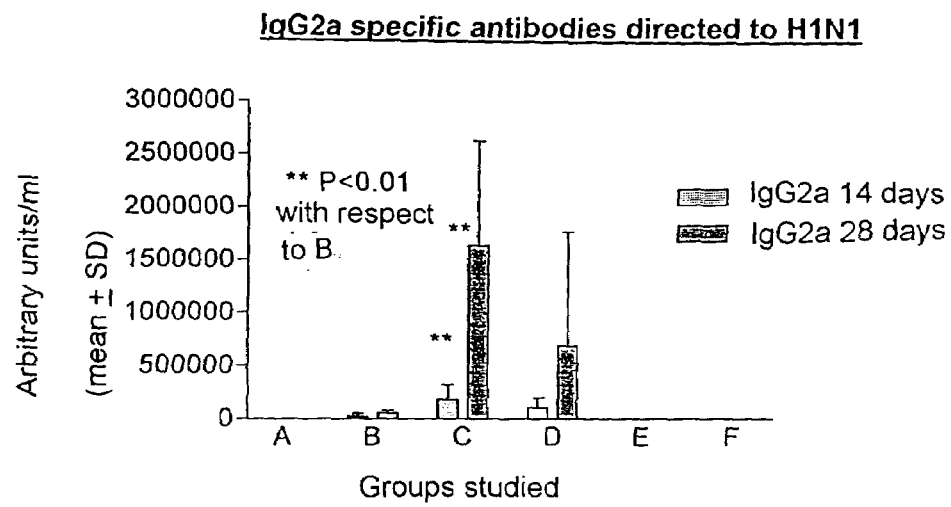
Figure 24:
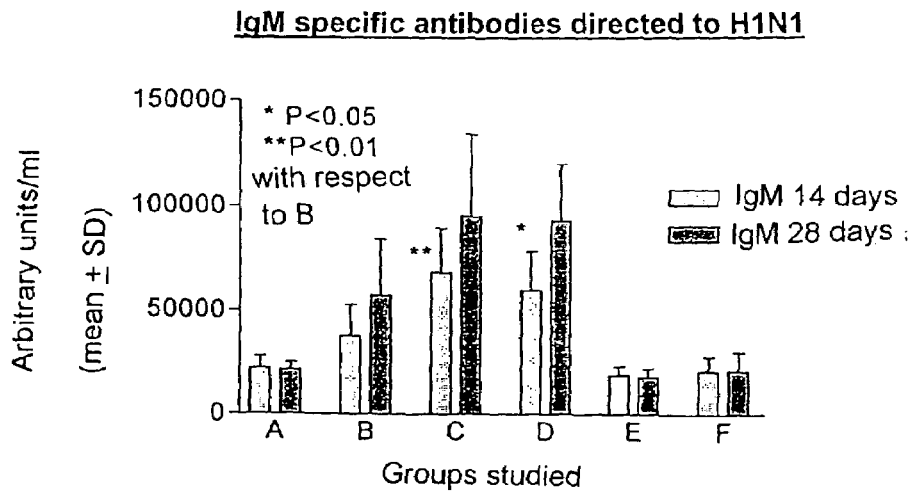

These results indicate that OM-294-MP and OM-294-DP adjuvants are active in the model under investigation, since they both significantly increase the titer of antibodies specifically raised against H1N1 in mice after one or two injections (see FIGS. 22, 23, 24), irrespective of the immunoglobulin subclass being considered (IgG1a, IgG2a and IgM).

13. OM-294-OM and OM-294-DP in Combination with Ovalbumin Antigen: Determining Specific Antibodies Raised in Mice after 1 or 2 Subctuaneous Administrations Procedure This study is aimed at demonstrating the adjuvant effect of OM-294-MP and OM-294-DP with regard to ovalbumin antigen (Fluka Chemie, Buchs, Switzerland). To this end, 50 BALB/c mice (females, aged 8 weeks at the beginning of treatment) were divided into 5 groups as follows:

| Groups | Antigen Final conc.: 50 µg per animal/injection | Adjuvants Final conc.: 50 µg per animal/injection | NaCl | Injected volume |
|---|---|---|---|---|
| A: NaCl | — | — | 150 µl | 150 µl |
| B: Ova | Ova (100 µl) | — | 50 µl | 150 µl |
| C: Ova + OM-294-MP | Ova (100 µl) | OM-294-MP (50 µl) | — | 150 µl |
| D: Ova + OM-294-DP | Ova (100 µl) | OM-294-DP (50 µl) | — | 150 µl |
| E: OM-294-MP | — | OM-294-MP (50 µl) | 100 µl | 150 µl |

Antigen: An ovalbumin stock solution is prepared at a concentration of 0.5 mg/ml in 0.9% NaCl.

Adjuvants: Stock solutions of OM-294-DP and OM-294-MP are prepared at a concentration of 1 mg/ml in water for injection, with 0.1% triethanolamine being added for OM-294-MP. The negative control consists of a 0.9% NaCl solution without antigen.

Antigen-Adjuvant mixture: Adjuvants are allowed to stand for 20 minutes at 37° C. before vortex treatment for 3 minutes. Then the antigen and (0.9%) NaCl are added as specified in the above Table, and the antigen/adjuvant mixture is vortexed briefly before placing it on a rotary stirrer for 15 minutes at room temperature, then the whole mixture is vortexed for 3 minutes.

Immunization regimen: Injections are scheduelled on days 0 and 14. The mixtures stated in the preceeding table are administered by subcutaeous route (75 µl on the side, 150 µl in total per animal). Blood sampling is scheduelled on days 14 and 28 (orbital puncture).

Assay for anti-ovalbumin immunoglobulins: The following serum Immunolglobulins which are specifically directed against ovalbumin are assayed in duplicate by ELISA: IgG1, IgG2a, and IgM. Briefly stated, microtiter plates (NUNC Immunoplate, Roskilde, DK) are incubated (overnight coating) at 40C together with 100 µl ovalbumin (0.5 µg) in bicarbonate buffer pH 9.6). After washing with 0.5% Tween-20 (Merck Hohenbrunn, D), sera are diluted 50-, 200- and 800-fold (diluting solution: phosphate buffered saline (PBS)+1% bovine serum albumin (BSA, Sigma, St. Louis, Mo., USA)+0.02% Tween-20)). 100 µl of each dilute serum sample are added to the wells. Incubation lasts 45 minutes at 37° C.

After a second washing step, IgG1, IgG2a and IgM specifically directed to ovalbumin are incubated for 30 minutes at 37° C. together with 100 µl of anti-IgG1 antibodies (anti-mouse rat antibody)-peroxydase conjugate (Serotec, Oxford, UK), IgG2a-peroxydase conjugate (Pharmingen, San Diego, Calif., USA) and IgM-biotin conjugate (Pharmingen, San Diego, Calif., USA), diluted beforehand in PBS/BSA/Tween buffer (250-, 1000-, 500-fold dilutions, respectively). For IgM, after an extra washing step, a $3^{rd}$ incubation step is required (30 min. at 37° C.) with a 1:100 dilute solution of streptavidin-peroxydase conjugate (Dako, Glostrup, DK).

After the washing step, 100 µl of a phenylene 1,2-diamine solution (OPD, Merck, Darmstadt, GFR) are added to detect peroxydase-coupled anti-IgG1 and anti-IgG2 secondary antibodies (whereas for IgM, the reagent being used is 3', 3', 5',5'-tetramethylbenzidine (TMB, Sigma, St. Louis, Mo., USA). After a 20 minute incubation period at room temperature, the reaction is stopped by adding 100 µl of 2N $H_2SO_4$. Absorbance values are read at 490 nm with a Bio-Rad 3550 model plate reader Results Results of each reading at 490 nm are given in arbitrary units (A.U.) per ml. This is achieved by comparing each sample with a standard prepared from different dilutions of a sample pool collected from group B at day 28 (animals injected with ovalbumin alone). As clearly understood by this term, the sample pool diluted 50-fold is at a concentration of 1000 A.U./ml. Individual results are then corrected for the corresponding dilution factor (50, 200, or 800 times). Only the mean values of each group and the standard deviation (SD) are herein reported.

TABLE a) Immunoglobulins specifically raised against ovalbumin of IgG1 subclass (Arbitrary units/ml ± SD **p < 0.01 (Anova & (two sided) Dunnetts tests).

| Groups | Day 14 | Day 28 |
| --- | --- | --- |
| A: NaCl | 6 ± 6 | 16 ± 12 |
| B: ova | 728 ± 589 | 47743 ± 46294 |
| C: ova + OM-294-MP | 4361** ± 2513 | 284121** ± 164822 |

TABLE-continued a) Immunoglobulins specifically raised against ovalbumin of IgG1 subclass (Arbitrary units/ml ± SD **p < 0.01 (Anova & (two sided) Dunnetts tests).

| Groups | Day 14 | Day 28 |
| --- | --- | --- |
| D: ova + OM-294-DP | 3240** ± 1794 | 277025** ± 173737 |
| E: OM-294-MP | 19 ± 8 | 40 ± 69 |

Table b) Immunoglobulins specifically raised against ovalbumin of IgG2a subclass (Arbitrary units/ml ± SD, *p < 0.05 **p < 0.01 (Anova & (two sided) Dunnetts tests).

| Groups | Day 14 | Day 28 |
| --- | --- | --- |
| A: NaCl | 2996 ± 898 | 5414 ± 1554 |
| B: ova | 5201 ± 1880 | 73162 ± 107954 |
| C: ova + OM-294-MP | 9524 ± 6809 | 625663* ± 681232 |
| D: ova + OM-294-DP | 18108** ± 14958 | 601434* ± 624166 |
| E: OM-294-MP | 11253 ± 12169 | 4192 ± 2104 |

Table c) Immunoglobulins specifically raised against ovalbumin of IgM subclass (Arbitrary units/ml ± SD)

| Groups | Day 14 | Day 28 |
| --- | --- | --- |
| A: NaCl | 14009 ± 6158 | 12288 ± 7136 |
| B: ova | 19423 ± 13778 | 47998 ± 34035 |
| C: ova + OM-294-MP | 21652 ± 9524 | 38240 ± 8822 |
| D: ova + OM-294-DP | 25762 ± 10975 | 74399 ± 119781 |
| E: OM-294-MP | 19742 ± 5667 | 9827 ± 2021 |

Figure 25:
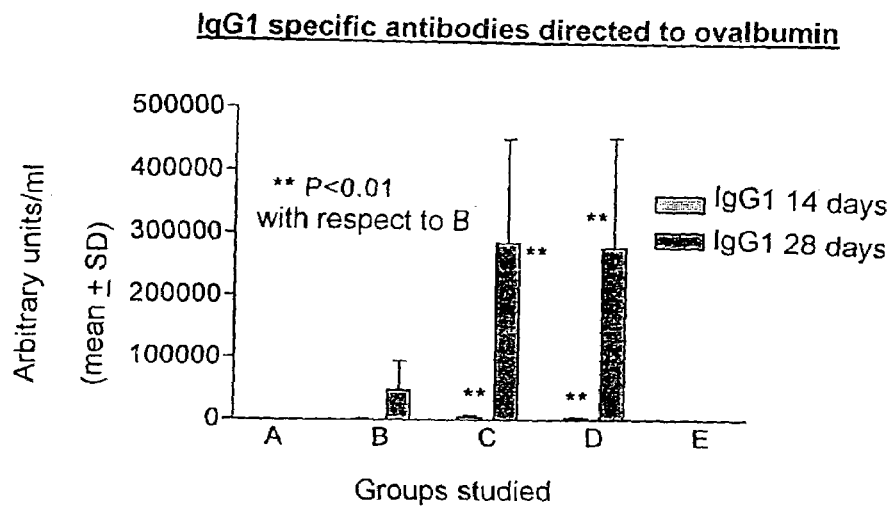
Figure 26:
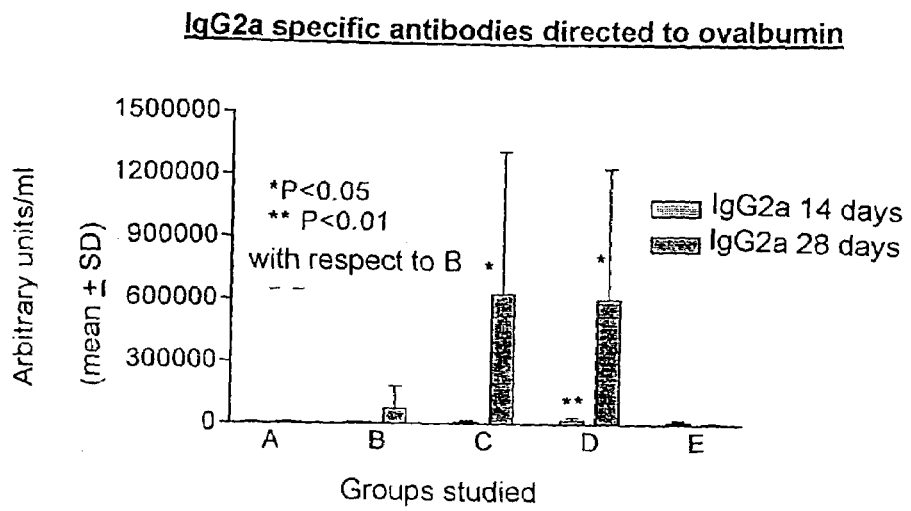
Figure 27:
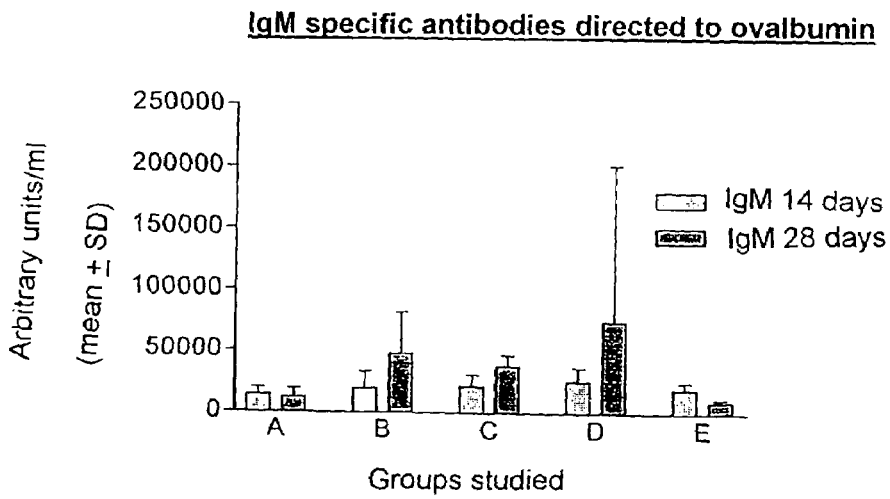

These results indicate that OM-294-MP and OM-294-DP adjuvants are active in the present model under investigation, since they both significantly increase (with respect to IgG1 and IgG2a subclasses) the titer of antibodies specifically raised against ovalbumin in mice after one or two injections (see FIGS. 25, 26, 27).

14. OM-294-MP and OM-294-DP in Combination with TT Antigen (Tetanos Toxoid): Determining Specific Antibodies Raised in Mice after 1 or 2 Subcutaneous Administrations Procedure This study is aimed at demonstrating the adjuvant effect of OM-294-MP and OM-294-DP for TT antigen (Massachussetts Biologic Laboratoires, MA, USA). To this end, 40 BALB/c mice (females, 8 weeks-old at the beginning of treatment) are divided into 4 groups as follows:

| Groups | Antigen Final conc.: 50 µg per animal/injection | Adjuvants Final conc.: 50 µg per animal/injection | NaCl (0.9%) | Injected volume |
| --- | --- | --- | --- | --- |
| A: NaCl | — | — | 150 µl | 150 µl |
| B: TT | TT (100 µl) | — | 50 µl | 150 µl |
| C: TT + OM-294-MP | TT (100 µl) | OM-294-MP (50 µl) | — | 150 µl |
| D: TT + OM-294-MP | TT (100 µl) | OM-294-DP (50 µl) | — | 150 µl |

Antigen: A TT stock solution is prepared at a concentration of 0.2 mg/ml in 0.9% NaCl.

Adjuvants: Stock solutions of OM-294-DP and OM-294-MP are prepared at a concentration of 1 mg/ml in water for injection, with 0.1% triethanolamine being added for OM-294-MP. The negative control consists of a 0.9% NaCl solution without antigen.

Antigen-Adjuvant mixture: Adjuvants are allowed to stand for 20 minutes at 37° C. before vortex treatment for 3 minutes. Then the antigen and (0.9%) NaCl are added as specified in the above Table, and the antigen/adjuvant mixture is vortexed briefly before placing it on a rotary stirrer for 15 minutes at room temperature, then the whole mixture is vortexed for 3 minutes.

Immunization regimen: Injections are scheduelled on days 0 and 14. The mixtures stated in the preceeding table are administered by subcutaeous route (75 µl on the side, 150 µl in total per animal). Blood sampling is scheduelled on days 14 and 28 (orbital puncture).

Assay for anti-TT immunoglobulins: The following serum Immunolglobulins which are specifically directed against TT are assayed in duplicate by ELISA: IgG1, IgG2a, and IgM. Microtiter plates (NUNC Immunoplate, Roskilde, DK) are incubated (overnight coating) at 4° C. together with 100 µl TT (0.5 µg) in bicarbonate buffer (pH 9.6). After washing with 0.5% Tween-20 (Merck Hohenbrunn, D), sera are diluted 50-, 200- and 800-fold (diluting solution: phosphate buffered saline (PBS)+1% bovine serum albumin (BSA, Sigma, St. Louis, Mo., USA)+0.02% Tween-20)). 100 µl of each dilute serum sample are added to the wells. Incubation lasts 45 minutes at 37° C.

After a second washing step, IgG1, IgG2a and IgM specifically directed to ovalbumin are incubated for 30 minutes at 37° C. together with 100 µl of anti-IgG1 antibodies-peroxidase conjugate (Serotec, Oxford, UK), IgG2a-peroxydase conjugate (Pharmingen, San Diego, Calif., USA) and IgM-biotin conjugate (Pharmingen, San Diego, Calif., USA), diluted beforehand in PBS/BSA/Tween buffer (250-, 1000-, 500-fold dilutions, respectively). For IgM, after an extra washing step, a 3$^{rd}$ incubation step is required (30 min. at 37° C.) with a 1:100 dilute solution of streptavidin-peroxidase conjugate (Dako, Glostrup, DK).

After the washing step, 100 µl of a phenylene 1,2-diamine solution (OPD, Merck, Darmstadt, GFR) are added to detect peroxydase-coupled anti-IgG1 and anti-IgG2 secondary antibodies (whereas for IgM, the reagent being used is 3', 3', 5',5'-tetramethylbenzidine (TMB, Sigma, St. Louis, Mo., USA). After a 20 minute incubation period at room temperature (40 min. for TMB), the reaction is stopped by adding 100 µl of 2N $H_2SO_4$. Absorbance values are read at 490 nm with a Bio-Rad 3550 model plate reader Results Results of each reading at 490 nm when measuring IgG1 and IgG2a are given in arbitrary units (A.U.) per ml. This is achieved by comparing each sample with a standard prepared from different dilutions of a sample pool collected from the group B at day 28 (animals injected with TT alone). As this term implies, the sample pool diluted 50-fold is at a concentration of 1000 A.U./ml. Individual results are then corrected for the corresponding dilution factor (50, 200, or 800 fold). Only the mean values of each group and the standard deviation (SD) are herein reported.

Regarding the assay of IgM specific for TT, since the "background noise" of the assay was too high, no clear cut difference could be found between group B (TT alone) and groups C and D (TT with adjuvant) by measuring specific IgM as previously done for IgG1 and IgG2a. Instead, specific IgM titer could be determined, using successive dilutions of each sample (rather than A.U. described before) and the result was reported, for each sample, as the highest dilution which gives an absorbance reading greater than mean absorbance±3 SD for group A (NaCl). The titer thus obtained indicates the number of times a serum sample can be diluted before the absorbance thereof could no longer be distinguished from background noise level. This final dilution is the result reported in Table (c) for IgM given hereinafter.

Table (a) Immunoglobulins specifically raised against TT of IgG1 subclass (Arbitrary units/ml ± SD, **p < 0.01 (Anova & (two sided) Dunnetts tests)).

| Groups | Day 14 | Day 28 |
|---|---|---|
| A: NaCl | 1 ± 2 | 0 ± 1 |
| B: TT | 2871 ± 1633 | 34367 ± 15018 |
| C: TT + OM-294-MP | 8502** ± 2020 | 78506** ± 21660 |
| D: TT + OM-294-DP | 11620** ± 2348 | 136463** ± 41025 |

Table (b) Immunoglobulins specifically raised against TT of IgG2a subclass (Arbitrary units/ml ± SD, **p < 0.01 (Anova & (two sided) Dunnetts tests).

| Groups | Day 14 | Day 28 |
|---|---|---|
| A: NaCl | 351 ± 506 | 536 ± 1046 |
| B: TT | 2547 ± 2539 | 61387 ± 82269 |
| C: TT + OM-294-MP | 8869 ± 6979 | 65881 ± 46635 |
| D: TT + OM-294-DP | 21969** ± 25067 | 148365 ± 134196 |

Table (c) Titer of immunoglobulins specifically directed against TT of IgM subclass (dilutions for each sample giving a signal at 490 nm greater than the mean ± 3 SD for a sample dilution In group A).

| Groups | Day 14 | Day 28 |
|---|---|---|
| A: NaCl | standard | standard |
| B: TT | 9 animals < 25<br>1 animal < 50 | 10 animals < 25 |
| C: TT + OM-294-MP | 9 animals < 25<br>1 animal > 1600 | 7 animals < 25<br>1 animal < 100<br>2 animals > 1600 |
| D: TT + OM-294-DP | 7 animals < 25<br>1 animal < 200<br>2 animals > 1600 | 10 animals < 25 |

Figure 28:
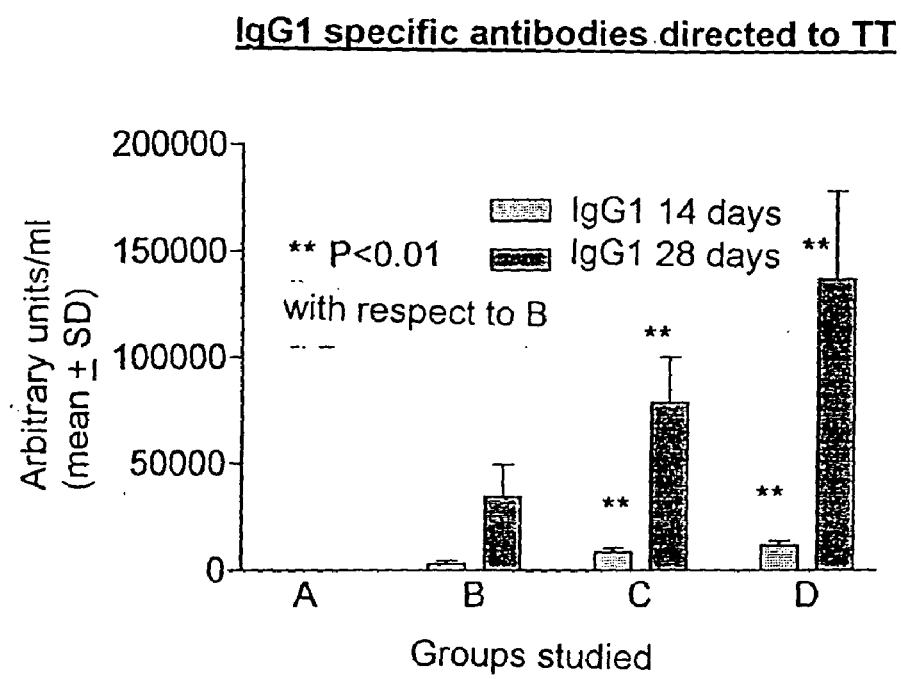
Figure 29:
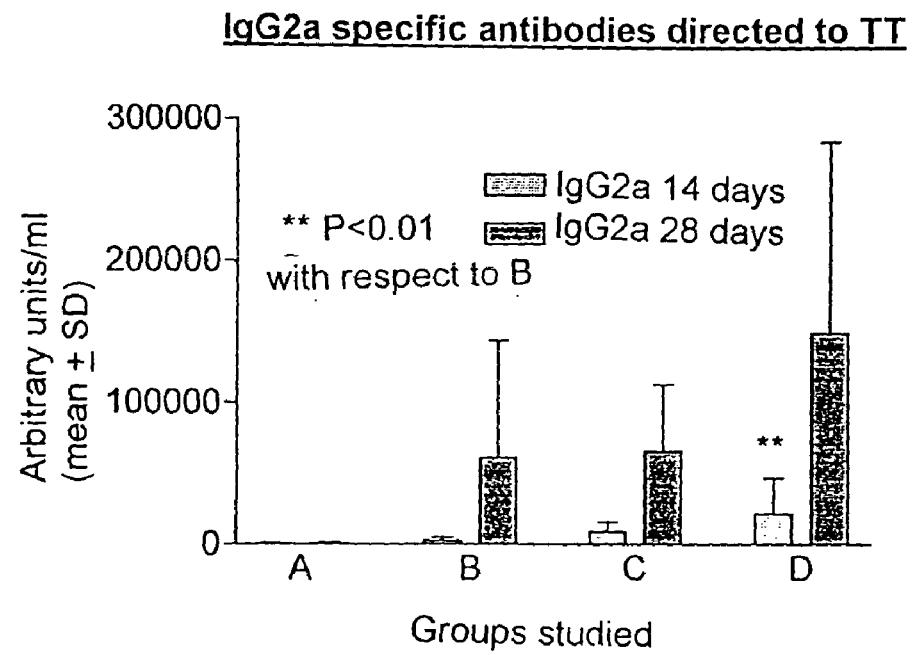

These results indicate that adjuvants OM-294-MP and OM-294-DP are active in the present model under investigation, since they both often significantly increase the titer of IgG1 and IgG2a antibodies specifically raised against TT in mice after one or two injections (see FIGS. 28, 29). By contrast, only a few animals produced IgM specific to TT.

15. Evaluation of the Adjuvant Properties of OM-294-MP in a CBA Mouse Immunization Model by Subcutaneous Administration of *Leishmania* gp63 Antigen.

Procedure

CBA mice are administered in the tail two subcutaneous injections of gp63 at a dose of 2 µg at intervals of 8 days. OM-294-MP adjuvant is mixed with both doses of antigen, BCG is mixed only with the first dose. Each mouse is administered 2×50 µg of OM-294-MP or 200 µg of BCG. A control group is injected with antigen alone (without adjuvant). Ten days after the second injection, the inguinal and periaortic lymph node cells (groups of 3 mice each) are cultured and the proliferation response to the purified gp63 antigen is assayed by measuring (3H-TdR) thymidine take-up. In vitro cytokine production in terms of γ IFN and IL-4 by secreted by lymph node lymphocytes rechallenged in vitro with the gp63 antigen is also determined by ELISA (MIF100 IFN and M4000 IL-4 kits, R&D Systems, Europe Ltd., Abingdon, UK) on each supernatant sample of lymph node lymphocyte culture prior to the addition of $^3$H-TdR.

Values reported in the tables for $^3$H-TdR take-up, stand for the arithmetic mean±standard deviation (triplicates) expressed in cpm and values relating to cytokines in the supernatant fluid correspond to the arithmetic mean±standard deviation (triplicates) expressed in pg per ml.

Antigen: A gp63 stock solution is prepared at a concentration of 40 μg/ml in 0.9% NaCl.

Adjuvants: The stock solution of OM-294-MP is prepared at a concentration of 1 mg/ml in water for injection, with addition of 0.1% triethanolamine. The negative control consists of a PBS solution without antigen.

Antigen-Adjuvant mixture: Adjuvants are allowed to stand for 10 minutes at 37° C. before vortex treatment for 3 minutes. Then, the antigen (1 volume) and the adjuvant (1 volume) are mixed and vortexed briefly before incubation for 20 minutes at 37° C., and finally the whole mixture is vortexed for 3 minutes.

Results

Figure 30:
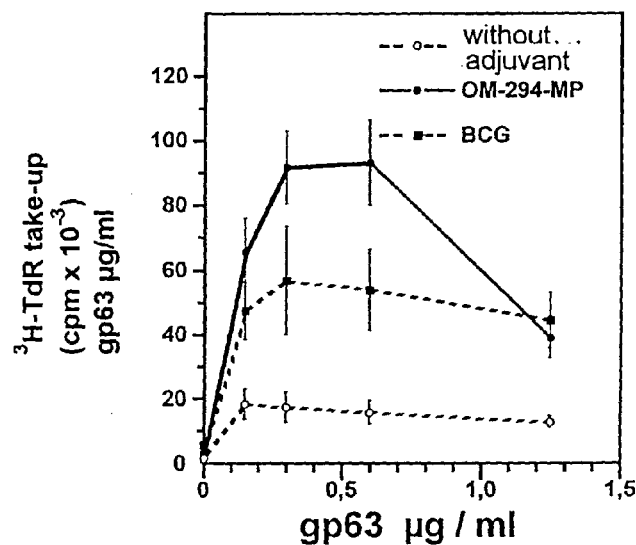
FIGS. 30(a) and 30(b) are graphs of anti-gp63 immune response and FIGS. 31(a) and 31(b) are graphs of lymph node lymphocyte response.
Figure 30:
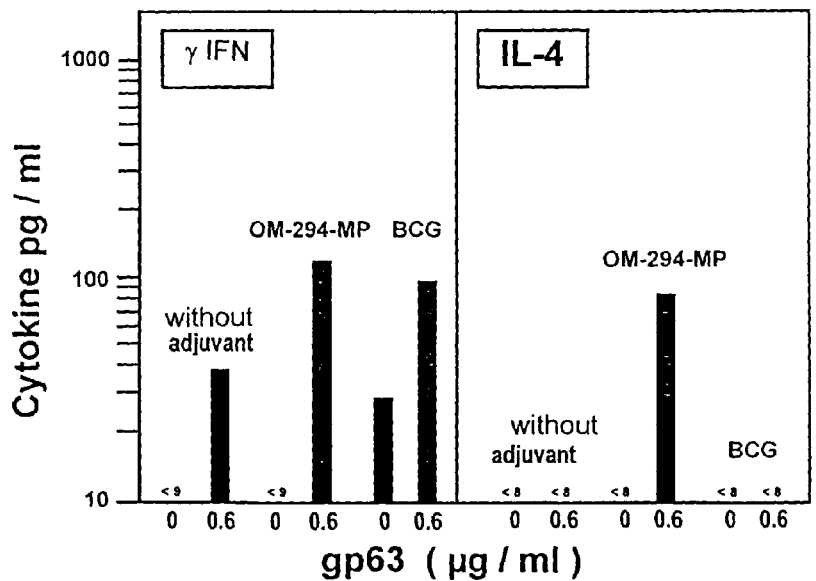

In mice immunized with gp63 antigen, OM-294-MP adjuvant induces a better lymphocyte proliferation response (table (a) and FIG. 30 (*a*)) than BCG. In fact, with respect to cultures from animals that have been immunized without adjuvant, the increase in proliferation rate ranges from 3.1 to 6 folds for OM-294-MP product while it does not exceed 3.5 folds for BCG (2.6–3.5).

In those lymphocyte cultures, cytokine production is measured in the supernatant fluid (Table (b) and FIGURE (30 (b)). It is noted that antigen gp63 induces γ IFN secretion in quantities equivalent to mice treated by OM-294-MP or BCG as adjuvant. By contrast, OM-294-MP adjuvant seems to favor secretion of substantial quantities of IL-4 by (anti-gp63) immune lymphocytes while BCG treated murine lymphocytes secrete minor or even undetectable quatities of said cytokine.

Table (a) Effect of OM-294-MP adjuvant on immune respone against gp63 antigen, as measured by murine T lymphocyte proliferation in response to gp63 antigen in vitro

| gp63 in vitro (μg/ml) | without adjuvant (cpm × 10$^{-3}$/ml) | OM-294-MP (cpm × 10$^{-3}$/ml) | BCG (cpm × 10$^{-3}$/ml) |
|---|---|---|---|
| 0 | 1.4 ± 0.4 | 2.8 ± 0.7 | 5.3 ± 1.1 |
| 0.16 | 18 ± 5 | 65 ± 11 | 47 ± 9 |
| 0.31 | 17 ± 5 | 92 ± 11 | 57 ± 17 |
| 0.62 | 16 ± 4 | 93 ± 13 | 54 ± 13 |
| 1.25 | 13 ± 2 | 39 ± 7 | 44 ± 9 |

Values reported in Table (a) stand for the arithmetic mean take-up ± standard deviation (triplicate cultures)

Table (b) Effect of OM-294-MP adjuvant administered in vivo in conjunction with gp63 antigen on in vitro production of cytokines by lymph node lymphocytes

| gp63 in vitro | without adjuvant | 294-MP | BCG |
|---|---|---|---|
| γ IFN concentration (pg/ml) | | | |
| 0 | <9 | <9 | 27 |
| 0.3 | 78 | 135 | 200 |
| 0.6 | 38 | 120 | 105 |
| IL-4 concentration (pg/ml) | | | |
| 0 | <8 | <8 | <8 |
| 0.3 | <15 | 125 | 15 |
| 0.6 | <8 | 83 | <8 |

OM-294-MP adjuvant potentiates specific T response in vitro in CBA mice which have been immunized with gp63 (an amphophilic antigen of the *Leishmania* parasite) as assayed by lymphocyte proliferation and antigen-induced γ IFN and IL-4 production.

16. Effectiveness of OM-294-MP Adjuvant During anti-LmCPb T-Primary Response in a CBA Mouse-Based Immunization Model when Administered by Subcutaneous Route with *Leishmania Mexicana* LmCPb Antigen Procedure CBA mice were administered through the tail a single injection of LmCPb in a 2 μg dose either in combination or not with 50 μg of OM-294-MP adjuvant. A control group was administered one injection of physiological saline buffer (non immunized subjects). Eleven days later, cells of the inguinal and periaortic lymph nodes (groups of 3 mice each) were cultured and the proliferative response directed to the purified LmCPb antigen, to a preparation of whole amastigotes of *Leishmania mexicana* and to concanvalin A (ConA) was evaluated by measuring tritiated thymidine take-up ($^3$H-TdR). γ IFN and IL-4 cytokine production by lymph node lymphocytes rechallenged in vitro with LmCPb antigen of *Leishmania mexicana* or by amastigotes was equally determined by ELISA (MIF00 γ IFN & M4000 IL-4 kits, R&D Systems Europe Ltd, Abingdon, UK) using a sample of each culture supernatant of lymph node lymphocytes before addition of $^3$H-TdR.

Values reported in the tables stand for the mean value±standard deviation (triplicate) expressed in cpm for $^3$H-TdR take-up and the arithmetic mean±standard deviation (triplicate) expressed in pg per ml for cytokine production in supernatant fluids.

Antigen: LmCPb stock solution is prepared at a concentration of 40 μg/ml in PBS (2×).

Adjuvants: OM-294-MP stock solution is prepared at a concentration of 1 mg/ml in water for injection with addition of 0.1% triethanolamine. The negative control consists of a PBS solution without antigen.

Antigen-adjuvant mixture: Adjuvants are maintained for 10 minutes at 37° C. before vortexing for 3 minutes. Then, the antigen (1 volume) and the adjuvant (1 volume) are mixed and vortexed briefly before being incubated for 20 minutes at 37° C., and finally the whole mixture is vortexed again for 3 minutes.

Results

Figure 31:
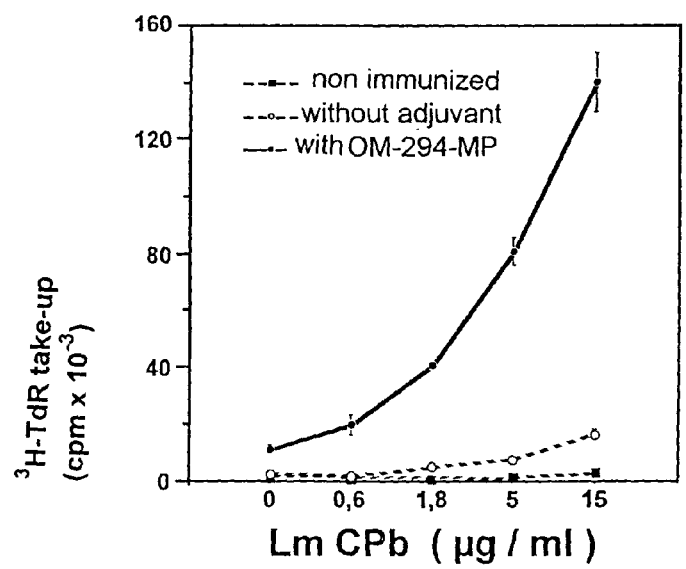
Figure 31:
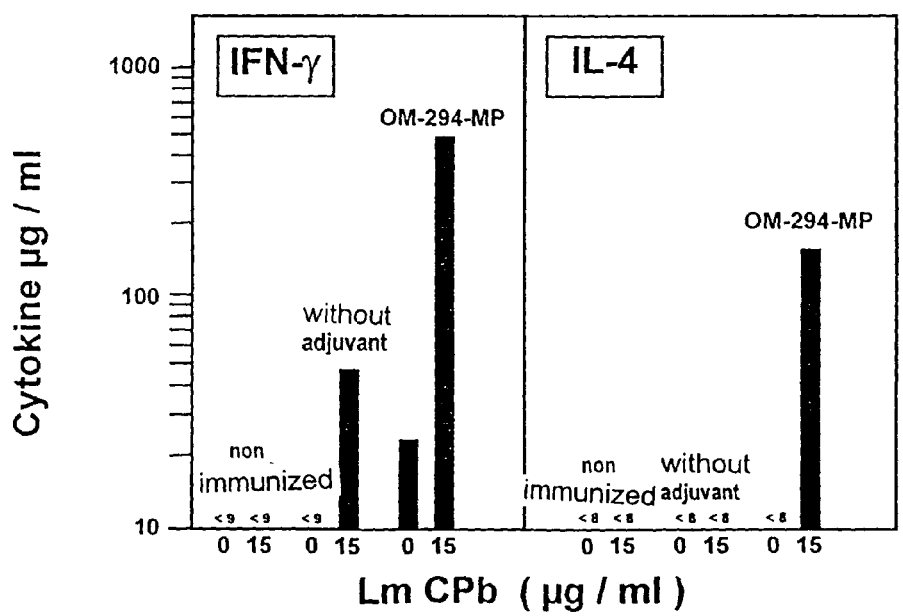

In absence of any stimulus in the culture medium, OM-294-MP adjuvant promotes development of lymphocytes which undergo spontaneous proliferation (Table (a) and FIG. 31 (*a*)) and secrete trace amounts of γ IFN (Table (b) and FIG. 31(*b*)). This reaction is strongly potentiated when purified LmCPb antigen or an extract of whole parasite is added to the cultures. In this experiment, the adjuvant is observed to exert a clear influence on the induction of sensitized lymphocytes (anti-LmCPb) able to secrete substantial quantities of IL-4 (Table (b) and FIG. 31 (*b*)).

Table (a) in vitro proliferative response of lymph node cells immunized in vivo by LmCPb: effect of OM-294-MP adjuvant

| | $^3$H-TdR take-up (cpm × 10$^{-3}$/ml) | | |
|---|---|---|---|
| Antigen in vitro | Non immunized | Without adjuvant | OM-294-MP |
| No stimulant | 0.9 ± 0.3 | 2.2 ± 0.7 | 11 ± 2 |
| LmCPb 0.6 μg/ml | 0.8 ± 0.4 | 1.7 ± 0.1 | 19 ± 4 |
| LmCPb 1.7 μg/ml | 0.9 ± 0.1 | 4.6 ± 1.6 | 40 ± 4 |
| LmCPb 5 μg/ml | 1.3 ± 0.8 | 7.2 ± 0.6 | 80 ± 5 |
| LmCPb 15 μg/ml | 2.6 ± 0.4 | 16.2 ± 2.1 | 140 ± 10 |
| Amastigotes 1.9 × 10$^{-6}$/ml | 0.8 ± 0.2 | 1.7 ± 0.1 | 44 ± 7 |
| Amastigotes 6 × 10$^{-6}$/ml | 1.5 ± 0.2 | 4.6 ± 0.6 | 79 ± 6 |
| Amastigotes 17 × 10$^{-6}$/ml | 2.9 ± 0.6 | 7.2 ± 0.6 | 119 ± 4 |
| Con A 5 μg/ml | 123 ± 33 | 193 ± 17 | 196 ± 10 |

Table (b) In vitro secretion of cytokines by lymph node lymphocytes immunized in vivo by LmCPb: Effect of OM-294-MP adjuvant on primary response

| In vitro stimulant | Non immunized | without adjuvant | OM-294-MP |
|---|---|---|---|
| γ IFN production (pg/ml) | | | |
| No stimulant | <9 | <9 | 25 |
| LmCPb 15 µg/ml | <9 | 46 | 480 |
| Amastigotes 17 × $10^{-5}$/ml | <9 | 95 | 320 |
| Con A 5 µg/ml | >1800 | >1800 | >1800 |
| IL-4 production (pg/ml) | | | |
| No challenge | <8 | <8 | <8 |
| LmCPb 15 µg/ml | <8 | <8 | 130 |
| Amastigotes 17 × $10^{-5}$/ml | <8 | <8 | 65 |
| Con A 5 µg/ml | 92 | 190 | 360 |

OM-294-MP adjuvant is also very effective during the primary T-response (following a single vaccine injection). Properties of the adjuvant effect on this response (increase of lymphocyte proliferation, induction of cytokine production) are similar to those observed during the response to two vaccine injections.

17. Evaluation of OM-294-MP and OM-294-DP Adjuvant Properties in CBA Mouse-Based Immunization Model Through Subcutaneous Administration of *Leishmania mexicana* LmCPb Antigen: Comparison with BCG Procedure CBA mice (8 mice per group) were administered in the tail 2 subcutaneous injections of 3–5 µg of purified LmCPb at intervals of 8 days. OM-294-MP and OM-294-DP adjuvants were mixed with both doses of antigen, whereas BCG was only mixed with the first one. Each mouse received 2×50 µg of OM adjuvant or 200 µg of BCG. Eight days following the second injection, the periaortic and inguinal lymph nodes (3 mice per group) are removed and the cells are cultured in order to assay the proliferative response to purified LmCPb antigen, or respectively, the proliferative response to a whole preparation of *Leishmania mexicana* amastigotes or to Concanavalin A (Con A). The proliferative response is evaluated by measuring tritiated thymidine take-up ($^3$H-TdR). γ IFN and IL-4 cytokine production by lymph node lymphocytes rechallenged in vitro by the LmCPb antigen of *Leishmania mexicana* or by the amastigotes or by Con A is determined by ELISA (MIF00 γ IFN & M4000 IL-4 kits, R&D Systems Europe Ltd., Abingdon, UK) using a sample of each culture 10 supernatant of lymph node lymphocytes before addition of $^3$H-TdR.

Values reported in the tables stand for the arithmetic mean±standard deviation expressed in % of standard regarding antibody titer, the arithmetic mean±standard deviation (triplicates) expressed in cpm for $^3$H-TdR take-up, and the arithmetic mean±standard deviation (triplicates) expressed in pg per ml for cytokine production.

Antigen: LmCPb stock solution is prepared at a concentration of 60–100 µg/ml in 0.9% NaCl.

Adjuvants: OM-294-MP and OM-294-DP stock solutions are prepared at a concentration of 1 mg/ml in water for injection with addition of 0.1% triethanolamine for OM-294-MP. The negative control consists of a PBS solution without antigen.

Antigen-adjuvant mixture: Adjuvants are maintained for 10 minutes at 37° C. before vortexing for 3 minutes. Then, the antigen (1 volume) and the 0.9% adjuvant (1 volume) are mixed and vortexed briefly before being incubated for 20 minutes at 37° C., and finally the whole mixture is vortexed again for 3 minutes.

Results

In mice immunized with LmCPb antigen (Tables (a) and (b), FIGS. 32 (*a*) and (*b*)), the products OM-294-MP and OM-294-DP produce a similar effect to that observed in mice which develop an immune response against gp63. Therefore, in presence of LmCPb (15 µg/ml), the extent of proliferation of cultures derived from mice which have been immunized with antigen plus OM-294-MP and OM-294-DP adjuvants is respectively 23 and 28 times higher than cultures orginating from mice administered antigen alone (without adjuvant). The impact of BCG in these conditions is smaller, since the increase in proliferation is merely 11 fold. Analogous effects are seen in cultures challenged with purified antigen or a whole extract of *Leishmania* parasite, and for all antigen concentrations being tested.

γ IFN production in response to LmCPb antigen tends to be a bit higher with product OM-294-DP than with BCG (Table (b) and FIG. 32 (*b*)). It shall be noted that in this experiment, lymphocytes proliferate and secrete substantial amounts of γ IFN even though the antigen might not have been added to the culture medium. In this case, OM-294-DP adjuvant tends to be somewhat more effective than BCG. A clear difference between OM-294-MP, OM-294-DP and BCG adjuvants respectively is observed as reported above regarding the development of lymphocytes able to produce IL-4. The quantity of IL-4 being produced under the influence of OM-294-MP and OM-294-DP adjuvants is significant since it matches the quantity secreted by lymphocytes exposed to Con A, a powerful non specific stimulant for lymphocytes (see Table (a) and (b)).

Table (a) In vitro proliferative response to lymph node cells derived from mice immunized in vivo with LmCPb: effect of different adjuvants

| | $^3$H-TdR take-up (cpm × $10^{-3}$/ml) | | | |
|---|---|---|---|---|
| in vitro stimulant | without adjuvant | OM-294-DP | OM-294-MP | BCG |
| No stimulant | 1.7 ± 0.6 | 21.8 ± 2.2 | 17.1 ± 2.5 | 18.6 ± 4.8 |
| LmCPb 0.6 µg/ml | 0.8 ± 0.3 | 40.9 ± 12.7 | 22.9 ± 2.8 | 19.0 ± 7.4 |
| LmCPb 1.7 µg/ml | 2.4 ± 0.1 | 57.2 ± 10.9 | 34.1 ± 4.1 | 39.8 ± 5.7 |
| LmCPb 5 µg/ml | 2.8 ± 0.6 | 70.2 ± 9.2 | 70.3 ± 6.4 | 44.0 ± 10.4 |
| LmCPb 15 µg/ml | 4.3 ± 0.1 | 100.0 ± 6.5 | 124.2 ± 12.0 | 46.2 ± 0.3 |
| Amastigotes 2 × $10^{-6}$/ml | 2.4 ± 0.6 | 61.0 ± 1.7 | 28.4 ± 8.3 | 24.4 ± 4.3 |
| Amastigotes 6 × $10^{-6}$/ml | 2.3 ± 0.7 | 81.5 ± 5.5 | 66.1 ± 4.5 | 23.6 ± 2.5 |

Table (a) In vitro proliferative response to lymph node cells derived from mice immunized in vivo with LmCPb: effect of different adjuvants

| | $^3$H-TdR take-up (cpm × $10^{-3}$/ml) | | | |
|---|---|---|---|---|
| in vitro stimulant | without adjuvant | OM-294-DP | OM-294-MP | BCG |
| Amastigotes 17 × $10^{-6}$/ml | 1.7 ± 0.4 | 78.2 ± 7.8 | 68.7 ± 2.3 | 23.4 ± 4.0 |
| Con A 5 µg/ml | 188.1 ± 21.0 | 135.9 ± 3.7 | 151.4 ± 3.7 | 119.7 ± 28.5 |

Values reported in the table stand for the arithmetic mean ± standard deviation in terms of tracer take-up (triplicate cultures)

Table (b) in vitro cytokine production by lymph node lymphocytes from mice immunized in vivo by LmCPb antigen: Effect of different adjuvants

| In vitro stimulant | without adjuvant | OM-294-DP | OM-294-DP | BCG |
|---|---|---|---|---|
| γ IFN concentration (pg/ml) | | | | |
| No stimulant | <9 | 460 | 240 | 280 |
| LmCPb 15 µg/ml | 44 | 520 | 360 | 460 |
| Amastigotes 17 × $10^{-6}$/ml | 14 | >600 | >600 | 480 |
| Con A 5 µg/ml | 1200 | 1200 | 1900 | >3000 |
| IL-4 concentration (pg/ml) | | | | |
| No stimulant | <15 | <8 | <8 | <8 |
| LmCPb 15 µg/ml | <15 | 110 | 88 | 36 |
| Amastigotes 17 × $10^{-6}$/ml | <8 | 130 | 110 | 29 |
| Con A 5 µg/ml | 40 | 230 | 85 | 105 |

OM-294-MP and OM-294-DP adjuvants potentiate efficiently the immune response against a soluble antigen of *Leishmania*, LmCPb protease. This is reflected in vitro by an increase in proliferative response followed by induction of γ IFN and IL-4 production in significant amounts.

EXAMPLE VI
Aqueous solution for injection

| | |
|---|---|
| Compound of example III | 1 g |
| Polysorbate 80 | 0.2 g |
| Sodium chloride | 9 g |
| Distilled water for injection q.s. | 1000 ml |

The solution was adjusted to pH 7.5 with 0.1 M HCl and then was sterilized by membrane filtration on a 0.22 µm Steritop Express 1000 membrane (PES membrane, 90 mM, SCGP T10 RE, Millipore Corporation, Bedford, Mass., USA). The sterile solution was divided into sterile ampuls of 1 ml.

Lyophilized product

| | |
|---|---|
| Compound of example IV | 2 g |
| Polysorbate 80 | 0.2 g |
| Sodium chloride | 9 g |
| Mannitol | 10 g |
| Ascorbic acid | 0.1 g |
| Distilled water for injection q.s. | 1000 ml |

The solution was adjusted to pH 7.4 with 0.1M HCl, then sterilized by membrane filtration through a 0.22 µl Steritop Express 1000 membrane (PES membrane, 90 mm, SCGP T10 RE, Millipore Corporation, Bedford, Mass., USA). The sterile solution was divided into sterile multidose vials by dispensing 1 ml per vial, and then freeze-dried.

The invention claimed is:

1. A N-acyl dipeptidic compound of the formula

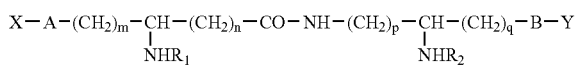

(I)

wherein $R_1$ and $R_2$ are each an acyl moiety of a saturated or unsaturated carboxylic acid of 2 to 24 carbon atoms unsubstituted or substituted with at least one member selected from the group consisting of hydroxyl, alkyl and alkoxy of 1 to 24 carbon atoms, amino, acyloxy of an organic carboxylic acid of 1 to 24 carbon atoms and acylamino and acylthio of a carboxylic acid of 1 to 24 carbon atoms and alkylthio of 1 to 24 carbon atoms, m, p and q are integers from 1 to 10, n is an integer from 0 to 10, X and Y are independently hydrogen or an acid group selected from the group consisting of carboxy [$(C_{1-5})$alkyl]
  CH—[$(CH_2)_{m1}$COOH][$(CH_2)_{n1}$COOH] with $m_1$=0 to 5 and $n_1$=0 to 5
  phosphono [$(C_{1-5})$alkyl]
  dihydroxyphosphonyloxy[$(C_{1-5})$alkyl]
  dimethoxyphosphonyl
  phosphono
  hydroxysulfonyl
  hydroxysulfonyl [$(C_{1-5})$alkyl] and
  hydroxysulfonyloxy [$(C_{1-5})$alkyl]

in neutral or charged form provided that at least one of the substituents X and Y is other than hydrogen and A and B are individually selected from the group consisting of oxygen, sulfur and —NH—.

2. A compound of claim 1 wherein at least one of X and Y is other than hydrogen in salt form with a non-toxic, pharmaceutically acceptable base.

3. A compound of claim 1 having the formula

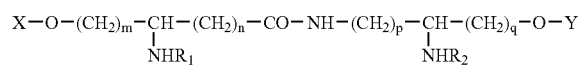

(I')

wherein $R_1$ and $R_2$ are individually an acyl moiety derived from a saturated or unsaturated carboxylic acid of 2 to 24 carbon atoms, unsubstituted or substituted with at least one member selected from the group consisting of hydroxyl, alkyl and alkoxy of 1 to 24 carbon atoms, amino, acyloxy of an organic carboxylic acid of 2 to 24 carbon atoms and acylamino and acylthio of an organic carboxylic acid of 2 to 24 carbon atoms and alkylthio of 1 to 24 carbon atoms, m, p and q are individually integers from 1 to 10, n is an integer from 0 to 10 and X and Y are individually hydrogen or phosphono.

4. A compound of formula I of claim 1 containing elements having (R) or (S) configuration, or racemates thereof.

5. A compound of claim 1 selected from the group consisting of 3-(3-dodecanoyloxytetradecanoylamino) 9-(3-hydroxytetradecanoylamino)-4-oxo-5-azadecan-1,10-diol, the 1-dihydrogenphosphate thereof and the 10-dihydrogenphosphate thereof, as well as the addition salts with an organic or a mineral base.

6. A compound of claim 1 selected from the group consisting of 3-(3-dodecanoyloxytetradecanoylamino) 9-(3-hydroxytetradecanoylamino)-4-oxo-5-azadecan-1,10-diol, 1,10-bis-(dihydrogenphosphate) and its addition salts with an organic or a mineral base.

7. A compound of claim 1 selected from the group consisting of 3-(3-hydroxytetradecanoylamino)-9-(3-dodecanoyloxytetradecanoylamino)-4-oxo-5-azadecan-1,10-diol, 1,10-bis-(dihydrogenphosphate) and its addition salts with an organic or a mineral base.

8. A compound of claim 1 selected from the group consisting of 3-(3-dodecanoyloxytetradecanoylamino) 9-(3-hydroxytetradecanoylamino)-4-oxo-5-azadecan-1,10-diol, mono 1-dihydrogenphosphate and its addition salts with an organic or mineral base.

9. A compound of claim 1 selected from the group consisting of 3-(3-hydroxytetradecanoylamino)-9-(3-dodecanoyloxytetradecanoylamino)-4-oxo-5-azadecan-1,10-diol, mono 1-dihydrogenphosphate and its addition salts with an organic or a mineral base.

10. A pharmaceutical composition containing as an active ingredient at least one compound of the formula I in accordance with claim 1:

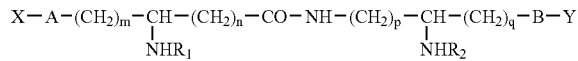

wherein $R_1$ and $R_2$ are each an acyl moiety of a saturated or unsaturated carboxylic acid of 2 to 24 carbon atoms, unsubstituted or substituted with at least one member selected from the group consisting of hydroxyl, alkyl and alkoxy of 1 to 24 carbon atoms, acyloxy of an organic carboxylic acid of 1 to 24 carbon atoms, acylamino and acylthio of a carboxylic acid of 1 to 24 carbon atoms and alkylthio wherein the alkyl group has from 1 to 24 carbon atoms, m, p and q are integers from 1 to 10, n is an integer from 0 to 10, X and Y each are hydrogen or an acid group as defined in claim 1 either in neutral or charged form, A and B are individually oxygen, sulfur or —NH—, together or in admixture with a non-toxic, pharmaceutically acceptable, inert carrier.

11. The pharmaceutical composition in accordance with claim 10, wherein the compound of formula I is a compound of the type where X and/or Y are phosphono and further A and B are an oxygen atom.

12. The pharmaceutical composition in accordance with claim 10, wherein the active ingredient is in salt form with an organic or mineral base intended for therapeutic use.

13. The pharmaceutical composition in accordance with claim 10, wherein the active ingredient is in the form of a pure enantiomer or in the form of a mixture of stereoisomers.

14. The method of inducing immuno-modulation in warm-blooded animals in need thereof comprising administering to said warm-blooded animals an immuno-modulating effective amount of a compound of claim 1.

* * * * *